United States Patent
Kahvejian et al.

(10) Patent No.: US 10,457,740 B1
(45) Date of Patent: Oct. 29, 2019

(54) METHODS AND COMPOSITIONS FOR TREATING CANCER USING P2RX2 INHIBITORS

(71) Applicant: Flagship Pioneering Innovations V, Inc., Cambridge, MA (US)

(72) Inventors: Avak Kahvejian, Lexington, MA (US); Jordi Mata-Fink, Baltimore, MD (US); Jonathan Barry Hurov, Bedford, MA (US); Alexandra Lantermann, Boston, MA (US)

(73) Assignee: Flagship Pioneering Innovations V, Inc., Cambridge, MA (US)

( * ) Notice: Subject to any disclaimer, the term of this patent is extended or adjusted under 35 U.S.C. 154(b) by 0 days.

(21) Appl. No.: 16/140,151

(22) Filed: Sep. 24, 2018

Related U.S. Application Data

(60) Provisional application No. 62/623,236, filed on Jan. 29, 2018.

(51) Int. Cl.
*A61K 38/00* (2006.01)
*A61P 35/00* (2006.01)
*C07K 16/30* (2006.01)

(52) U.S. Cl.
CPC ............ *C07K 16/303* (2013.01); *A61P 35/00* (2018.01); *C07K 2317/54* (2013.01); *C07K 2317/565* (2013.01); *C07K 2317/72* (2013.01); *C07K 2317/75* (2013.01); *C07K 2319/30* (2013.01)

(58) Field of Classification Search
None
See application file for complete search history.

(56) References Cited

FOREIGN PATENT DOCUMENTS

| WO | WO-2018/022668 A2 | 2/2018 | |
|---|---|---|---|
| WO | WO-2018022668 A2 * | 2/2018 | ............ A61K 38/18 |

OTHER PUBLICATIONS

Burnstock G and Di Virgilio F "Purinergic signalling and cancer" Purinergic Signaling 9:491-540. (Year: 2013).*
Cui et al. "Targeting calcium signaling in cancer therapy" Acta Pharmaceutica Sinica B 7:3-17. (Year: 2017).*
Di Virgilio F and Adinolfi E "Extracellular purines, purinergic receptors and tumor growth" Oncogene 36:293-303. (Year: 2016).*
Di Virgilio et al. "Extracellular ATP and P2 purinergic signalling in the tumour microenvironment" Nature Reviews Cancer 18:601-618. (Year: 2018).*
Anonymous "Expression of P2RX2 in cancer—Summary—The Human Protein Atlas" https://www.proteinatlas.org/NESG00000187848-P2RX2/pathology#gene_information (Year: 2018).*
Kendrick N "A gene's mRNA level does not usually predict its protein level" Kendrick Labs, Inc. (Year: 2014).*
Bhargava et al. "Suramin Inhibits Not Only Tumor Growth and Metastasis but Also Angiogenesis in Experimental Pancreatic Cancer" J. Gastrointest. Surg. 11:171-178. (Year: 2007).*
Trujillo et al. "Inhibition Mechanism of the Recombinant Rat P2X2 Receptor in Glial Cells by Suramin and TNP-ATP" Biochemistry 45:224-233. (Year: 2006).*

* cited by examiner

*Primary Examiner* — Christina Bradley
*Assistant Examiner* — Zachary J Miknis
(74) *Attorney, Agent, or Firm* — Clark & Elbing LLP

(57) ABSTRACT

The present invention provides methods for treating cancer using P2RX2 inhibitors, such as P2RX2 inhibitory antibodies, among others. The invention also features compositions containing P2RX2 inhibitors, methods of diagnosing patients with P2RX2-associated cancer, and methods of predicting the response of cancer in a subject to treatment with P2RX2 inhibitors.

1 Claim, No Drawings

METHODS AND COMPOSITIONS FOR TREATING CANCER USING P2RX2 INHIBITORS

BACKGROUND

Cancer is still one of the deadliest threats to human health. In 2012, there were 14 million new cases of cancer worldwide and 8.2 million cancer-related deaths. The number of new cancer cases is expected to rise to 22 million by 2030, and worldwide cancer deaths are projected to increase by 60%. Thus, there remains a need in the field for treatments for cancer.

SUMMARY OF THE INVENTION

The present invention provides methods for treating cancer using purinergic receptor P2X2 (P2RX2) inhibitors, such as P2RX2 inhibitory antibodies, among others. The invention also features compositions containing P2RX2 inhibitors, methods of diagnosing patients with P2RX2-associated cancer, and methods of predicting the response of cancer in a subject to treatment with P2RX2 inhibitors.

In a first aspect, the invention provides a method of treating a subject with cancer, by administering to the subject an effective amount of a P2RX2 inhibitor.

In another aspect, the invention provides a method of treating a subject with cancer by contacting a tumor, tumor microenvironment, site of metastasis, cancer cell, metastatic cancer cell, or stromal cell in a tumor microenvironment with an effective amount of a P2RX2 inhibitor.

In another aspect, the invention provides a method of treating a subject identified as having cancer by administering to the subject an effective amount of a P2RX2 inhibitor.

In another aspect, the invention provides a method of treating a subject identified as having cancer by contacting a tumor, tumor microenvironment, site of metastasis, cancer cell, metastatic cancer cell, or stromal cell in a tumor microenvironment with an effective amount of a P2RX2 inhibitor.

In another aspect, the invention provides a method of reducing or inhibiting tumor growth by contacting the tumor with an effective amount of a P2RX2 inhibitor. In some embodiments, the tumor is a P2RX2-associated tumor. In some embodiments, the tumor is a pancreatic tumor.

In another aspect, the invention provides a method of reducing or inhibiting cancer cell proliferation by contacting the cancer cell with an effective amount of a P2RX2 inhibitor. In some embodiments, the cancer cell is a P2RX2-associated cancer cell. In some embodiments, the cancer cell is a pancreatic cancer cell.

In some embodiments of any of the above aspects, the cancer is P2RX2-associated cancer.

In another aspect, the invention provides a method of treating a subject with cancer by: a) identifying a subject with P2RX2-associated cancer; and b) administering to the subject an effective amount of a P2RX2 inhibitor.

In another aspect, the invention provides a method of treating a subject with cancer by: a) identifying a subject with P2RX2-associated cancer; and b) contacting a tumor, tumor microenvironment, site of metastasis, cancer cell, metastatic cancer cell, or stromal cell in a tumor microenvironment with an effective amount of a P2RX2 inhibitor.

In another aspect, the invention provides a method of treating a subject with P2RX2-associated cancer by administering to the subject an effective amount of a P2RX2 inhibitor.

In another aspect, the invention provides a method of treating a subject identified as having P2RX2-associated cancer by administering to the subject an effective amount of a P2RX2 inhibitor.

In another aspect, the invention provides a method of treating a subject with P2RX2-associated cancer by contacting a tumor, tumor microenvironment, site of metastasis, cancer cell, metastatic cancer cell, or stromal cell in a tumor microenvironment with an effective amount of a P2RX2 inhibitor.

In some embodiments of any of the above aspects, the method includes contacting a tumor with an effective amount of a P2RX2 inhibitor. In some embodiments of any of the above aspects, the method includes contacting a tumor microenvironment with an effective amount of a P2RX2 inhibitor. In some embodiments of any of the above aspects, the method includes contacting a site of metastasis with an effective amount of a P2RX2 inhibitor. In some embodiments of any of the above aspects, the method includes contacting a cancer cell with an effective amount of a P2RX2 inhibitor. In some embodiments of any of the above aspects, the method includes contacting a metastatic cancer cell with an effective amount of a P2RX2 inhibitor. In some embodiments of any of the above aspects, the method includes contacting a stromal cell in a tumor microenvironment with an effective amount of a P2RX2 inhibitor.

In some embodiments of any of the above aspects, the P2RX2-associated cancer expresses P2RX2. In some embodiments of any of the above aspects, the P2RX2-associated cancer overexpresses P2RX2.

In another aspect, the invention provides a method of predicting the response of a cancer in a subject to treatment with a P2RX2 inhibitor by contacting a cancer cell isolated from the subject with a P2RX2 inhibitor and evaluating the response of the cancer cell.

In some embodiments of the above aspect, the P2RX2 inhibitor is a P2RX2-specific inhibitor.

In some embodiments of the above aspect, the evaluating includes assessing cancer cell growth, cancer cell proliferation, cancer cell metastasis, cancer cell death, cancer cell migration, cancer cell invasion, cancer cell autophagy, or cancer cell P2RX2 expression.

In another aspect, the invention provides a method of predicting the response of a cancer in a subject to treatment with a P2RX2 inhibitor by: a) isolating a cancer cell from the subject; b) measuring the expression of P2RX2 in the cancer cell; and c) comparing P2RX2 expression in the cancer cell to a reference, wherein increased expression of P2RX2 in the cancer cell as compared to the reference indicates that the subject will respond to treatment with a P2RX2 inhibitor.

In another aspect, the invention provides a method of determining if a cancer cell expresses functional P2RX2 by contacting a cell with ATP and evaluating intracellular calcium levels. In some embodiments, and increase in intracellular calcium levels indicates that the cancer cell expresses functional P2RX2.

In some embodiments of any of the above aspects, the method further includes contacting the cancer cell with a P2RX2 inhibitor.

In another aspect, the invention provides a method of characterizing a cancer in a subject by: a) isolating a cancer cell from the subject; b) measuring the expression of P2RX2 in the cancer cell; and c) comparing P2RX2 expression in the cancer cell to a reference, wherein increased expression of P2RX2 in the cancer cell as compared to the reference indicates that the subject has P2RX2-associated cancer.

In another aspect, the invention provides a method of identifying a subject as having P2RX2-associated cancer by: a) isolating cancer cell from the subject; b) measuring the expression of P2RX2 in the cancer cell; and c) comparing P2RX2 expression in the cancer cell to a reference, wherein increased expression of P2RX2 in the cancer cell as compared to the reference indicates that the subject has P2RX2-associated cancer.

In some embodiments of any of the above aspects, the method further includes providing a P2RX2 inhibitor suitable for administration to the subject. In some embodiments of any of the above aspects, the method further includes administering to the subject an effective amount of a P2RX2 inhibitor.

In some embodiments of any of the above aspects, the P2RX2 inhibitor is a P2RX2-specific inhibitor.

In some embodiments of any of the above aspects, the P2RX2 inhibitor or P2RX2-specific inhibitor is a P2RX2 function blocker.

In some embodiments of any of the above aspects, the P2RX2 inhibitor or P2RX2-specific inhibitor is a P2RX2 signaling inhibitor.

In some embodiments of any of the above aspects, the P2RX2 inhibitor or P2RX2-specific inhibitor reduces P2RX2 expression or activity.

In some embodiments of any of the above aspects, the P2RX2 inhibitor or P2RX2-specific inhibitor reduces P2RX2 binding to a binding partner.

In some embodiments of any of the above aspects, the cancer is pancreatic cancer, melanoma, small cell lung cancer, non-small cell lung cancer, gastric cancer, colorectal cancer, head and neck cancer, ovarian cancer, testicular cancer, thymoma, uterine cancer, kidney cancer, acute myeloid leukemia, diffuse large B-cell lymphoma, prostate cancer, breast cancer, or hepatocellular carcinoma. In some embodiments, the cancer is pancreatic cancer.

In some embodiments of any of the above aspects, the cancer is P2RX2-associated cancer. In some embodiments, the P2RX2-associated cancer expresses P2RX2. In some embodiments, the P2RX2-associated cancer overexpresses P2RX2.

In some embodiments of any of the above aspects, the P2RX2 inhibitor or P2RX2-specific inhibitor is administered locally. In some embodiments, the P2RX2 inhibitor or P2RX2-specific inhibitor is administered intratumorally. In some embodiments, the P2RX2 inhibitor or P2RX2-specific inhibitor is administered to or near a site of metastasis. In some embodiments, the P2RX2 inhibitor or P2RX2-specific inhibitor is administered to or near a tumor microenvironment.

In some embodiments of any of the above aspects, the method further includes administering a second therapeutic agent.

In some embodiments of any of the above aspects, the P2RX2 inhibitor or P2RX2-specific inhibitor decreases tumor volume, tumor or cancer cell growth, decreases tumor innervation, decreases cancer cell proliferation, decreases cancer cell invasion, decreases cancer cell migration, decreases cancer cell metastasis, decreases tumor innervation, induces cancer cell autophagy, increases cancer cell death, increases time to recurrence, reduces cancer cell P2RX2 expression, or improves survival.

In some embodiments of any of the above aspects, the method further includes measuring one or more of tumor volume, tumor growth, tumor innervation, cancer cell proliferation, cancer cell invasion, cancer cell migration, cancer cell metastasis, cancer cell death, cancer cell autophagy, or P2RX2 expression before administration of the P2RX2 inhibitor or P2RX2-specific inhibitor.

In some embodiments of any of the above aspects, the method further includes measuring one or more of tumor volume, tumor or cancer cell growth, tumor innervation, cancer cell proliferation, cancer cell invasion, cancer cell metastasis, cancer cell death, cancer cell autophagy, or P2RX2 expression after administration of the P2RX2 inhibitor or P2RX2-specific inhibitor.

In some embodiments of any of the above aspects, the P2RX2 inhibitor or P2RX2-specific inhibitor is administered in an amount sufficient to decrease tumor innervation, decrease nerve activity in a tumor, treat the cancer or tumor, cause remission, reduce tumor or cancer cell growth, reduce tumor volume, reduce tumor or cancer cell metastasis, reduce tumor or cancer cell invasion, reduce tumor or cancer cell proliferation, reduce tumor number, reduce tumor or cancer cell migration, reduce tumor P2RX2 expression, increase cancer cell death, induce cancer cell autophagy increase time to recurrence, or improve survival.

In some embodiments of any of the above aspects, the method further includes monitoring tumor or cancer progression (e.g., monitoring one or more of tumor volume, tumor or cancer cell growth, tumor innervation, tumor number, cancer cell proliferation, cancer cell invasion, cancer cell metastasis, cancer cell death, cancer cell autophagy, or P2RX2 expression) of after administration of the P2RX2 inhibitor or P2RX2-specific inhibitor.

In another aspect, the invention provides an anti-cancer therapy containing a P2RX2 inhibitor and a second agent selected from the group consisting of checkpoint inhibitors, chemotherapeutic agents, biologic cancer agents, anti-angiogenic drugs, drugs that target cancer metabolism, antibodies that mark a cancer cell surface for destruction, antibody-drug conjugates, cell therapies, commonly used anti-neoplastic agents, non-drug therapies, neurotransmission blockers, and neuronal growth factor blockers.

In some embodiments of any of the above aspects, the P2RX2 inhibitor is an inhibitory RNA directed to P2RX2. In some embodiments of any of the above aspects, the P2RX2 inhibitor is an inhibitory RNA directed to a P2RX2 binding partner selected from the group consisting of P2RX1, P2RX3, P2RX4, P2RX5, P2RX6, and P2RX7.

In some embodiments of any of the above aspects, the P2RX2 inhibitor is a P2RX2 inhibitory antibody or an antigen binding fragment thereof. In some embodiments of any of the above aspects, the P2RX2 inhibitor is a P2RX2-specific inhibitory antibody or an antigen binding fragment thereof. In some embodiments of any of the above aspects, the P2RX2 inhibitory antibody binds to a P2RX2 binding partner selected from the group consisting of P2RX1, P2RX3, P2RX4, P2RX5, P2RX6, and P2RX7.

In some embodiments of any of the above aspects, the P2RX2 inhibitor is a small molecule inhibitor listed in Table 1. In some embodiments, the small molecule inhibitor is a P2RX2-specific inhibitor.

In some embodiments of any of the above aspects, the P2RX2 inhibitor is a P2RX2-specific inhibitor.

In some embodiments of any of the above aspects, the P2RX2 inhibitor is a P2RX2 function blocker.

In some embodiments of any of the above aspects, the P2RX2 inhibitor is a P2RX2 signaling inhibitor listed in Table 2.

In another aspect, the invention provides a pharmaceutical containing a P2RX2 inhibitor.

In some embodiments of any of the above aspects, the P2RX2 inhibitor is a P2RX2-specific inhibitor. In some embodiments, the P2RX2-specific inhibitor is an inhibitory RNA directed to P2RX2. In some embodiments, the P2RX2-specific inhibitor is a P2RX2-specific antibody or an antigen binding fragment thereof. In some embodiments, the P2RX2-specific inhibitor is a P2RX2-specific small molecule inhibitor listed in Table 1.

In some embodiments of any of the above aspects, the P2RX2 inhibitor is a P2RX2 inhibitory antibody or an antigen binding fragment thereof. In some embodiments, the P2RX2 inhibitory antibody is a P2RX2-specific inhibitory antibody or an antigen binding fragment thereof. In some embodiments, the P2RX2 inhibitory antibody binds to a P2RX2 binding partner selected from the group consisting of P2RX1, P2RX3, P2RX4, P2RX5, P2RX6, and P2RX7.

In some embodiments of any of the above aspects, the P2RX2 inhibitor is a small molecule inhibitor listed in Table 1.

In some embodiments of any of the above aspects, the P2RX2 inhibitor is an inhibitory RNA directed to a P2RX2 binding partner selected from the group consisting of P2RX1, P2RX3, P2RX4, P2RX5, P2RX6, and P2RX7.

In some embodiments of any of the above aspects, the P2RX2-specific inhibitory antibody exhibits one or more of the following activities: (a) disrupts cation channel flux; (b) disrupts extracellular ATP binding; (c) disrupts extracellular purinergic nucleotide binding; (d) sterically hinders binding of P2RX2 to a binding partner selected from the group consisting of P2RX1, P2RX3, P2RX4, P2RX5, P2RX6, and P2RX7; (e) induces antibody-dependent cell killing of the P2RX2-expressing cell; (f) induces phagocytosis of the P2RX2-expressing cell; (g) induces opsonization of the P2RX2-expressing cell; (h) induces downregulation of P2RX2; (i) prevents formation of homotrimers or heterotrimers containing P2RX2; (j) does not have agonistic activity; (k) antagonizes P2RX2; (l) binds to residue V60 or G353 of P2RX2; or (m) binds to or blocks one or more glycosylation sites at residues 133, 194, and 310 of P2RX2.

In some embodiments of any of the above aspects, the P2RX2 inhibitory antibody binds to a P2RX2 binding partner selected from the group consisting of P2RX1, P2RX3, P2RX4, P2RX5, P2RX6, and P2RX7 and exhibits one or more of the following activities: (a) sterically hinders binding of the binding partner to P2RX2; (b) binds to the P2RX2-binding site of the binding partner; (c) induces antibody-dependent cell killing of the binding partner-expressing cell; (d) induces phagocytosis of the binding partner-expressing cell; (e) induces opsonization of the binding partner-expressing cell; (f) induces downregulation of binding partner; (g) prevents formation of multimers (e.g., dimers or trimers) containing the binding partner; (h) does not have agonistic activity; or (i) antagonizes the binding partner.

In some embodiments of the above aspects, the composition further includes a second therapeutic agent.

In some embodiments of any of the above aspects, the composition further includes a pharmaceutically acceptable excipient.

In some embodiments of any of the above aspects, the second therapeutic agent is an anti-cancer therapeutic, a P2RX2 signaling inhibitor, a P2RX2 function blocker, a neurotransmission blocker, or a neuronal growth factor blocker.

In some embodiments of any of the above aspects, the anti-cancer therapeutic is a checkpoint inhibitor, a chemotherapeutic agent, a biologic cancer agent, an anti-angiogenic drug, a drug that targets cancer metabolism, an antibody that marks a cancer cell surface for destruction, an antibody-drug conjugate, a cell therapy, a commonly used anti-neoplastic agent, or a non-drug therapy.

In some embodiments of any of the above aspects, the checkpoint inhibitor is an inhibitory antibody, a fusion protein, an agent that interacts with a checkpoint protein, an agent that interacts with the ligand of a checkpoint protein, an inhibitor of CTLA-4, an inhibitor of PD-1, an inhibitor of PDL1, an inhibitor of PDL2, or an inhibitor of B7-H3, B7-H4, BTLA, HVEM, TIM3, GAL9, LAGS, VISTA, KIR, 2B4, CD160, CGEN-15049, CHK 1, CHK2, A2aR, or B-7 family ligands.

In some embodiments of any of the above aspects, the biologic cancer agent is an antibody listed in Table 3.

In some embodiments of any of the above aspects, the cancer is a cancer listed in column 1 of Table 4 and the second agent is a corresponding anti-cancer agent listed in column 2 of Table 4.

In some embodiments of any of the above aspects, the neurotransmission blocker is neurotoxin listed in Table 9, an antagonist of a neurotransmitter receptor listed in Table 5 or a neurotransmitter listed in Table 6, or a GABA re-uptake inhibitor, GABA analog, or GABA prodrug listed in Table 8. In some embodiments, the antagonist of a neurotransmitter receptor listed in Table 5 or a neurotransmitter listed in Table 6 is an antagonist listed in Tables 7A-7K.

In some embodiments of any of the above aspects, the neuronal growth factor blocker is an antagonist of a neuronal growth factor listed in Table 10. In some embodiments, the antagonist of a neuronal growth factor listed in Table 10 is an antibody listed in Table 11 or an antagonist listed in Table 12. In some embodiments, the antagonist of a neuronal growth factor listed in Table 10 is selected from the group consisting of etanercept, thalidomide, lenalidomide, pomalidomide, pentoxifylline, bupropion, DOI, disitertide, and trabedersen.

In some embodiments of any of the above aspects, the P2RX2 function blocker is a P2RX2-specific inhibitor. In some embodiments of any of the above aspects, the P2RX2 function blocker is a P2RX2-specific inhibitory antibody or an antigen binding fragment thereof. In some embodiments of any of the above aspects, the P2RX2 function blocker is an inhibitory RNA directed against P2RX2. In some embodiments of any of the above aspects, the P2RX2 function blocker is an inhibitory RNA directed against a P2RX2 binding partner selected from the group consisting of P2RX1, P2RX3, P2RX4, P2RX5, P2RX6, and P2RX7. In some embodiments of any of the above aspects, the P2RX2 function blocker is P2RX2 inhibitory antibody that binds to a P2RX2 binding partner selected from the group consisting of P2RX1, P2RX3, P2RX4, P2RX5, P2RX6, and P2RX7. In some embodiments of any of the above aspects, the P2RX2 function blocker is a small molecule inhibitor listed in Table 1. In some embodiments, the small molecule inhibitor is a P2RX2-specific inhibitor.

In some embodiments of any of the above aspects, the P2RX2 signaling inhibitor is a small molecule inhibitor that disrupts downstream calcium signaling. In some embodiments, the P2RX2 signaling inhibitor is a small molecule inhibitor listed in Table 2.

In some embodiments of any of the above aspects, the P2RX2 inhibitor or P2RX2-specific inhibitor is selected from the group consisting of an antibody, a small molecule, a polypeptide, a DNA molecule, an RNA molecule, a gRNA, and a viral vector. In some embodiments, the antibody is a P2RX2 inhibitory antibody or an antigen binding fragment thereof. In some embodiments, the P2RX2 inhibitory antibody is a P2RX2-specific inhibitory antibody or an antigen binding fragment thereof. In some embodiments, the P2RX2 inhibitory antibody binds to a P2RX2 binding partner selected from the group consisting of P2RX1, P2RX3, P2RX4, P2RX5, P2RX6, and P2RX7. In some embodiments, the RNA molecule is an inhibitory RNA directed to P2RX2. In some embodiments, the RNA molecule is an inhibitory RNA directed to a P2RX2 binding partner selected from the group consisting of P2RX1, P2RX3, P2RX4, P2RX5, P2RX6, and P2RX7. In some embodiments, the small molecule is a small molecule inhibitor listed in Table 1 or a P2RX2 signaling inhibitor listed in Table 2.

In some embodiments of any of the above aspects, the P2RX2 inhibitor or P2RX2-specific inhibitor does not cross the blood brain barrier. In some embodiments, the P2RX2 inhibitor or the P2RX2-specific inhibitor has been modified to prevent blood brain barrier crossing by conjugation to a targeting moiety, formulation in a particulate delivery system, addition of a molecular adduct, or through modulation of its size, polarity, flexibility, or lipophilicity.

In some embodiments of any of the above aspects, the P2RX2 inhibitor or P2RX2-specific inhibitor does not have a direct effect on the central nervous system or gut.

In some embodiments of any of the above aspects, the P2RX2 inhibitor or P2RX2 specific inhibitor decreases tumor volume, decreases tumor or cancer cell growth, decreases tumor innervation, decreases cancer cell proliferation, decreases cancer cell invasion, decreases cancer cell migration, decreases cancer cell metastasis, increases cancer cell death, increases cancer cell autophagy, increases, time to recurrence, or improves survival.

Definitions

As used herein, "administration" refers to providing or giving a subject a therapeutic agent (e.g., a P2RX2 inhibitor), by any effective route. Exemplary routes of administration are described herein below.

As used herein, the term "agonist" refers to an agent (e.g., a small molecule or antibody) that increases receptor activity. An agonist may activate a receptor by directly binding to the receptor, by acting as a cofactor, by modulating receptor conformation (e.g., maintaining a receptor in an open or active state). An agonist may increase receptor activity by 10%, 20%, 30%, 40%, 50%, 60%, 70%, 80%, 90%, 95%, 98% or more. An agonist may induce maximal receptor activation or partial activation depending on the concentration of the agonist and its mechanism of action.

As used herein, the term "analog" refers to a protein of similar nucleotide or amino acid composition or sequence to any of the proteins or peptides of the invention, allowing for variations that do not have an adverse effect on the ability of the protein or peptide to carry out its normal function (e.g., bind to a receptor or promote synapse formation). Analogs may be the same length, shorter, or longer than their corresponding protein or polypeptide. Analogs may have about 60% (e.g., about 60%, about 62%, about 64%, about 66%, about 68%, about 70%, about 72%, about 74%, about 76%, about 78%, about 80%, about 82%, about 84%, about 86%, about 88%, about 90%, about 92%, about 94%, about 96%, about 98%, or about 99%) identity to the amino acid sequence of the naturally occurring protein or peptide. An analog can be a naturally occurring protein or polypeptide sequence that is modified by deletion, addition, mutation, or substitution of one or more amino acid residues.

As used herein, the term "antagonist" refers to an agent (e.g., a small molecule or antibody) that reduces or inhibits receptor activity. An antagonist may reduce receptor activity by directly binding to the receptor, by blocking the receptor binding site, by modulating receptor conformation (e.g., maintaining a receptor in a closed or inactive state). An antagonist may reduce receptor activity by 10%, 20%, 30%, 40%, 50%, 60%, 70%, 80%, 90%, 95%, 98% or more. An antagonist may also completely block or inhibit receptor activity. Antagonist activity may be concentration-dependent or -independent.

As used herein, the term "antibody" refers to a molecule that specifically binds to, or is immunologically reactive with, a particular antigen and includes at least the variable domain of a heavy chain, and normally includes at least the variable domains of a heavy chain and of a light chain of an immunoglobulin. Antibodies and antigen-binding fragments, variants, or derivatives thereof include, but are not limited to, polyclonal, monoclonal, multispecific, human, humanized, primatized, or chimeric antibodies, heteroconjugate antibodies (e.g., bi- tri- and quad-specific antibodies, diabodies, triabodies, and tetrabodies), single-domain antibodies (sdAb), epitope-binding fragments, e.g., Fab, Fab' and F(ab')$_2$, Fd, Fvs, single-chain Fvs (scFv), rIgG, single-chain antibodies, disulfide-linked Fvs (sdFv), fragments including either a $V_L$ or $V_H$ domain, fragments produced by an Fab expression library, and anti-idiotypic (anti-Id) antibodies. Antibody molecules of the invention can be of any type (e.g., IgG, IgE, IgM, IgD, IgA, and IgY), class (e.g., IgG1, IgG2, IgG3, IgG4, IgA1 and IgA2) or subclass of immunoglobulin molecule. Moreover, unless otherwise indicated, the term "monoclonal antibody" (mAb) is meant to include both intact molecules as well as antibody fragments (such as, for example, Fab and F(ab')$_2$ fragments) that are capable of specifically binding to a target protein. Fab and F(ab')$_2$ fragments lack the Fc fragment of an intact antibody.

The term "antigen-binding fragment," as used herein, refers to one or more fragments of an immunoglobulin that retain the ability to specifically bind to a target antigen. The antigen-binding function of an immunoglobulin can be performed by fragments of a full-length antibody. The antibody fragments can be a Fab, F(ab')$_2$, scFv, SMIP, diabody, a triabody, an affibody, a nanobody, an aptamer, or a domain antibody. Examples of binding fragments encompassed by the term "antigen-binding fragment" of an antibody include, but are not limited to: (i) a Fab fragment, a monovalent fragment consisting of the $V_L$, $V_H$, $C_L$, and $C_H1$ domains; (ii) a F(ab')$_2$ fragment, a bivalent fragment including two Fab fragments linked by a disulfide bridge at the hinge region; (iii) a Fd fragment consisting of the $V_H$ and $C_H1$ domains; (iv) a Fv fragment consisting of the $V_L$ and $V_H$ domains of a single arm of an antibody, (v) a dAb (Ward et al., Nature 341:544-546, 1989) including $V_H$ and $V_L$ domains; (vi) a dAb fragment that consists of a $V_H$ domain; (vii) a dAb that consists of a $V_H$ or a $V_L$ domain; (viii) an isolated complementarity determining region (CDR); and (ix) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a linker that enables them to be made as a single protein chain in which the $V_L$ and $V_H$ regions pair to form monovalent molecules (known as single chain Fv (scFv)). These antibody fragments can be obtained using conventional techniques known to those of skill in the art, and the fragments can be screened for utility in the same manner as intact antibodies. Antigen-binding fragments can be produced by recombinant DNA techniques, enzymatic or chemical cleavage of intact immunoglobulins, or, in certain cases, by chemical peptide synthesis procedures known in the art.

As used herein, the term "binding partner" refers to a polypeptide or fragment thereof that binds to a protein of interest (e.g., P2RX2). Binding partners include receptors and other molecules that selectively bind to the ligand of interest. Exemplary P2RX2 binding partners are P2RX1, P2RX3, P2RX4, P2RX5, P2RX6, and P2RX7.

As used herein, the term "cell type" refers to a group of cells sharing a phenotype that is statistically separable based on gene expression data. For instance, cells of a common cell type may share similar structural and/or functional characteristics, such as similar gene activation patterns and antigen presentation profiles. Cells of a common cell type may include those that are isolated from a common tissue (e.g., epithelial tissue, neural tissue, connective tissue, or muscle tissue) and/or those that are isolated from a common organ, tissue system, blood vessel, or other structure and/or region in an organism.

As used herein, a "combination therapy" or "administered in combination" means that two (or more) different agents or treatments are administered to a subject as part of a defined treatment regimen for a particular disease or condition. The treatment regimen defines the doses and periodicity of administration of each agent such that the effects of the separate agents on the subject overlap. In some embodiments, the delivery of the two or more agents is simultaneous or concurrent and the agents may be co-formulated. In other embodiments, the two or more agents are not co-formulated and are administered in a sequential manner as part of a prescribed regimen. In some embodiments, administration of two or more agents or treatments in combination is such that the reduction in a symptom, or other parameter related to the disorder is greater than what would be observed with one agent or treatment delivered alone or in the absence of the other. The effect of the two treatments can be partially additive, wholly additive, or greater than additive (e.g., synergistic). Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination may be administered by intravenous injection while a second therapeutic agent of the combination may be administered orally.

As used herein, the terms "effective amount," "therapeutically effective amount," and a "sufficient amount" of a composition, antibody, vector construct, viral vector or cell described herein refer to a quantity sufficient to, when administered to a subject, including a mammal (e.g., a human), effect beneficial or desired results, including effects at the cellular level, tissue level, or clinical results, and, as such, an "effective amount" or synonym thereto depends upon the context in which it is being applied. For example, in the context of treating cancer it is an amount of the composition, antibody, vector construct, viral vector or cell sufficient to achieve a treatment response as compared to the response obtained without administration of the composition, antibody, vector construct, viral vector or cell. The amount of a given composition described herein that will correspond to such an amount will vary depending upon various factors, such as the given agent, the pharmaceutical formulation, the route of administration, the type of disease or disorder, the identity of the subject (e.g., age, sex, weight) or host being treated, and the like, but can nevertheless be routinely determined by one skilled in the art. Also, as used herein, a "therapeutically effective amount" of a composition, antibody, vector construct, viral vector or cell of the present disclosure is an amount that results in a beneficial or desired result in a subject as compared to a control. As defined herein, a therapeutically effective amount of a composition, antibody, vector construct, viral vector or cell of the present disclosure may be readily determined by one of ordinary skill by routine methods known in the art. Dosage regimen may be adjusted to provide the optimum therapeutic response.

As used herein, the terms "increasing" and "decreasing" refer to modulating resulting in, respectively, greater or lesser amounts, of function, expression, or activity of a metric relative to a reference. For example, subsequent to administration of a P2RX2 inhibitor in a method described herein, the amount of a marker of a metric (e.g., cancer cell death) as described herein may be increased or decreased in a subject by at least 5%, 10%, 15%, 20%, 25%, 30%, 35%, 40%, 45%, 50%, 55%, 60%, 65%, 70%, 75%, 80%, 85%, 90%, 95% or 98% or more relative to the amount of the marker prior to administration. Generally, the metric is measured subsequent to administration at a time that the administration has had the recited effect, e.g., at least one week, one month, 3 months, or 6 months, after a treatment regimen has begun.

As used herein, the term "innervated" refers to a tissue (e.g., a tumor) that contains nerves. "Innervation" refers to the process of nerves entering a tissue.

As used herein, "locally" or "local administration" means administration at a particular site of the body intended for a local effect and not a systemic effect. Examples of local administration are epicutaneous, inhalational, intra-articular, intrathecal, intravaginal, intravitreal, intrauterine, intra-lesional administration, lymph node administration, intratumoral administration and administration to a mucous membrane of the subject, wherein the administration is intended to have a local and not a systemic effect.

As used herein, the term "percent (%) sequence identity" refers to the percentage of amino acid (or nucleic acid) residues of a candidate sequence that are identical to the amino acid (or nucleic acid) residues of a reference sequence after aligning the sequences and introducing gaps, if necessary, to achieve the maximum percent sequence identity (e.g., gaps can be introduced in one or both of the candidate and reference sequences for optimal alignment and non-homologous sequences can be disregarded for comparison purposes). Alignment for purposes of determining percent sequence identity can be achieved in various ways that are within the skill in the art, for instance, using publicly available computer software, such as BLAST, ALIGN, or Megalign (DNASTAR) software. Those skilled in the art can determine appropriate parameters for measuring alignment, including any algorithms needed to achieve maximal alignment over the full length of the sequences being compared. For example, a reference sequence aligned for comparison with a candidate sequence may show that the candidate sequence exhibits from 50% to 100% sequence identity across the full length of the candidate sequence or a selected portion of contiguous amino acid (or nucleic acid) residues of the candidate sequence. The length of the candidate sequence aligned for comparison purposes may be, for example, at least 30%, (e.g., 30%, 40, 50%, 60%, 70%, 80%, 90%, or 100%) of the length of the reference sequence. When a position in the candidate sequence is occupied by the same amino acid residue as the corresponding position in the reference sequence, then the molecules are identical at that position.

As used herein, a "pharmaceutical composition" or "pharmaceutical preparation" is a composition or preparation having pharmacological activity or other direct effect in the mitigation, treatment, or prevention of disease, and/or a finished dosage form or formulation thereof and which is indicated for human use.

As used herein, the term "pharmaceutically acceptable" refers to those compounds, materials, compositions and/or dosage forms, which are suitable for contact with the tissues of a subject, such as a mammal (e.g., a human) without excessive toxicity, irritation, allergic response and other problem complications commensurate with a reasonable benefit/risk ratio.

As used herein, the term "proliferation" refers to an increase in cell numbers through growth and division of cells.

As used herein, the term "reference" refers to a level, expression level, copy number, sample or standard that is used for comparison purposes. For example, a reference sample can be obtained from a healthy individual (e.g., an individual who does not have cancer). A reference level can be the level of expression of one or more reference samples. For example, an average expression (e.g., a mean expression or median expression) among a plurality of individuals (e.g., healthy individuals, or individuals who do not have cancer). In other instances, a reference level can be a predetermined threshold level, e.g., based on functional expression as otherwise determined, e.g., by empirical assays.

As used herein, the term "sample" refers to a specimen (e.g., blood, blood component (e.g., serum or plasma), urine, saliva, amniotic fluid, cerebrospinal fluid, tissue (e.g., placental or dermal), pancreatic fluid, chorionic villus sample, and cells) isolated from a subject.

As used herein, the terms "subject" and "patient" refer to an animal (e.g., a mammal, such as a human). A subject to be treated according to the methods described herein may be one who has been diagnosed with a particular condition, or one at risk of developing such conditions. Diagnosis may be performed by any method or technique known in the art. One skilled in the art will understand that a subject to be treated according to the present disclosure may have been subjected to standard tests or may have been identified, without examination, as one at risk due to the presence of one or more risk factors associated with the disease or condition.

"Treatment" and "treating," as used herein, refer to the medical management of a subject with the intent to improve, ameliorate, stabilize (i.e., not worsen), prevent or cure a disease, pathological condition, or disorder. This term includes active treatment (treatment directed to improve the disease, pathological condition, or disorder), causal treatment (treatment directed to the cause of the associated disease, pathological condition, or disorder), palliative treatment (treatment designed for the relief of symptoms), preventative treatment (treatment directed to minimizing or partially or completely inhibiting the development of the associated disease, pathological condition, or disorder); and supportive treatment (treatment employed to supplement another therapy). Treatment also includes diminishment of the extent of the disease or condition; preventing spread of the disease or condition; delay or slowing the progress of the disease or condition; amelioration or palliation of the disease or condition; and remission (whether partial or total), whether detectable or undetectable. "Ameliorating" or "palliating" a disease or condition means that the extent and/or undesirable clinical manifestations of the disease, disorder, or condition are lessened and/or time course of the progression is slowed or lengthened, as compared to the extent or time course in the absence of treatment. "Treatment" can also mean prolonging survival as compared to expected survival if not receiving treatment. Those in need of treatment include those already with the condition or disorder, as well as those prone to have the condition or disorder or those in which the condition or disorder is to be prevented.

As used herein, the term "overexpressed" refers to a nucleic acid or polypeptide that is expressed or caused to be expressed or produced in a cell at a greater level than is normally expressed in the corresponding wild-type cell. For example, P2RX2 is "overexpressed" in a cancer cell when P2RX2 is present at a higher level in the cancer cell compared to the level in a non-cancerous cell of the same tissue or cell type from the same species or individual. P2RX2 is overexpressed when P2RX2 expression is increased by 1.1-fold or more (e.g., 1.1, 1.2, 1.3, 1.4, 1.5, 2.0, 2.5, 3.0, 3.5, 4.0, 4.5, 5.0, 6.0, 7.0, 8.0, 9.0, 10.0-fold or more) compared to a reference (e.g., a non-cancerous cell of the same type).

As used herein, the term "cancer" refers to a condition characterized by unregulated or abnormal cell growth. The terms "cancer cell," "tumor cell," and "tumor" refer to an abnormal cell, mass, or population of cells that result from excessive division that may be malignant or benign and all pre-cancerous and cancerous cells and tissues.

As used herein, the term "P2RX2-associated cancer" refers to a cancer in which P2RX2 is expressed (e.g., a cancer in which P2RX2 is overexpressed compared to a reference (e.g., a non-cancerous cell of the same type), or a cancer in which P2RX2 is mutated (e.g., a cancer carrying an activating P2RX2 mutation, e.g., a cancer expressing hyperactive P2RX2)). P2RX2-associated cancers can be identified by assessing a cancer cell or tumor sample for P2RX2 gene or protein expression and comparing it to P2RX2 gene or protein expression in a reference cell.

The term "P2RX2 inhibitory antibody" refers to antibodies that are capable of binding to P2RX2 or a P2RX2 binding partner selected from the group consisting of P2RX1, P2RX3, P2RX4, P2RX5, P2RX6, and P2RX7, and inhibiting or reducing P2RX2 function and/or attenuating one or more signal transduction pathways mediated by P2RX2. For example, P2RX2 inhibitory antibodies may disrupt cation channel flux or extracellular ATP binding, prevent P2RX2 from binding to P2RX3 or other P2RX2 binding partners, or block the formation of homotrimers or heterotrimers containing P2RX2. The term "P2RX2-specific inhibitory antibody" refers to antibodies that bind specifically to P2RX2 (e.g., antibodies that do not bind to other P2RX family members) and inhibit or reduce P2RX2 function and/or attenuate one or more signal transduction pathways mediated by P2RX2. P2RX2 inhibitory antibodies and P2RX2-specific inhibitory antibodies inhibit or reduce P2RX2 function and/or attenuate one or more P2RX2-mediated signal transduction pathways by at least 10% (e.g., 10%, 20%, 30%, 40%, 50%, 60%, 70%, 80%, 90%, 95%, 98% or more).

As used herein, the term "P2RX2 inhibitor" refers to an agent that inhibits or reduces P2RX2 function or signaling. P2RX2 inhibitors include P2RX2 inhibitory antibodies, small molecules, or inhibitory RNAs that reduce or inhibit P2RX2 expression, P2RX2 binding, P2RX2 function, or signal transduction downstream of P2RX2. P2RX2 inhibitors reduce P2RX2 function or signaling by 10% or more (e.g., 10%, 20%, 30%, 40%, 50%, 60%, 70%, 80%, 90%, 95%, 98% or more).

As used herein, the term "P2RX2-specific inhibitor" refers to a P2RX2 inhibitor that selectively inhibits or reduces P2RX2 function or signaling without substantially affecting the function or signaling of any other protein (e.g., without substantially affecting the function or signaling of P2RX1, P2RX3, P2RX4, P2RX5, P2RX6, and P2RX7). P2RX2-specific inhibitors include P2RX2-specific inhibitory antibodies, inhibitory RNAs directed to P2RX2, and P2RX2-specific small molecule inhibitors. P2RX2-specific inhibitors reduce P2RX2 function or signaling by 10% or more (e.g., 10%, 20%, 30%, 40%, 50%, 60%, 70%, 80%, 90%, 95%, 98% or more).

As used herein, the term "P2RX2 function blocker" refers to a type of P2RX2 inhibitor that reduces or inhibits P2RX2 function by reducing the expression of P2RX2 or preventing P2RX2 from interacting with one or more of its binding partners (e.g., other P2RX family members). Exemplary P2RX2 function blockers include antibodies that bind to the extracellular domain of P2RX2, inhibitory RNAs directed to P2RX2 or a P2RX2 binding partner, P2RX2 small molecule inhibitors, and antibodies that bind to one or more P2RX2 binding partners (e.g., antibodies that bind to the extracellular domains of P2RX1, P2RX3, P2RX4, P2RX5, P2RX6, and P2RX7 and block their interaction with P2RX2). P2RX2 function blockers reduce P2RX2 function by 10% or more (e.g., 10%, 20%, 30%, 40%, 50%, 60%, 70%, 80%, 90%, 95%, 98% or more).

As used herein, the term "P2RX2 signaling inhibitor" refers to a type of P2RX2 inhibitor that reduces or inhibits the intracellular signaling that is downstream of P2RX2 activation or interaction with a binding partner. Exemplary P2RX2 signaling inhibitors include small molecules that inhibit intracellular calcium signaling. P2RX2 signaling inhibitors reduce downstream signaling by 10% or more (e.g., 10%, 20%, 30%, 40%, 50%, 60%, 70%, 80%, 90%, 95%, 98% or more).

As used herein, an agent that "does not cross the blood brain barrier" is an agent that does not significantly cross the barrier between the peripheral circulation and the brain and spinal cord. This can also be referred to as a "blood brain barrier impermeable" agent. Agents will have a limited ability to cross the blood brain barrier if they are not lipid soluble or have a molecular weight of over 600 Daltons.

Agents that typically cross the blood brain barrier can be modified to become blood brain barrier impermeable based on chemical modifications that increase the size or alter the hydrophobicity of the agent, packaging modifications that reduce diffusion (e.g., packaging an agent within a microparticle or nanoparticle), and conjugation to biologics that direct the agent away from the blood brain barrier (e.g., conjugation to a pancreas-specific antibody). An agent that does not cross the blood brain barrier is an agent for which 30% or less (e.g., 30%, 25%, 20%, 15%, 10%, 5%, 2% or less) of the administered agent crosses the blood brain barrier.

As used herein, an agent that "does not have a direct effect on the central nervous system (CNS) or gut" is an agent that does not directly alter neurotransmission, neuronal numbers, or neuronal morphology in the CNS or gut when administered according to the methods described herein. This may be assessed by administering the agents to animal models and performing electrophysiological recordings or immunohistochemical analysis. An agent will be considered not to have a direct effect on the CNS or gut if administration according to the methods described herein has an effect on neurotransmission, neuronal numbers, or neuronal morphology in the CNS or gut that is 50% or less (e.g., 50%, 45%, 40%, 35%, 30%, 25%, 20%, 15%, 10%, 5%, or less) of the effect observed if the same agent is administered directly to the CNS or gut.

As used herein, the term "neuronal growth factor blocker" refers to an agent that decreases or inhibits neuronal growth, development, or survival. Neuronal growth factors include proteins that promote neurogenesis, neuronal growth, and neuronal differentiation (e.g., neurotrophic factors NGF, NT3, BDNF, CNTF, and GDNF), proteins that promote neurite outgrowth (e.g., axon or dendrite outgrowth or stabilization), or proteins that promote synapse formation (e.g., synaptogenesis, synapse assembly, synaptic adhesion, synaptic maturation, synaptic refinement, or synaptic stabilization). These processes lead to innervation of tissue, including neural tissue, muscle, and tumors, and the formation of synaptic connections between two or more neurons and between neurons and non-neural cells (e.g., tumor cells). A neuronal growth factor blocker reduces or inhibits one or more of these processes (e.g., through the use of antibodies that block neuronal growth factors or their receptors). Exemplary neuronal growth factors are listed in Table 10. Neuronal growth factor blockers decrease or inhibit neurite outgrowth, innervation, synapse formation, or any of the aforementioned processes by 10% or more (e.g., 10%, 20%, 30%, 40%, 50%, 60%, 70%, 80%, 90%, 95%, 98% or more).

As used herein, the term "neurotransmission blocker" refers to an agent that decreases or blocks neurotransmission. Neurotransmission blockers can decrease neurotransmission by 10%, 20%, 30%, 40%, 50%, 60%, 70%, 80%, 90%, 95%, 98% or more. Exemplary neurotransmitters and neurotransmitter receptors are listed in Tables 5 and 6. Neurotransmission blockers may decrease neurotransmission by decreasing neurotransmitter synthesis or release, increasing neurotransmitter reuptake or degradation, decreasing neurotransmitter receptor activity, decreasing neurotransmitter receptor synthesis or membrane insertion, increasing neurotransmitter degradation, regulating neurotransmitter receptor conformation, and disrupting the pre- or postsynaptic machinery. Neurotransmission blockers include antibodies that bind to or block the function of neurotransmitters, neurotransmitter receptor antagonists, inhibitory RNAs directed to neurotransmitter receptors, and toxins that disrupt synaptic release.

DETAILED DESCRIPTION

Described herein are compositions and methods for the treatment of cancer in a subject (e.g., a mammalian subject, such as a human) by administering purinergic receptor P2X2 (P2RX2) inhibitors. P2RX2 inhibitors include inhibitors specific to P2RX2 (e.g., anti-P2RX2-specific inhibitory antibodies) and non-specific inhibitors that could potentially affect other proteins due to their having shared binding partners or signaling pathways with P2RX2. These methods and compositions provide new mechanistic approaches for treating cancer.

P2RX2

P2RX2 (Entrez Gene ID 22953) is a transmembrane purinergic receptor gated by extracellular ATP. This ligand-gated ion channel is a non-selective cation channel that is involved in a number of neuronal functions, such as synaptic transmission between neurons and from neurons to smooth muscle, neuromuscular junction formation, hearing, and taste perception. P2RX2 forms a trimer, which can be composed of three P2RX2 molecules (a homotrimer) or P2RX2 and two other P2RX receptors (a heterotrimer). P2X receptors are expressed by neurons and glial cells throughout the central and peripheral nervous system.

The present invention relates to the discovery that loss of P2RX2 in pancreatic cancer cell lines prevented tumor growth when P2RX2 knockout cancer cells were implanted in mice. These findings indicate that inhibition of P2RX2 can be used as a therapeutic strategy for treating pancreatic cancer and other cancers. These data also suggest that patients with overexpression of P2RX2 are at increased risk of developing cancer and would benefit from specific treatments, such as treatment with the compositions and methods described herein.

P2RX2 Inhibitors

P2RX2 inhibitors described herein can reduce or inhibit P2RX2 function or signaling in order to treat cancer. P2RX2 inhibitors can be grouped into categories based on their mechanism of action and their effect on P2RX2: 1) P2RX2-specific inhibitors (e.g., inhibitors that only disrupt P2RX2 function or signaling, such as P2RX2-specific inhibitory antibodies, P2RX2-specific small molecule inhibitors, or inhibitory RNA directed to P2RX2), 2) P2RX2 function blockers (e.g., inhibitors that prevent P2RX2 from binding to a binding partner, forming trimers, or carrying out other processes necessary for normal P2RX2 activity, e.g., P2RX2 inhibitory antibodies, such as anti-P2X family member (e.g., P2RX1, 3, 4, 5, 6, or 7) antibodies, and 3) P2RX2 signaling inhibitors (e.g., inhibitors that disrupt downstream signaling pathways or intracellular events that occur after activation of P2RX2).

P2RX2-Specific Inhibitors

In some embodiments, the P2RX2 inhibitor is a P2RX2-specific inhibitor. P2RX2-specific inhibitors selectively reduce or inhibit P2RX2 function, expression, or signaling without directly affecting other proteins. P2RX2-specific inhibitors include P2RX2-specific inhibitory antibodies or antigen binding fragments thereof, inhibitory RNAs directed to P2RX2, and small molecules that specifically bind to and inhibit P2RX2 (e.g., P2RX2-specific small molecule inhibitors listed in Table 1). P2RX2-specific inhibitors can reduce P2RX2 function, expression, or signaling by 5% or more (e.g., 5%, 10%, 15%, 20%, 25%, 30%, 40%, 50%, 60%, 70%, 80%, 90%, 95%, 99%, or more).

In some embodiments, the P2RX2 antibody is a P2RX2-specific inhibitory antibody or an antigen binding fragment thereof that binds to P2RX2 and reduces or inhibits P2RX2 function. P2RX2-specific inhibitory antibodies include antibodies having one or more of the following functional properties: prevent P2RX2 from binding to a binding partner (e.g., sterically hinder the binding of P2RX2 to a binding partner selected from the group consisting of P2RX1, P2RX3, P2RX4, P2RX5, P2RX6, and P2RX7); reduce or inhibit cation channel flux; reduce or inhibit extracellular ATP binding; reduce or inhibit extracellular purinergic nucleotide binding; do not have agonistic activity (e.g., do not activate P2RX2); induce antibody-dependent cell killing of the cell expressing P2RX2 (e.g., antibody-dependent cell killing by Natural Killer (NK) cells, monocytes, macrophages, neutrophils, dendritic cells, or eosinophils); induce phagocytosis of the cell expressing P2RX2 (e.g., macrophage phagocytosis of the cancer cell); induce opsonization of the cell expressing P2RX2; prevent the formation of homotrimers or heterotrimers containing P2RX2 (e.g., the antibody is a monovalent antibody or an antibody with a single heavy chain); induce downregulation of P2RX2 on the cell surface (e.g., hyper-crosslink or cluster P2RX2 to induce internalization and degradation, e.g., the antibody is a polyvalent antibody); or antagonize P2RX2. In some embodiments, P2RX2 inhibitory antibodies have one or more of the following properties: bind to residue V60 or G353 of P2RX2, or bind to or block one or more glycosylation sites at residues 133, 194, and 310 of P2RX2. Antibodies having one or more of these functional properties are routinely screened and selected once the desired functional property is identified herein (e.g., by screening of phage display or other antibody libraries).

In some embodiments, the P2RX2-specific inhibitor is an inhibitory RNA directed to P2RX2. In some embodiments, the P2RX2 inhibitor is a small molecule inhibitor (e.g., antagonist) that is selective for P2RX2. P2RX2-specific small molecule inhibitors for use in the compositions and methods described herein are listed in Table 1.

P2RX2 Function Blockers

In some embodiments, the P2RX2 inhibitor is a P2RX2 function blocker. P2RX2 function blockers reduce or inhibit P2RX2 function by reducing P2RX2 expression, preventing P2RX2 from interacting with its binding partners (e.g., P2RX1, P2RX3, P2RX4, P2RX5, P2RX6, or P2RX7), or preventing P2RX2 from becoming activated. P2RX2 function blockers include P2RX2-specific inhibitors that reduce or inhibit P2RX2 function or expression (e.g., P2RX2-specific inhibitory antibodies or antigen binding fragments thereof, inhibitory RNAs directed against P2RX2, small molecule inhibitors that are specific for P2RX2), P2RX2 inhibitory antibodies that bind to P2RX2 binding partners or antigen binding fragments thereof (e.g., antibodies that bind to P2RX1, P2RX3, P2RX4, P2RX5, P2RX6, or P2RX7 and block their interaction with P2RX2), inhibitory RNAs directed to P2RX2 binding partners, and small molecule inhibitors that non-specifically reduce or inhibit the function of P2RX2 (e.g., small molecule inhibitors of the P2X receptor family).

P2RX2 binding partners include P2RX1 (Entrez Gene ID 5023), P2RX3 (Entrez Gene ID 5024), P2RX4 (Entrez Gene ID 5025), P2RX5 (Entrez Gene ID 5026), P2RX6 (Entrez Gene ID 9127), and P2RX7 (Entrez Gene ID 5027).

In some embodiments, P2RX2 inhibitory antibodies that bind to P2RX2 binding partners are antibodies that bind to P2RX1, P2RX3, P2RX4, P2RX5, P2RX6, or P2RX7. In some embodiments, P2RX2 inhibitory antibodies that bind to P2RX2 binding partners have one or more of the following functional properties: sterically hinders the binding partner from binding to P2RX2 (e.g., blocks the interaction between P2RX2 and P2RX1, P2RX3, P2RX4, P2RX5, P2RX6, or P2RX7); binds to the P2RX2 binding site on the binding partner; antagonizes the binding partner (e.g., prevents binding partner signaling or prevents formation of multimers (e.g., dimers or trimers) containing the binding partner or containing the binding partner and P2RX2 (e.g., the antibody is monovalent and can only bind to one binding partner and cannot induce multimerization); induces binding partner downregulation on the cell surface (e.g., hyper-crosslinks the binding partner to induce internalization, e.g., the antibody is a polyvalent antibody); induces antibody-dependent cell killing of the binding partner-expressing cell (e.g., antibody-dependent cell killing by NK cells, monocytes, macrophages, neutrophils, dendritic cells, or eosinophils); induces phagocytosis of the binding partner-expressing cell (e.g., macrophage phagocytosis of the cancer cell); induces opsonization of the binding partner-expressing cell; or does not have agonistic activity (e.g., does not activate the binding partner). Antibodies having one or more of these functional properties are routinely screened and selected once the desired functional property is identified herein (e.g., by screening of phage display or other antibody libraries).

In some embodiments, the P2RX2 function blocker is an inhibitory RNA directed to a P2RX2 binding partner selected from the group consisting of P2RX1, P2RX3, P2RX4, P2RX5, P2RX6, and P2RX7. In some embodiments, the P2RX2 function blocker is a small molecule signaling inhibitor listed in Table 1 (e.g. a P2RX2/P2RX3 heterotrimer inhibitor).

P2RX2 Signaling Inhibitors

In some embodiments, the P2RX2 inhibitor is a P2RX2 signaling inhibitor. P2RX2 signaling inhibitors include agents that reduce or inhibit signaling that occurs downstream of P2RX2 activation or binding to a binding partner, such as small molecule inhibitors of intracellular signaling cascades. P2RX2 signaling inhibitors include small molecules that disrupt intracellular calcium signaling (e.g., Ned K, A23187, BAPTA, or Dantrolene). Small molecule P2RX2 signaling inhibitors for use in the methods and compositions described herein are listed in Table 2.

TABLE 1

SMALL MOLECULE INHIBITORS OF P2RX2

| Type of Inhibitor | Inhibitors | | | |
|---|---|---|---|---|
| P2RX2-specific inhibitors (IC50 <10 µM) | CHEMBL494161 CHEMBL495204 CHEMBL523173 CHEMBL492300 CHEMBL494159 CHEMBL494353 CHEMBL494160 CHEMBL494158 CHEMBL526307 CHEMBL492934 CHEMBL492933 CHEMBL494582 CHEMBL492907 CHEMBL492703 CHEMBL1672104 CHEMBL495203 CHEMBL1672105 CHEMBL448525 CHEMBL271672 CHEMBL496401 CHEMBL413145 CHEMBL119180 CHEMBL502618 CHEMBL444469 CHEMBL1672106 CHEMBL493741 CHEMBL443930 CHEMBL492935 CHEMBL492745 | CHEMBL119416 CHEMBL499580 CHEMBL1672107 CHEMBL523043 CHEMBL521983 CHEMBL500550 CHEMBL492299 CHEMBL504607 CHEMBL494176 CHEMBL493547 CHEMBL493546 CHEMBL446310 CHEMBL69727 CHEMBL331358 CHEMBL494833 CHEMBL509572 CHEMBL496030 CHEMBL1671995 CHEMBL523000 CHEMBL492968 CHEMBL271688 CHEMBL494581 CHEMBL445413 CHEMBL331250 CHEMBL492967 CHEMBL492744 CHEMBL606414 CHEMBL604300 | CHEMBL604158 CHEMBL598857 CHEMBL597820 CHEMBL597591 CHEMBL597203 CHEMBL596982 CHEMBL524284 CHEMBL524064 CHEMBL522725 CHEMBL522053 CHEMBL521709 CHEMBL499428 CHEMBL498038 CHEMBL496229 CHEMBL496022 CHEMBL495834 CHEMBL495796 CHEMBL450832 CHEMBL404659 CHEMBL404450 CHEMBL403051 CHEMBL402239 CHEMBL256864 CHEMBL256688 CHEMBL256057 CHEMBL1672103 CHEMBL1672102 CHEMBL1672099 | CHEMBL1672098 CHEMBL1671997 CHEMBL1671996 CHEMBL1671993 CHEMBL1671992 CHEMBL134193 CHEMBL133576 CHEMBL131271 CHEMBL118007 CHEMBL116926 CHEMBL492729 CHEMBL521820 CHEMBL494940 CHEMBL492789 CHEMBL69234 CHEMBL401735 CHEMBL494834 CHEMBL494832 CHEMBL494772 CHEMBL494181 CHEMBL257495 CHEMBL117766 CHEMBL495195 CHEMBL493740 CHEMBL492562 CHEMBL477339 CHEMBL265502 CHEMBL522184 |
| P2RX2/P2RX3 heterotrimer inhibitors | CHEMBL3717153 CHEMBL3731399 CHEMBL3728821 CHEMBL3732843 CHEMBL3730913 CHEMBL3731410 CHEMBL3729264 CHEMBL3732909 CHEMBL3727382 CHEMBL3732309 CHEMBL3731936 CHEMBL3731366 CHEMBL3731764 CHEMBL3717395 CHEMBL3728949 CHEMBL3733189 CHEMBL3732959 CHEMBL3730584 CHEMBL3731980 CHEMBL3733173 CHEMBL3728301 CHEMBL3718959 CHEMBL3732382 | CHEMBL3729278 CHEMBL3730477 CHEMBL3730649 CHEMBL3733102 CHEMBL3729724 CHEMBL3731231 CHEMBL3730174 CHEMBL3731419 CHEMBL3729891 CHEMBL3730205 CHEMBL3730868 CHEMBL3729489 CHEMBL3732409 CHEMBL3729478 CHEMBL3731744 CHEMBL3731305 CHEMBL3732414 CHEMBL3732154 CHEMBL3733209 CHEMBL3732768 CHEMBL3727897 CHEMBL3729611 CHEMBL3727954 | CHEMBL3732185 CHEMBL3728501 CHEMBL3729987 CHEMBL3729871 CHEMBL3732208 CHEMBL3728453 CHEMBL3732421 CHEMBL3731986 CHEMBL3728126 CHEMBL3732353 CHEMBL3732671 CHEMBL3731191 CHEMBL3727749 CHEMBL3730212 CHEMBL3730748 CHEMBL3728853 CHEMBL3728157 CHEMBL3732341 CHEMBL3731610 CHEMBL3728519 CHEMBL3728605 CHEMBL3732062 CHEMBL3729325 | CHEMBL3728833 CHEMBL3727542 CHEMBL3730896 CHEMBL3731357 CHEMBL3731248 CHEMBL3731731 CHEMBL3730650 CHEMBL3728033 CHEMBL3728818 CHEMBL3730941 CHEMBL3727639 CHEMBL3729851 CHEMBL3731921 CHEMBL3729135 CHEMBL3732239 CHEMBL3733326 CHEMBL3729654 CHEMBL3731805 CHEMBL3731729 CHEMBL3730253 CHEMBL3730371 CHEMBL3731465 |

TABLE 2

SMALL MOLECULE INHIBITORS OF CALCIUM SIGNALING

| Signaling Pathway | Inhibitors |
|---|---|
| Calcium signaling | Ned K, A23187, BAPTA, Dantrolene, DHBP dibromide, EGTA, ionomycin, MDL 12330A, MRS 1845, Ned 19 (cis- or trans-), NPC 15199, ruthenium red, ryanodine, SKF 96365, (-)-Xestospongin C, YM 58483 |

Agent Modalities

A P2RX2 inhibitor can be selected from a number of different modalities. A P2RX2 inhibitor can be a nucleic acid molecule (e.g., DNA molecule or RNA molecule, e.g., mRNA or inhibitory RNA molecule (e.g., siRNA, shRNA, or miRNA), or a hybrid DNA-RNA molecule), a small molecule (e.g., a small molecule P2RX2 inhibitor, an inhibitor of a signaling cascade (e.g., calcium signaling), or an epigenetic modifier), or a polypeptide (e.g., an antibody molecule, e.g., an antibody or antigen binding fragment thereof). A P2RX2 inhibitor can also be a viral vector expressing a P2RX2 inhibitor or a cell infected with a viral vector. Any of these modalities can be a P2RX2 inhibitor directed to target (e.g., to reduce or inhibit) P2RX2 function, P2RX2 expression, P2RX2 binding, or P2RX2 signaling.

The nucleic acid molecule, small molecule, peptide, polypeptide, or antibody molecule can be modified. For example, the modification can be a chemical modification, e.g., conjugation to a marker, e.g., fluorescent marker or a radioactive marker. In other examples, the modification can include conjugation to a molecule that enhances the stability or half-life of the P2RX2 inhibitor (e.g., an Fc domain of an antibody or serum albumin, e.g., human serum albumin). The modification can also include conjugation to an antibody to target the agent to a particular cell or tissue. Additionally, the modification can be a chemical modification, packaging modification (e.g., packaging within a nanoparticle or microparticle), or targeting modification to prevent the agent from crossing the blood brain barrier.

Small Molecules

Numerous small molecule P2RX2 inhibitors useful in the methods of the invention are described herein in Tables 1 and 2 and additional small molecule P2RX2 inhibitors useful as therapies for cancer can also be identified through screening based on their ability to reduce or inhibit P2RX2 function or signaling. Small molecules include, but are not limited to, small peptides, peptidomimetics (e.g., peptoids), amino acids, amino acid analogs, synthetic polynucleotides, polynucleotide analogs, nucleotides, nucleotide analogs, organic and inorganic compounds (including heteroorganic and organometallic compounds) generally having a molecular weight less than about 5,000 grams per mole, e.g., organic or inorganic compounds having a molecular weight less than about 2,000 grams per mole, e.g., organic or inorganic compounds having a molecular weight less than about 1,000 grams per mole, e.g., organic or inorganic compounds having a molecular weight less than about 500 grams per mole, and salts, esters, and other pharmaceutically acceptable forms of such compounds.

In some embodiments, the P2RX2 inhibitor is a small molecule inhibitor of P2RX2 (e.g., a small molecule inhibitor listed in Table 1), or a P2RX2 binding partner antagonist (e.g., an antagonist of a binding partner selected from the group consisting of P2RX1, P2RX3, P2RX4, P2RX5, P2RX6, and P2RX7). P2RX2 inhibitors can be used to treat a disorder or condition described herein. A pharmaceutical composition including the P2RX2 inhibitor can be formulated for treatment of a cancer described herein. In some embodiments, a pharmaceutical composition that includes the P2RX2 inhibitor is formulated for local administration, e.g., to the affected site in a subject.

Antibodies

The P2RX2 inhibitor can be an antibody or antigen binding fragment thereof. For example, a P2RX2 inhibitor described herein is an antibody that reduces or blocks the activity and/or function of P2RX2 through binding to P2RX2 or a P2RX2 binding partner (e.g., a binding partner selected from the group consisting of P2RX1, P2RX3, P2RX4, P2RX5, P2RX6, and P2RX7) to block the binding between P2RX2 and a binding partner or to block P2RX2 multimerization.

The making and use of therapeutic antibodies against a target antigen (e.g., P2RX2 or a P2RX2 binding partner) is known in the art. See, for example, the references cited herein above, as well as Zhiqiang An (Editor), Therapeutic Monoclonal Antibodies: From Bench to Clinic. 1st Edition. Wiley 2009, and also Greenfield (Ed.), Antibodies: A Laboratory Manual. (Second edition) Cold Spring Harbor Laboratory Press 2013, for methods of making recombinant antibodies, including antibody engineering, use of degenerate oligonucleotides, 5'-RACE, phage display, and mutagenesis; antibody testing and characterization; antibody pharmacokinetics and pharmacodynamics; antibody purification and storage; and screening and labeling techniques.

Nucleic Acids

Inhibitory RNA

In some embodiments, the P2RX2 inhibitor is an inhibitory RNA molecule, e.g., that acts by way of the RNA interference (RNAi) pathway. An inhibitory RNA molecule can decrease the expression level (e.g., protein level or mRNA level) of P2RX2, a P2RX2 binding partner (e.g., a binding partner selected from the group consisting of P2RX1, P2RX3, P2RX4, P2RX5, P2RX6, and P2RX7), or a molecule required for P2RX2 signaling or function (e.g., a molecule required for downstream calcium signaling). For example, an inhibitory RNA molecule includes a short interfering RNA, short hairpin RNA, and/or a microRNA that targets full-length P2RX2, a P2RX2 binding partner (e.g., a binding partner selected from the group consisting of P2RX1, P2RX3, P2RX4, P2RX5, P2RX6, and P2RX7), or a molecule required for P2RX2 downstream signaling or function. A siRNA is a double-stranded RNA molecule that typically has a length of about 19-25 base pairs. A shRNA is a RNA molecule including a hairpin turn that decreases expression of target genes via RNAi. shRNAs can be delivered to cells in the form of plasmids, e.g., viral or bacterial vectors, e.g., by transfection, electroporation, or transduction). A microRNA is a non-coding RNA molecule that typically has a length of about 22 nucleotides. MiRNAs bind to target sites on mRNA molecules and silence the mRNA, e.g., by causing cleavage of the mRNA, destabilization of the mRNA, or inhibition of translation of the mRNA. In embodiments, the inhibitory RNA molecule decreases the level and/or activity of a negative regulator of function or a positive regulator of function. In other embodiments, the inhibitory RNA molecule decreases the level and/or activity of an inhibitor of a positive regulator of function.

An inhibitory RNA molecule can be modified, e.g., to contain modified nucleotides, e.g., 2'-fluoro, 2'-o-methyl, 2'-deoxy, unlocked nucleic acid, 2'-hydroxy, phosphorothioate, 2'-thiouridine, 4'-thiouridine, 2'-deoxyuridine. Without being bound by theory, it is believed that certain modification can increase nuclease resistance and/or serum stability, or decrease immunogenicity.

In some embodiments, the inhibitory RNA molecule decreases the level and/or activity or function of P2RX2, a P2RX2 binding partner (e.g., a binding partner selected from the group consisting of P2RX1, P2RX3, P2RX4, P2RX5, P2RX6, and P2RX7), or a molecule required for P2RX2 downstream signaling or function. In embodiments, the inhibitory RNA molecule inhibits expression of P2RX2, a P2RX2 binding partner (e.g., a binding partner selected from the group consisting of P2RX1, P2RX3, P2RX4, P2RX5, P2RX6, and P2RX7), or a molecule required for P2RX2 downstream signaling or function (e.g., inhibits translation to protein). In other embodiments, the inhibitor RNA molecule increases degradation of P2RX2, a P2RX2 binding partner (e.g., a binding partner selected from the group consisting of P2RX1, P2RX3, P2RX4, P2RX5, P2RX6, and P2RX7), or a molecule required for P2RX2 downstream signaling or function and/or decreases the stability (i.e., half-life) of P2RX2, a P2RX2 binding partner (e.g., a binding partner selected from the group consisting of P2RX1, P2RX3, P2RX4, P2RX5, P2RX6, and P2RX7), or a molecule required for P2RX2 downstream signaling or function. The inhibitory RNA molecule can be chemically synthesized or transcribed in vitro.

The making and use of inhibitory therapeutic agents based on non-coding RNA such as ribozymes, RNAse P, siRNAs, and miRNAs are also known in the art, for example, as described in Sioud, RNA Therapeutics: Function, Design, and Delivery (Methods in Molecular Biology). Humana Press 2010.

Viral Vectors

Viral vectors can be used to express a neurotoxin from Table 9 for combination therapy with a P2RX2 inhibitor. A viral vector expressing a neurotoxin from Table 9 can be administered to a cell or to a subject (e.g., a human subject or animal model) to decrease or block neurotransmission. Viral vectors can be directly administered (e.g., injected) to a tumor to treat cancer.

Viral genomes provide a rich source of vectors that can be used for the efficient delivery of exogenous genes into a mammalian cell. Viral genomes are particularly useful vectors for gene delivery because the polynucleotides contained within such genomes are typically incorporated into the nuclear genome of a mammalian cell by generalized or specialized transduction. These processes occur as part of the natural viral replication cycle, and do not require added proteins or reagents in order to induce gene integration. Examples of viral vectors include a retrovirus (e.g., Retroviridae family viral vector), adenovirus (e.g., Ad5, Ad26, Ad34, Ad35, and Ad48), parvovirus (e.g., adeno-associated viruses), coronavirus, negative strand RNA viruses such as orthomyxovirus (e.g., influenza virus), rhabdovirus (e.g., rabies and vesicular stomatitis virus), paramyxovirus (e.g., measles and Sendai), positive strand RNA viruses, such as picornavirus and alphavirus, and double stranded DNA viruses including adenovirus, herpesvirus (e.g., Herpes Simplex virus types 1 and 2, Epstein-Barr virus, cytomegalovirus, replication deficient herpes virus), and poxvirus (e.g., vaccinia, modified vaccinia Ankara (MVA), fowlpox and canarypox). Other viruses include Norwalk virus, togavirus, flavivirus, reoviruses, papovavirus, hepadnavirus, human papilloma virus, human foamy virus, and hepatitis virus, for example. Examples of retroviruses include: avian leukosis-sarcoma, avian C-type viruses, mammalian C-type, B-type viruses, D-type viruses, oncoretroviruses, HTLV-BLV group, lentivirus, alpharetrovirus, gammaretrovirus, spumavirus (Coffin, J. M., Retroviridae: The viruses and their replication, Virology (Third Edition) Lippincott-Raven, Philadelphia, 1996). Other examples include murine leukemia viruses, murine sarcoma viruses, mouse mammary tumor virus, bovine leukemia virus, feline leukemia virus, feline sarcoma virus, avian leukemia virus, human T-cell leukemia virus, baboon endogenous virus, Gibbon ape leukemia virus, Mason Pfizer monkey virus, simian immunodeficiency virus, simian sarcoma virus, Rous sarcoma virus and lentiviruses. Other examples of vectors are described, for example, in U.S. Pat. No. 5,801,030, the teachings of which are incorporated herein by reference.

Blood Brain Barrier Permeability

In some embodiments, the P2RX2 inhibitors for use in the present invention are agents that are not capable of crossing, or that do not cross, the blood brain barrier (BBB) of a mammal, e.g., an experimental rodent (e.g., mouse or rat), dog, pig, non-human primate, or a human. The BBB is a highly selective semipermeable membrane barrier that separates the circulating blood from the brain extracellular fluid (e.g., cerebrospinal fluid) in the central nervous system (CNS). The BBB is made up of high-density endothelial cells, which are connected by tight junctions. These cells prevent most molecular compounds in the bloodstream (e.g., large molecules and hydrophilic molecules) from entering the brain. Water, some gases (e.g., oxygen and carbon dioxide), and lipid-soluble molecules (e.g., hydrophobic molecules, such as steroid hormones) can cross the BBB by passive diffusion. Molecules that are needed for neural function, such as glucose and amino acids, are actively transported across the BBB.

A number of approaches can be used to render an agent BBB impermeable. These methods include modifications to increase an agent's size, polarity, or flexibility or reduce its lipophilicity, targeting approaches to direct an agent to another part of the body and away from the brain, and packaging approaches to deliver an agent in a form that does not freely diffuse across the BBB. These approaches can be used to render a BBB permeable P2RX2 inhibitor impermeable, and they can also be used to improve the properties (e.g., cell-specific targeting) of a P2RX2 inhibitor that does not cross the BBB. The methods that can be used to render an agent BBB impermeable are discussed in greater detail herein below.

Formulation of BBB-Permeable Agents for Enhanced Cell Targeting

One approach that can be used to render a P2RX2 inhibitor BBB impermeable is to conjugate the agent to a targeting moiety that directs it somewhere other than the brain. The targeting moiety can be an antibody for a receptor expressed by the target cell (e.g., N-Acetylgalactosamine for liver transport; DGCR2, GBF1, GPR44 or SerpinB10 for pancreas transport; Secretoglobin, family 1A, member 1 for lung transport). The targeting moiety can also be a ligand of any receptor or other molecular identifier expressed on the target cell in the periphery. These targeting moieties can direct the P2RX2 inhibitor of interest to its corresponding target cell, and can also prevent BBB crossing by directing the agent away from the BBB and increasing the size of the P2RX2 inhibitor via conjugation of the targeting moiety.

P2RX2 inhibitors can also be rendered BBB impermeable through formulation in a particulate delivery system (e.g., a nanoparticle, liposome, or microparticle), such that the agent is not freely diffusible in blood and cannot cross the BBB. The particulate formulation used can be chosen based on the desired localization of the P2RX2 inhibitor (e.g., a tumor, lymph node, lymphoid organ, or site of inflammation), as particles of different sizes accumulate in different locations. For example, nanoparticles with a diameter of 45 nm or less enter the lymph node, while 100 nm nanoparticles exhibit poor lymph node trafficking. Some examples of the link between particle size and localization in vivo are described in Reddy et al., J Controlled Release 112:26 2006, and Reddy et al., Nature Biotechnology 25:1159 2007.

P2RX2 inhibitors can be tested after the addition of a targeting moiety or after formulation in a particulate delivery system to determine whether or not they cross the BBB. Models for assessing BBB permeability include in vitro models (e.g., monolayer models, co-culture models, dynamic models, multi-fluidic models, isolated brain microvessels), in vivo models, and computational models as described in He et al., Stroke 45:2514 2014; Bickel, NeuroRx 2:15 2005; and Wang et al., Int J Pharm 288:349 2005. A P2RX2 inhibitor that exhibits BBB impermeability can be used in the methods described herein.

Modification of Existing Compounds to Render them BBB Impermeable

There are multiple parameters that have been empirically derived in the field of medicinal chemistry to predict whether a compound will cross the BBB. The most common numeric value for describing permeability across the BBB is the log BB, defined as the logarithmic ratio of the concentration of a compound in the brain and in the blood. Empirical rules of thumb have been developed to predict BBB permeability, including rules regarding molecular size, polar surface area, sum of oxygen and nitrogen atoms, lipophilicity (e.g., partition coefficient between apolar solvent and water), "lipoaffinity", molecular flexibility, and number of rotable bonds (summarized in Muehlbacher et al., J Comput Aided Mol Des. 25: 1095 2011; and Geldenhuys et al., Ther Deliv. 6: 961 2015). Some preferred limits on various parameters for BBB permeability are listed in Table 1 of Ghose et al., ACS Chem Neurosci. 3: 50 2012, which is incorporated herein by reference. Based on the parameters shown in the table, one of skill in the art could modify an existing P2RX2 inhibitor to render it BBB impermeable.

One method of modifying a P2RX2 inhibitor to prevent BBB crossing is to add a molecular adduct that does not affect the target binding specificity, kinetics, or thermodynamics of the agent. Molecular adducts that can be used to render an agent BBB impermeable include polyethylene glycol (PEG), a carbohydrate monomer or polymer, a dendrimer, a polypeptide, a charged ion, a hydrophilic group, deuterium, and fluorine. P2RX2 inhibitors can be tested after the addition of one or more molecular adducts or after any other properties are altered to determine whether or not they cross the BBB. Models for assessing BBB permeability include in vitro models (e.g., monolayer models, co-culture models, dynamic models, multi-fluidic models, isolated brain microvessels), in vivo models, and computational models as described in He et al., Stroke 45:2514 2014; Bickel, NeuroRx 2:15 2005; and Wang et al., Int J Pharm 288:349 2005. A P2RX2 inhibitor that exhibits BBB impermeability can be used in the methods described herein.

Screening for or Development of BBB Impermeable Agents

Another option for developing BBB impermeable agents is to find or develop new agents that do not cross the BBB. One method for finding new BBB impermeable agents is to screen for compounds that are BBB impermeable. Compound screening can be performed using in vitro models (e.g., monolayer models, co-culture models, dynamic models, multi-fluidic models, isolated brain microvessels), in vivo models, and computational models, as described in He et al., Stroke 45:2514 2014; Bickel, NeuroRx 2:15 2005; Wang et al., Int J Pharm 288:349 2005, and Czupalla et al., Methods Mol Biol 1135:415 2014. For example, the ability of a molecule to cross the blood brain barrier can be determined in vitro using a transwell BBB assay in which microvascular endothelial cells and pericytes are co-cultured separated by a thin macroporous membrane, see e.g., Naik et al., J Pharm Sci 101:1337 2012 and Hanada et al., Int J Mol Sci 15:1812 2014; or in vivo by tracking the brain uptake of the target molecule by histology or radio-detection. Compounds would be deemed appropriate for use as P2RX2 inhibitors in the methods described herein if they do not display BBB permeability in the aforementioned models.

Cancer

The methods described herein can be used to treat cancer in a subject by administering to the subject an effective amount of a P2RX2 inhibitor, e.g., a P2RX2 inhibitor described herein. The method may include administering locally (e.g., intratumorally) to the subject a P2RX2 inhibitor described herein in a dose (e.g., effective amount) and for a time sufficient to treat the cancer. For example, the stroma associated with the tumor, e.g., fibroblasts, is disrupted such that an essential function, e.g., the production of matrix metalloproteases, is altered to inhibit tumor survival or promote tumor control.

In some embodiments, the P2RX2 inhibitor inhibits proliferation or disrupts the function of non-neural cells associated with the cancer, e.g., the method includes administering to the subject an effective amount of a P2RX2 inhibitor for a time sufficient to inhibit proliferation or disrupt the function of non-neural cells associated with the cancer. Non-neural cells associated with the cancer include malignant cancer cells, malignant cancer cells in necrotic and hypoxic areas, adipocytes, pericytes, endothelial cells, cancer associated fibroblasts, fibroblasts, mesenchymal stem cells, red blood cells, or extracellular matrix. The proliferation of non-neural cells associated with the cancer may be decreased in the subject at least 1%, 2%, 5%, 10%, 15%, 20%, 25%, 30%, 35%, 40%, 50%, 60%, 70%, 80%, 90%, 95% or more, compared to before the administration. The proliferation of non-neural cells associated with the cancer can be decreased in the subject between 5-20%, between 5-50%, between 10-50%, between 20-80%, between 20-70%.

The P2RX2 inhibitor can treat cancer by increasing cancer cell death in a subject (e.g., a human subject or animal model) or in a cancer cell culture (e.g., a culture generated from a patient tumor sample, a cancer cell line, or a repository of patient samples). A P2RX2 inhibitor can increase cancer cell death by at least 1%, 2%, 5%, 10%, 15%, 20%, 25%, 30%, 35%, 40%, 50%, 60%, 70%, 80%, 90%, 95% or more compared to before administration to a subject or cancer cell culture. A P2RX2 inhibitor can increase cancer cell death in a subject or cancer cell culture between 5-20%, between 5-50%, between 10-50%, between 20-80%, between 20-70%.

The P2RX2 inhibitor can also act to inhibit cancer cell growth, proliferation, metastasis, migration, or invasion, e.g., the method includes administering to the subject (e.g., a human subject or animal model) or a cancer cell culture (e.g., a culture generated from a patient tumor sample, a cancer cell line, or a repository of patient samples) a P2RX2 inhibitor in an amount (e.g., an effective amount) and for a time sufficient to inhibit cancer cell growth, proliferation, metastasis, migration, or invasion. Cancer cell growth, proliferation, metastasis, migration, or invasion can be decreased in the subject or cancer cell culture at least 1%, 2%, 5%, 10%, 15%, 20%, 25%, 30%, 35%, 40%, 50%, 60%, 70%, 80%, 90%, 95% or more, compared to before the administration Cancer cell growth, proliferation, metastasis, migration, or invasion can be decreased in the subject or cancer cell culture between 5-20%, between 5-50%, between 10-50%, between 20-80%, between 20-70%.

The P2RX2 inhibitor can inhibit cancer cell invasion or metastasis along a nerve, e.g., the method includes administering to the subject (e.g., a human subject or animal model) a P2RX2 inhibitor in an amount (e.g., an effective amount) and for a time sufficient to inhibit cancer cell invasion or metastasis along a nerve. The P2RX2 inhibitor can decrease cancer cell invasion or metastasis along a nerve in the subject at least 1%, 2%, 5%, 10%, 15%, 20%, 25%, 30%, 35%, 40%, 50%, 60%, 70%, 80%, 90%, 95% or more, compared to before the administration. The P2RX2 inhibitor can decrease cancer cell invasion or metastasis along a nerve in the subject between 5-20%, between 5-50%, between 10-50%, between 20-80%, between 20-70%.

The P2RX2 inhibitor can also reduce the number of nerve fibers in the affected tissue or reduce the activity of peripheral nerve fibers in the affected tissue. For example, the method includes administering to the subject (e.g., a human subject or animal model) a P2RX2 inhibitor in an amount (e.g., an effective amount) and for a time sufficient to reduce the number of nerve fibers in the affected tissue or reduce the activity of peripheral nerve fibers in the affected tissue. The affected tissue can be a tumor or a tumor micro-environment. The number of nerve fibers in the affected tissue or the activity of peripheral nerve fibers in the affected tissue can be decreased in the subject at least 1%, 2%, 5%, 10%, 15%, 20%, 25%, 30%, 35%, 40%, 50%, 60%, 70%, 80%, 90%, 95% or more, compared to before the administration. The number of nerve fibers in the affected tissue or the activity of peripheral nerve fibers in the affected tissue can be decreased in the subject between 5-20%, between 5-50%, between 10-50%, between 20-80%, between 20-70%.

The nerve fibers that are modulated can be part of the peripheral nervous system, e.g., a somatic nerve, an autonomic nerve, a sensory nerve, a cranial nerve, an optic nerve, an olfactory nerve, a sympathetic nerve, a parasympathetic nerve, a chemoreceptor, a photoreceptor, a mechanoreceptor, a thermoreceptor, a nociceptor, an efferent nerve fiber, or an afferent nerve fiber.

Cancer Types

In the methods described herein, the cancer or neoplasm may be any solid or liquid cancer and includes benign or malignant tumors, and hyperplasias, including gastrointestinal cancer (such as non-metastatic or metastatic colorectal cancer, pancreatic cancer, gastric cancer, esophageal cancer, hepatocellular cancer, cholangiocellular cancer, oral cancer, lip cancer); urogenital cancer (such as hormone sensitive or hormone refractory prostate cancer, renal cell cancer, bladder cancer, penile cancer); gynecological cancer (such as ovarian cancer, cervical cancer, endometrial cancer); lung cancer (such as small-cell lung cancer and non-small-cell lung cancer); head and neck cancer (e.g., head and neck squamous cell cancer); CNS cancer including malignant glioma, astrocytomas, retinoblastomas and brain metastases; malignant mesothelioma; non-metastatic or metastatic breast cancer (e.g., hormone refractory metastatic breast cancer); skin cancer (such as malignant melanoma, basal and squamous cell skin cancers, Merkel Cell Carcinoma, lymphoma of the skin, Kaposi Sarcoma); thyroid cancer; bone and soft tissue sarcoma; and hematologic neoplasias (such as multiple myeloma, acute myelogenous leukemia, chronic myelogenous leukemia, myelodysplastic syndrome, acute lymphoblastic leukemia, Hodgkin's lymphoma).

Additional cancers that can be treated according to the methods described herein include breast cancer, lung cancer, stomach cancer, colon cancer, liver cancer, renal cancer, colorectal cancer, prostate cancer, pancreatic cancer, cervical cancer, anal cancer, vulvar cancer, penile cancer, vaginal cancer, testicular cancer, pelvic cancer, thyroid cancer, uterine cancer, rectal cancer, brain cancer, head and neck cancer, esophageal cancer, bronchus cancer, gallbladder cancer, ovarian cancer, bladder cancer, oral cancer, oropharyngeal cancer, larynx cancer, biliary tract cancer, skin cancer, a cancer of the central nervous system, a cancer of the respiratory system, and a cancer of the urinary system. Examples of breast cancers include, but are not limited to, triple-negative breast cancer, triple-positive breast cancer, HER2-negative breast cancer, HER2-positive breast cancer, estrogen receptor-positive breast cancer, estrogen receptor-negative breast cancer, progesterone receptor-positive breast cancer, progesterone receptor-negative breast cancer, ductal carcinoma in situ (DCIS), invasive ductal carcinoma, invasive lobular carcinoma, inflammatory breast cancer, Paget disease of the nipple, and phyllodes tumor.

Other cancers that can be treated according to the methods described herein include leukemia (e.g., B-cell leukemia, T-cell leukemia, acute myeloid leukemia (AML), chronic myeloid leukemia (CML), acute lymphocytic (lymphoblastic) leukemia (ALL), chronic lymphocytic leukemia (CLL), and erythroleukemia), sarcoma (e.g., angiosarcoma, chondrosarcoma, Ewing's sarcoma, fibrosarcoma, gastrointestinal stromal tumor, leiomyosarcoma, liposarcoma, malignant peripheral nerve sheath tumor, malignant fibrous cytoma, osteosarcoma, pleomorphic sarcoma, rhabdomyosarcoma, synovial sarcoma, vascular sarcoma, Kaposi's sarcoma, dermatofibrosarcoma, epithelioid sarcoma, leyomyosarcoma, and neurofibrosarcoma), carcinoma (e.g., basal cell carcinoma, large cell carcinoma, small cell carcinoma, non-small cell lung carcinoma, renal carcinoma, hepatocarcinoma, gastric carcinoma, choriocarcinoma, adenocarcinoma, hepatocellular carcinoma, giant (or oat) cell carcinoma, squamous cell carcinoma, adenosquamous carcinoma, anaplastmic carcinoma, adrenocortical carcinoma, cholangiocarcinoma, Merkel cell carcinoma, ductal carcinoma in situ (DCIS), and invasive ductal carcinoma), blastoma (e.g., hepatoblastoma, medulloblastoma, nephroblastoma, neuroblastoma, pancreatoblastoma, pleuropulmonary blastoma, retinoblastoma, and glioblastoma multiforme), lymphoma (e.g., Hodgkin's lymphoma, non-Hodgkin's lymphoma, and Burkitt lymphoma), myeloma (e.g., multiple myeloma, plasmacytoma, localized myeloma, and extramedullary myeloma), melanoma (e.g., superficial spreading melanoma, nodular melanoma, lentigno maligna melanoma, acral lentiginous melanoma, and amelanotic melanoma), neuroma (e.g., ganglioneuroma, Pacinian neuroma, and acoustic neuroma), glioma (e.g., astrocytoma, oligoastrocytoma, ependymoma, brainstem glioma, optic nerve glioma, and oligoastrocytoma), pheochromocytoma, meningioma, malignant mesothelioma, and virally induced cancer.

In some embodiments, the cancer is a paraneoplastic cancer (e.g., a cancer that causes a paraneoplastic syndrome). Paraneoplastic syndromes are rare disorders that are triggered by an altered immune system response to a neoplasm, and are mediated by humoral factors such as hormones, cytokines, or auto-antibodies produced by the tumor. Symptoms of paraneoplastic syndrome may be endocrine, neuromuscular, or musculoskeletal, cardiovascular, cutaneous, hematologic, gastrointestinal, renal, or neurological. Paraneoplastic syndromes commonly present with lung, breast, and ovarian cancer and cancer of the lymphatic system (e.g., lymphoma). Paraneoplastic neurological disorders are disorders that affect the central or peripheral nervous system, and can include symptoms such as ataxia (difficulty with walking and balance), dizziness, nystagmus (rapid uncontrolled eye movements), difficulty swallowing, loss of muscle tone, loss of fine motor coordination, slurred speech memory loss, vision problems, sleep disturbances, dementia, seizures, or sensory loss in the limbs. Breast, ovarian, and lung cancers are most commonly associated with paraneoplastic neurological disorders. Other common types of paraneoplastic syndromes include paraneoplastic cerebellar degeneration, paraneoplastic pemphigus, paraneoplastic autonomic neuropathy, paraneoplastic encephalomyelitis, and cancer-associated autoimmune retinopathy.

Endocrine paraneoplastic syndromes include Cushing syndrome (caused by ectopic ACTH), which is most commonly caused by small cell lung cancer, pancreatic carcinoma, neural tumors, or thymoma; SIADH (caused by antidiuretic hormone), which is most commonly caused by small cell lung cancer and CNS malignancies; hypercalcemia (caused by PTHrp, TGFα, TNF, or IL-1), which is most commonly caused by lung cancer, breast carcinoma, renal and bladder carcinoma, multiple myeloma, adult T cell leukemia/lymphoma, ovarian carcinoma, and squamous cell carcinoma (e.g., lung, head, neck, or esophagus carcinoma); hyperglycemia (caused by insulin insulin-like substance, or "big" IGF-II), which is most commonly caused by fibrosarcoma, mesenchymal sarcomas, insulinoma, and hepatocellular carcinoma; carcinoid syndrome (caused by serotonin or bradykinin), which is most commonly caused by bronchial adenoma, pancreatic carcinoma, and gastric carcinoma; and hyperaldosteronism (caused by aldosterone), which is most commonly caused by adrenal adenoma/Conn's syndrome, non-Hodgkin's lymphoma, ovarian carcinoma, and pulmonary cancer.

Neurological paraneoplastic syndromes include Lambert-Eaton myasthenic syndrome (LEMS), which is most commonly caused by small cell lung cancer; paraneoplastic cerebellar degeneration, which is most commonly caused by lung cancer, ovarian cancer, breast carcinoma, and Hodgkin's lymphoma; encephalomyelitis; limbic encephalitis, which is most commonly caused by small cell lung carcinoma; myasthenia gravis, which is most commonly caused by thymoma; brainstem encephalitis; opsoclonus myoclonus ataxia (caused by autoimmune reaction against Nova-1), which is most commonly caused by breast carcinoma, ovarian carcinoma, small cell lung carcinoma, and neuroblastoma; anti-NMDA receptor encephalitis (caused by autoimmune reaction against NMDAR subunits), which is most commonly caused by teratoma; and polymyositis, which is most commonly caused by lung cancer, bladder cancer, and non-Hodgkin's lymphoma. Mucotaneous paraneoplastic syndromes include acanthosis *nigricans*, which is most commonly caused by gastric carcinoma, lung carcinoma, and uterine carcinoma; dermatomyositis, which is most commonly caused by bronchogenic carcinoma, breast carcinoma, ovarian cancer, pancreatic cancer, stomach cancer, colorectal cancer, and Non-Hodgkin's lymphoma; Leser-Trelat sign; necrolytic migratory erythema, which is most commonly caused by glucoganoma; Sweet's syndrome; florid cutaneous papillomatosis; pyoderma gangrenosum; and acquired generalized hypertrichosis.

Hematological syndromes include granulocytosis (caused by G-CSF); polycythemia (caused by erythropoietin), which is commonly caused by renal carcinoma, cerebellar hemangioma, and heptatocellular carcinoma; Trousseau sign (caused by mucins), which is commonly caused by pancreatic carcinoma and bronchogenic carcinoma; nonbacterial thrombotic endocarditis, which is caused by advanced cancers; and anemia, which is most commonly caused by thymic neoplasms. Other paraneoplastic syndromes include membranous glomerular nephritis; neoplastic fever; Staffer syndrome, which is caused by renal cell carcinoma; and tumor-induced osteomalacia (caused by FGF23), which is caused by hemangiopericytoma and phosphaturic mesenchymal tumor.

In some embodiments, a subject is identified as having cancer after presenting with symptoms of a paraneoplastic syndrome. A common symptom of paraneoplastic syndrome is fever. Auto-antibodies directed against nervous system proteins are also frequently observed in patients with paraneoplastic syndromes, including anti-Hu, anti-Yo, anti-Ri, anti-amphiphysin, anti-CV2, anti-Ma2, anti-recoverin, anti-transducin, anti-carbonic anhydrase II, anti-arrestin, anti-GCAP1, anti-GCAP2, anti-HSP27, anti-Rab6A, and anti-PNR. Other symptoms that can be used to identify a patient with paraneoplastic cancer include ataxia, dizziness, nystagmus, difficulty swallowing, loss of muscle tone, loss of fine motor coordination, slurred speech memory loss, vision loss, sleep disturbances, dementia, seizures, dysgeusia, cachexia, anemia, itching, or sensory loss in the limbs. In some embodiments, a patient presents with symptoms of paraneoplastic syndrome and is then identified as having cancer based on imaging tests (e.g., CT, MRI, or PET scans).

The cancer may be highly innervated, metastatic, non-metastatic cancer, or benign (e.g., a benign tumor). The cancer may be a primary tumor or a metastasized tumor.

In some embodiments, the cancer is a P2RX2-associated cancer (e.g., a cancer in which P2RX2 is expressed, amplified, and/or overexpressed).

Subjects who can be treated with the methods disclosed herein include subjects who have had one or more tumors resected, received chemotherapy or other pharmacological treatment for the cancer, received radiation therapy, and/or received other therapy for the cancer. Subjects who have not previously been treated for cancer can also be treated with the methods disclosed herein.

Combination Therapies

A P2RX2 inhibitor described herein can be administered in combination with a second therapeutic agent for treatment of cancer. In some embodiments, the second therapeutic agent is selected based on tumor type, tumor tissue of origin, tumor stage, or mutations in genes expressed by the tumor.

Checkpoint Inhibitors

One type of agent that can be administered in combination with a P2RX2 inhibitor described herein is a checkpoint inhibitor. Checkpoint inhibitors can be broken down into at least 4 major categories: i) agents such as antibodies that block an inhibitory pathway directly on T cells or NK cells (e.g., PD-1 targeting antibodies such as nivolumab and pembrolizumab, antibodies targeting TIM-3, and antibodies targeting LAG-3, 2B4, CD160, A2aR, BTLA, CGEN-15049, or KIR), ii) agents such as antibodies that activate stimulatory pathways directly on T cells or NK cells (e.g., antibodies targeting OX40, GITR, or 4-1 BB), iii) agents such as antibodies that block a suppressive pathway on immune cells or rely on antibody-dependent cellular cytotoxicity to deplete suppressive populations of immune cells (e.g., CTLA-4 targeting antibodies such as ipilimumab, antibodies targeting VISTA, and antibodies targeting PD-L2, Gr1, or Ly6G), and iv) agents such as antibodies that block a suppressive pathway directly on cancer cells or that rely on antibody-dependent cellular cytotoxicity to enhance cytotoxicity to cancer cells (e.g., rituximab, antibodies targeting PD-L1, and antibodies targeting B7-H3, B7-H4, Gal-9, or MUC1). Such agents described herein can be designed and produced, e.g., by conventional methods known in the art (e.g., Templeton, Gene and Cell Therapy, 2015; Green and Sambrook, Molecular Cloning, 2012).

Chemotherapy

A second type of therapeutic agent that can be administered in combination with a P2RX2 inhibitor described herein is a chemotherapeutic agent (e.g., a cytotoxic agent or other chemical compound useful in the treatment of cancer). These include alkylating agents, antimetabolites, folic acid analogs, pyrimidine analogs, purine analogs and related inhibitors, *vinca* alkaloids, epipodopyyllotoxins, antibiotics, L-asparaginase, topoisomerase inhibitors, interferons, platinum coordination complexes, anthracenedione substituted urea, methyl hydrazine derivatives, adrenocortical suppressant, adrenocorticosteroides, progestins, estrogens, antiestrogen, androgens, antiandrogen, and gonadotropin-releasing hormone analog. Also included is 5-fluorouracil (5-FU), leucovorin (LV), irenotecan, oxaliplatin, capecitabine, paclitaxel and doxetaxel. Non-limiting examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII; dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel; chloranbucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DMFO); retinoids such as retinoic acid; capecitabine; and pharmaceutically acceptable salts, acids or derivatives of any of the above. Two or more chemotherapeutic agents can be used in a cocktail to be administered in combination with the first therapeutic agent described herein. Suitable dosing regimens of combination chemotherapies are known in the art.

Biologic Cancer Agents

Another type of therapeutic agent that can be administered in combination with a P2RX2 inhibitor described herein is a therapeutic agent that is a biologic such a cytokine (e.g., interferon or an interleukin (e.g., IL-2)) used in cancer treatment. In other embodiments the biologic is an anti-angiogenic agent, such as an anti-VEGF agent, e.g., bevacizumab. In some embodiments the biologic is an immunoglobulin-based biologic, e.g., a monoclonal antibody (e.g., a humanized antibody, a fully human antibody, an Fc fusion protein or a functional fragment thereof) that agonizes a target to stimulate an anti-cancer response, or antagonizes an antigen important for cancer. Such agents include Rituximab; Daclizumab; Basiliximab; Palivizumab; Infliximab; Trastuzumab; Gemtuzumab ozogamicin; Alemtuzumab; Ibritumomab tiuxetan; Adalimumab; Omalizumab; Tositumomab-I-131; Efalizumab; Cetuximab; Bevacizumab; Natalizumab; Tocilizumab; Panitumumab; Ranibizumab; Eculizumab; Certolizumab pegol; Golimumab; Canakinumab; Ustekinumab; Ofatumumab; Denosumab; Motavizumab; Raxibacumab; Belimumab; Ipilimumab; Brentuximab Vedotin; Pertuzumab; Ado-trastuzumab emtansine; and Obinutuzumab. Also included are antibody-drug conjugates. Examples of biologic cancer agents that can be used in combination with P2RX2 inhibitors described herein are shown in Table 3 below.

TABLE 3

APPROVED CANCER ANTIBODIES

| Antibody | Company | Antigen | Indication |
| --- | --- | --- | --- |
| ado-trastuzumab emtansine | Genentech | HER2 | Metastatic breast cancer |
| alemtuzumab | Genzyme | CD52 | B-cell chronic lymphocytic leukemia |
| atezolizumab | Genentech | PD-L1 | Urothelial carcinoma<br>Metastatic non-small cell lung cancer |
| avelumab | EMD Serono | PD-L1 | Metastatic Merkel cell carcinoma |
| bevacizumab | Genentech | VEGF | Metastatic colorectal cancer |
| blinatumomab | Amgen | CD19 | Precursor B-cell acute lymphoblastic leukemia |
| brentuximab vedotin | Seattle Genetics | CD30 | Hodgkin lymphoma<br>Anaplastic large-cell lymphoma |
| cetuximab | ImClone Systems | EGFR | Metastatic colorectal carcinoma |
| daratumumab | Janssen Biotech | CD38 | Multiple myeloma |
| dinutuximab | United Therapeutics | GD2 | Pediatric high-risk neuroblastoma |
| durvalumab | AstraZeneca | PD-L1 | Urothelial carcinoma |
| elotuzumab | Bristol-Myers Squibb | SLAMF7 | Multiple myeloma |
| ibritumomab tiuxetan | Spectrum Pharmaceuticals | CD20 | Relapsed or refractory low-grade, follicular, or transformed B-cell non-Hodgkin's lymphoma |
| ipilimumab | Bristol-Myers Squibb | CTLA-4 | Metastatic melanoma |
| necitumumab | Eli Lilly | EGFR | Metastatic squamous non-small cell lung carcinoma |
| nivolumab | Bristol-Myers Squibb | PD-1 | Metastatic melanoma<br>Metastatic squamous non-small cell lung carcinoma |
| obinutuzumab | Genentech | CD20 | Chronic lymphocytic leukemia |
| ofatumumab | Glaxo Grp | CD20 | Chronic lymphocytic leukemia |
| olaratumab | Eli Lilly | PDGFRA | Soft tissue sarcoma |
| panitumumab | Amgen | EGFR | Metastatic colorectal cancer |
| pembrolizumab | Merck | PD-1 | Metastatic melanoma |
| pertuzumab | Genentech | HER2 | Metastatic breast cancer |
| ramucirumab | Eli Lilly | VEGFR2 | Gastric cancer |
| rituximab | Genentech | CD20 | B-cell non-Hodgkin's lymphoma |
| trastuzumab | Genentech | HER2 | Metastatic breast cancer |

Cancer-Specific Agents

In some embodiments, the therapeutic agents administered with the P2RX2 inhibitors described herein are cancer-specific. Cancer-specific agents are agents that have been shown to be particularly effective against certain types of cancer. Cancer-specific agents that can be administered with the P2RX2 inhibitors described herein are listed in Table 4 below.

TABLE 4

CANCER-SPECIFIC AGENTS

| Cancer type | Agents |
| --- | --- |
| Pancreatic cancer | Chemotherapeutics (Paclitaxel Albumin-stabilized Nanoparticle Formulation, Erlotinib Hydrochloride, Everolimus, Fluorouracil Injection, Gemcitabine Hydrochloride, Irinotecan Hydrochloride Liposome, Mitomycin C, Sunitinib Malate, Folfirinox, Gemcitabine-Cisplatin, Gemcitabine-Oxaliplatin, Off, Lanreotide Acetate, Abraxane, Gemcitabine, Irinotecan, 5-FU, Oxaliplatin) |
| Melanoma | Checkpoint inhibitors (pembro, ipi, nivolumab, durvalumab), BRaf inhibitors (vemurafenib, debrafenib), MEK inhibitors, CDK4 inhibitors (ribociclib) |
| Renal cell carcinoma | Checkpoint inhibitors (pembro, ipi, nivolumab, durvalumab), mTOR inhibitors (everolimus), bevacizumab |
| Lung cancer | Checkpoint inhibitors (pembro, ipi, nivolumab, durvalumab), EGFR inhibitors (erlotinib, gefitinib, cetuximab) |
| Esophageal cancer | Chemotherapeutic agents (5FU, docetaxel), trastuzumab |
| Ovarian cancer | Chemotherapeutics (taxanes, cisplatin) |
| Uterine cancer | Chemotherapeutics (taxanes, cisplatin) |
| Head and Neck cancer | Checkpoint inhibitors (pembro, ipi, nivolumab, durvalumab), EGFR inhibitors (erlotinib, gefitinib, cetuximab) |
| Mesothelioma | Chemotherapeutics (pemetrexed, cisplatin) |

Non-Drug Therapies

Another type of agent that can be administered in combination with a P2RX2 inhibitor is a therapeutic agent that is a non-drug treatment. For example, the second therapeutic agent is radiation therapy, cryotherapy, hyperthermia and/or surgical excision of tumor tissue.

Neurotransmission Blockers

In some embodiments, the P2RX2 inhibitor is administered in combination with a neurotransmission blocker (e.g., an agent that decreases neurotransmission). A neurotransmission blocker can be used to reduce or inhibit neural activity in a cancer or tumor that is innervated by nerves or to decrease the number of nerves in the tumor. For example, in some embodiments, the neurotransmission blocker is an antagonist of a neurotransmitter receptor listed in Table 5. Exemplary antagonists are listed in Tables 7A-7K. Neurotransmission blockers also include agents that decrease neurotransmitter synthesis or release (e.g., agents that decrease the activity of a biosynthetic protein encoded by a gene in Table 5 via inhibition or downregulation, or agents that decrease the activity of a synaptic or vesicular protein via blocking, disrupting, downregulating, or antagonizing the protein), increase neurotransmitter reuptake or degradation (e.g., agents that agonize, open, or stabilize transporters that remove neurotransmitter from the synaptic cleft), decrease neurotransmitter receptor activity (e.g., agents that decrease the activity of a signaling protein encoded by a gene in Table 5 via blocking or antagonizing the protein, or agents that block, antagonize, or downregulate a neurotransmitter receptor listed in Table 5), decrease neurotransmitter receptor synthesis or membrane insertion, increase neurotransmitter degradation, regulate neurotransmitter receptor conformation (e.g., agents that bind to a receptor and keep it in a "closed" or "inactive" conformation), and disrupt the pre- or postsynaptic machinery (e.g., agents that block or disrupt a structural protein, or agents that block, disrupt, downregulate, or antagonize a synaptic or vesicular protein). In some embodiments, the neurotransmitter receptor is a channel (e.g., a ligand or voltage gated ion channel), the activity of which can be decreased by blockade, antagonism, or inverse agonism of the channel. Neurotransmission blockers further include agents that sequester, block, antagonize, or degrade a neurotransmitter listed in Tables 5 or 6. Neurotransmission blockers include antibodies that bind to or block the function of neurotransmitters, neurotransmitter receptor antagonists, and toxins that disrupt synaptic release. Neurotransmission modulators can decrease neurotransmission by 10%, 20%, 30%, 40%, 50%, 60%, 70%, 80%, 90%, 95%, 98% or more. Neurotransmission blockers can be administered in any of the modalities described herein (e.g., antibody, small molecule, nucleic acid, polypeptide, or viral vector).

TABLE 5

NEUROTRANSMITTER GENES & PATHWAYS

| Gene | Pathway | Type | Accession Number | Entrez Gene ID |
|---|---|---|---|---|
| ABAT | Neurotransmitter | Biosynthesis | P80404 | 18 |
| ACHE | Neurotransmitter | Biosynthesis | P22303 | 43 |
| ADORA2A | Neurotransmitter | Receptor | P29274 | 135 |
| ADORA2B | Neurotransmitter | Receptor | P29275 | 136 |
| Adra1a | Adrenergic/Neurotransmitter | Receptor | P35348 | 148 |
| Adra1b | Adrenergic/Neurotransmitter | Receptor | P35368 | 147 |
| Adra1d | Adrenergic/Neurotransmitter | Receptor | P25100 | 146 |
| Adra2a | Adrenergic/Neurotransmitter | Receptor | P08913 | 150 |
| Adra2b | Adrenergic/Neurotransmitter | Receptor | P18089 | 151 |
| Adra2c | Adrenergic/Neurotransmitter | Receptor | P18825 | 152 |
| Adrb1 | Adrenergic/Neurotransmitter | Receptor | P08588 | 153 |
| Adrb2 | Adrenergic/Neurotransmitter | Receptor | P07550 | 154 |
| Adrb3 | Adrenergic/Neurotransmitter | Receptor | P13945 | 155 |
| Adrbk1 | Adrenergic | Kinase | P25098 | 156 |
| Adrbk2 | Adrenergic | Kinase | P35626 | 157 |
| BACE1 | Neurotransmitter | Biosynthesis | P56817 | 23621 |
| BCHE | Neurotransmitter | Biosynthesis | P06276 | 590 |

TABLE 5-continued

NEUROTRANSMITTER GENES & PATHWAYS

| Gene | Pathway | Type | Accession Number | Entrez Gene ID |
|---|---|---|---|---|
| BRS3 | Neuromodulator | Receptor | P32247 | P32247 |
| C6orf89 | Neuromodulator | Receptor | Q6UWU4 | 221477 |
| CHAT | Neurotransmitter | Biosynthesis | P28329 | 1103 |
| CHRFAM7A | Neurotransmitter | Receptor | Q494W8 | 89832 |
| Chrm1 | Cholinergic/Neurotransmitter | Receptor | P11229 | 1128 |
| Chrm2 | Cholinergic/Neurotransmitter | Receptor | P08172 | 1129 |
| Chrm3 | Cholinergic/Neurotransmitter | Receptor | P20309 | 1131 |
| Chrm4 | Cholinergic/Neurotransmitter | Receptor | P08173 | 1132 |
| Chrm5 | Cholinergic/Neurotransmitter | Receptor | P08912 | 1133 |
| Chrna1 | Cholinergic/Neurotransmitter | Receptor | P02708 | 1134 |
| Chrna10 | Cholinergic/Neurotransmitter | Receptor | Q9GZZ6 | 57053 |
| Chrna2 | Cholinergic/Neurotransmitter | Receptor | Q15822 | 1135 |
| Chrna3 | Cholinergic/Neurotransmitter | Receptor | P32297 | 1136 |
| Chrna4 | Cholinergic/Neurotransmitter | Receptor | P43681 | 1137 |
| Chrna5 | Cholinergic/Neurotransmitter | Receptor | P30532 | 1138 |
| Chrna6 | Cholinergic/Neurotransmitter | Receptor | Q15825 | 8973 |
| Chrna7 | Cholinergic/Neurotransmitter | Receptor | P36544 | 1139 |
| Chrna9 | Cholinergic/Neurotransmitter | Receptor | Q9UGM1 | 55584 |
| Chrnb1 | Cholinergic/Neurotransmitter | Receptor | P11230 | 1140 |
| Chrnb2 | Cholinergic/Neurotransmitter | Receptor | P17787 | 1141 |
| Chrnb3 | Cholinergic/Neurotransmitter | Receptor | Q05901 | 1142 |
| Chrnb4 | Cholinergic/Neurotransmitter | Receptor | P30926 | 1143 |
| Chrnd | Cholinergic/Neurotransmitter | Receptor | Q07001 | 1144 |
| Chrne | Cholinergic/Neurotransmitter | Receptor | Q04844 | 1145 |
| Chrng | Cholinergic/Neurotransmitter | Receptor | P07510 | 1146 |
| CNR1 | Cannabinoid/Neurotransmitter | Receptor | P21554 | 1268 |
| CNR2 | Cannabinoid/Neurotransmitter | Receptor | P34972 | 1269 |
| CNRIP1 | Neurotransmitter | Receptor | Q96F85 | 25927 |
| COMT | Neurotransmitter | Biosynthesis | P21964 | 1312 |
| CPA4 | Neurotransmitter | Biosynthesis | Q9UI42 | 51200 |
| CPE | Neuropeptide/Neurotransmitter | Biosynthesis | P16870 | 1363 |
| CREM | Neurotransmitter | Signaling | Q03060 | 1390 |
| DAGLA | Neurotransmitter (Cannabinoid) | Biosynthesis | Q9Y4D2 | 747 |
| DAGLB | Neurotransmitter (Cannabinoid) | Biosynthesis | Q8NCG7 | 221955 |
| DBH | Neurotransmitter | Biosynthesis | P09172 | 1621 |
| DDC | Neurotransmitter | Biosynthesis | P20711 | 1644 |
| DGKI | Neurotransmitter | Biosynthesis | O75912 | 9162 |
| DOPO | Dopaminergic | Receptor | P09172 | 1621 |
| DPP4 | Neurotransmitter | Biosynthesis | P27487 | 1803 |
| Drd1 | Dopaminergic/Neurotransmitter | Receptor | P21728 | 1812 |
| Drd2 | Dopaminergic/Neurotransmitter | Receptor | P14416 | 1813 |
| Drd3 | Dopaminergic/Neurotransmitter | Receptor | P35462 | 1814 |
| Drd4 | Dopaminergic/Neurotransmitter | Receptor | P21917 | 1815 |
| Drd5 | Dopaminergic/Neurotransmitter | Receptor | P21918 | 1816 |

TABLE 5-continued

NEUROTRANSMITTER GENES & PATHWAYS

| Gene | Pathway | Type | Accession Number | Entrez Gene ID |
|---|---|---|---|---|
| ECEL1 | Neurotransmitter | Biosynthesis | O95672 | 9427 |
| FAAH | Neurotransmitter | Biosynthesis | O00519 | 2166 |
| FNTA | Neurotransmitter | Signaling | P49354 | 2339 |
| GABARAP | Neurotransmitter | Receptor | O95166 | 11337 |
| GABARAPL1 | Amine Neuromodulator | Receptor | Q9H0R8 | 23710 |
| GABARAPL2 | Amine Neuromodulator | Receptor | P60520 | 11345 |
| GABBR1 | Neurotransmitter | Receptor | Q9UBS5 | 2550 |
| GABBR2 | Amine Neuromodulator | Receptor | O75899 | 9568 |
| GABRA1 | Neurotransmitter | Receptor | P14867 | 2554 |
| GABRA2 | Neurotransmitter | Receptor | P47869 | 2555 |
| GABRA3 | Neurotransmitter | Receptor | P34903 | 2556 |
| GABRA4 | Neurotransmitter | Receptor | P48169 | 2557 |
| GABRA5 | Neurotransmitter | Receptor | P31644 | 2558 |
| GABRA6 | Neurotransmitter | Receptor | Q16445 | 2559 |
| GABRB1 | Neurotransmitter | Receptor | P18505 | 2560 |
| GABRB2 | Neurotransmitter | Receptor | P47870 | 2561 |
| GABRB3 | Neurotransmitter | Receptor | P28472 | 2562 |
| GABRD | Neurotransmitter | Receptor | O14764 | 2563 |
| GABRE | Neurotransmitter | Receptor | P78334 | 2564 |
| GABRG1 | Neurotransmitter | Receptor | Q8N1C3 | 2565 |
| GABRG2 | Neurotransmitter | Receptor | P18507 | 2566 |
| GABRG3 | Neurotransmitter | Receptor | Q99928 | 2567 |
| GABRP | Neurotransmitter | Receptor | O00591 | 2568 |
| GABRQ | Neurotransmitter | Receptor | Q9UN88 | 55879 |
| GABRR1 | Neurotransmitter | Receptor | P24046 | 2569 |
| GABRR2 | Neurotransmitter | Receptor | P28476 | 2570 |
| GABRR3 | Neurotransmitter | Receptor | A8MPY1 | 200959 |
| GAD1 | Neurotransmitter | Biosynthesis | Q99259 | 2571 |
| GAD2 | Neurotransmitter | Biosynthesis | Q05329 | 2572 |
| GCHFR | Neurotransmitter | Biosynthesis | P30047 | 2644 |
| GLRA1 | Neurotransmitter | Receptor | P23415 | 2741 |
| GLRA2 | Neurotransmitter | Receptor | P23416 | 2742 |
| GLRA3 | Neurotransmitter | Receptor | O75311 | 8001 |
| GLRA4 | Neurotransmitter | Receptor | Q5JXX5 | 441509 |
| GLRB | Neurotransmitter | Receptor | P48167 | 2743 |
| GLS | Neurotransmitter | Biosynthesis | O94925 | 2744 |
| GLS2 | Neurotransmitter | Biosynthesis | Q9UI32 | 27165 |
| GluA1 (GluR1) | Amine Neuromodulator | Receptor | P42261 | 2890 |
| GluK1 (GluR5) | Amine Neuromodulator | Receptor | P39086 | 2897 |
| GLUL | Neurotransmitter | Biosynthesis | P15104 | 2752 |
| GluN1(NR1) | Amine Neuromodulator | Receptor | Q05586 | 2902 |
| GNMT | Neurotransmitter | Biosynthesis | Q14749 | 27232 |
| GPER1 | Neurotransmitter | Receptor | Q99527 | 2852 |
| GPR1 | Neurotransmitter | Receptor | P46091 | 2825 |
| GPR139 | Neurotransmitter | Receptor | Q6DWJ6 | 124274 |
| GPR143 | Neurotransmitter | Receptor | P51810 | 4935 |
| GPR149 | Neurotransmitter | Receptor | Q86SP6 | 344758 |
| GPR18 | Neurotransmitter | Receptor | Q14330 | 2841 |
| GPR21 | Neurotransmitter | Receptor | Q99679 | 2844 |
| GPR26 | Neurotransmitter | Receptor | Q8NDV2 | 2849 |
| GPR3 | Neurotransmitter | Receptor | P46089 | 2827 |
| GPR35 | Neurotransmitter | Receptor | Q9HC97 | 2859 |
| GPR52 | Neurotransmitter | Receptor | Q9Y2T5 | 9293 |
| GPR55 | Neurotransmitter | Receptor | Q9Y2T6 | 9290 |
| GPR78 | Neurotransmitter | Receptor | Q96P69 | 27201 |
| GPR83 | Neurotransmitter | Receptor | Q9NYM4 | 10888 |
| GPR84 | Neurotransmitter | Receptor | Q9NQS5 | 53831 |
| GPRASP1 | Neurotransmitter | Receptor | Q5JY77 | 9737 |
| GPR50 | Amine Neuromodulator | Receptor | Q13585 | 9248 |
| GRIA1 | Neurotransmitter | Receptor | P42261 | 2890 |
| GRIA2 | Neurotransmitter | Receptor | P42262 | 2891 |
| GRIA3 | Neurotransmitter | Receptor | P42263 | 2892 |
| GRIA4 | Neurotransmitter | Receptor | P48058 | 2893 |
| GRID1 | Neurotransmitter | Receptor | Q9ULK0 | 2894 |
| GRID2 | Neurotransmitter | Receptor | O43424 | 2895 |
| GRIK1 | Neurotransmitter | Receptor | P39086 | 2897 |
| GRIK2 | Neurotransmitter | Receptor | Q13002 | 2898 |
| GRIK3 | Neurotransmitter | Receptor | Q13003 | 2899 |
| GRIK4 | Neurotransmitter | Receptor | Q16099 | 2900 |
| GRIK5 | Neurotransmitter | Receptor | Q16478 | 2901 |
| GRIN1 | Neurotransmitter | Receptor | Q05586 | 2902 |
| GRIN2A | Neurotransmitter | Receptor | Q12879 | 2903 |
| GRIN2B | Neurotransmitter | Receptor | Q13224 | 2904 |
| GRIN2C | Neurotransmitter | Receptor | Q14957 | 2905 |
| GRIN2D | Neurotransmitter | Receptor | Q15399 | 2906 |
| GRIN3A | Neurotransmitter | Receptor | Q8TCU5 | 116443 |
| GRIN3B | Neurotransmitter | Receptor | O60391 | 116444 |
| GRK2 | Neurotransmitter | Receptor | P25098 | 156 |
| GRK3 | Neurotransmitter | Receptor | P35626 | 157 |
| GRM1 | Neurotransmitter | Receptor | Q13255 | 2911 |
| GRM2 | Neurotransmitter | Receptor | Q14416 | 2912 |
| GRM3 | Neurotransmitter | Receptor | Q14832 | 2913 |
| GRM4 | Neurotransmitter | Receptor | Q14833 | 2914 |
| GRM5 | Neurotransmitter | Receptor | P41594 | 2915 |
| GRM6 | Neurotransmitter | Receptor | O15303 | 2916 |
| GRM7 | Neurotransmitter | Receptor | Q14831 | 2917 |
| GRM8 | Neurotransmitter | Receptor | O00222 | 2918 |
| HNMT | Neurotransmitter | Biosynthesis | P50135 | 3176 |
| HOMER1 | Neurotransmitter | Receptor | Q86YM7 | 9456 |
| HRH1 | Neurotransmitter | Receptor | P35367 | 3269 |
| HRH2 | Neurotransmitter | Receptor | P25021 | 3274 |
| HRH3 | Neurotransmitter | Receptor | Q9Y5N1 | 11255 |
| HRH4 | Neurotransmitter | Receptor | Q9H3N8 | 59340 |
| Htr1a | Neurotransmitter | Receptor | P08908 | 3350 |
| Htr1b | Neurotransmitter | Receptor | P28222 | 3351 |
| Htr1c | Neurotransmitter | Receptor | P28335 | |
| Htr1d | Neurotransmitter | Receptor | P28221 | 3352 |
| Htr1e | Neurotransmitter | Receptor | P28566 | 3354 |
| Htr1f | Neurotransmitter | Receptor | P30939 | 3355 |
| Htr2a | Neurotransmitter | Receptor | P28223 | 3356 |
| Htr2b | Neurotransmitter | Receptor | P41595 | 3357 |
| Htr2c | Neurotransmitter | Receptor | P28335 | 3358 |
| Htr3a | Neurotransmitter | Receptor | P46098 | 3359 |
| Htr3b | Neurotransmitter | Receptor | O95264 | 9177 |
| Htr3c | Neurotransmitter | Receptor | Q8WXA8 | 170572 |
| Htr3d | Neurotransmitter | Receptor | Q70Z44 | 200909 |
| HTR3E | Neurotransmitter | Receptor | A5X5Y0 | 285242 |
| Htr4 | Neurotransmitter | Receptor | Q13639 | 3360 |
| Htr5a | Neurotransmitter | Receptor | P47898 | 3361 |
| Htr5b | Neurotransmitter | Receptor | P35365 | 79247 |
| HTR5BP | Neurotransmitter | Receptor | | 645694 |
| Htr6 | Neurotransmitter | Receptor | P50406 | 3362 |
| Htr7 | Neurotransmitter | Receptor | P32305 | 3363 |
| ITPR1 | Neurotransmitter | Signaling | Q14643 | 3708 |
| ITPR2 | Neurotransmitter | Signaling | Q14571 | 3709 |
| ITPR3 | Neurotransmitter | Signaling | Q14573 | 3710 |
| LYNX1 | Neurotransmitter | Receptor | Q9BZG9 | 66004 |
| MAOA | Neurotransmitter | Biosynthesis | P21397 | 4128 |
| MAOB | Neurotransmitter | Biosynthesis | P27338 | 4129 |
| NAMPT | Neurotransmitter | Biosynthesis | P43490 | 10135 |
| NISCH | Neurotransmitter | Receptor | Q9Y2I1 | 11188 |
| NOS1 | Neurotransmitter | Biosynthesis | P29475 | 4842 |
| NPTN | Neurotransmitter | Receptor | Q9Y639 | 27020 |
| P2RX1 | Neurotransmitter | Receptor | P51575 | 5023 |
| P2RX2 | Neurotransmitter | Receptor | Q9UBL9 | 22953 |
| P2RX3 | Neurotransmitter | Receptor | P56373 | 5024 |
| P2RX4 | Neurotransmitter | Receptor | Q99571 | 5025 |
| P2RX5 | Neurotransmitter | Receptor | Q93086 | 5026 |
| P2RX6 | Neurotransmitter | Receptor | O15547 | 9127 |
| P2RX7 | Neurotransmitter | Receptor | Q99572 | 5027 |
| P2RY11 | Neurotransmitter | Receptor | Q96G91 | 5032 |
| PAH | Neurotransmitter | Biosynthesis | P00439 | 5053 |
| PC | Neurotransmitter | Biosynthesis | P11498 | 5091 |
| PDE1B | Neurotransmitter | Signaling | Q01064 | 5153 |
| PDE4A | Neurotransmitter | Signaling | P27815 | 5141 |
| PDE4D | Neurotransmitter | Signaling | Q08499 | 5144 |
| PHOX2A | Neurotransmitter | Biosynthesis | O14813 | 401 |
| PHOX2B | Neurotransmitter | Biosynthesis | Q99453 | 8929 |
| PIK3CA | Neurotransmitter | Signaling | P42336 | 5290 |
| PIK3CB | Neurotransmitter | Signaling | P42338 | 5291 |
| PIK3CG | Neurotransmitter | Signaling | P48736 | 5294 |
| PLCB1 | Neurotransmitter | Signaling | Q9NQ66 | 23236 |
| PLCB2 | Neurotransmitter | Signaling | Q00722 | 5330 |

TABLE 5-continued

NEUROTRANSMITTER GENES & PATHWAYS

| Gene | Pathway | Type | Accession Number | Entrez Gene ID |
|---|---|---|---|---|
| PLCB3 | Neurotransmitter | Signaling | Q01970 | 5331 |
| PLCB4 | Neurotransmitter | Signaling | Q15147 | 5332 |
| PLCD1 | Neurotransmitter | Signaling | P51178 | 5333 |
| PLCE1 | Neurotransmitter | Signaling | Q9P212 | 51196 |
| PLCG1 | Neurotransmitter | Signaling | P19174 | 5335 |
| PLCL1 | Neurotransmitter | Signaling | Q15111 | 5334 |
| PLCL2 | Neurotransmitter | Signaling | Q9UPR0 | 23228 |
| PPP1CB | Neurotransmitter | Signaling | P62140 | 5500 |
| PPP100 | Neurotransmitter | Signaling | P36873 | 5501 |
| PRIMA1 | Neurotransmitter | Biosynthesis | Q86XR5 | 145270 |
| PRKACG | Neurotransmitter | Signaling | P22612 | 5568 |
| PRKAR2B | Neurotransmitter | Signaling | P31323 | 5577 |
| PRKCG | Neurotransmitter | Signaling | P05129 | 5582 |
| PRKX | Neurotransmitter | Signaling | P51817 | 5613 |
| RIC3 | Neurotransmitter | Receptor | Q7Z5B4 | 79608 |
| SHANK3 | Neurotransmitter | Signaling | Q9BYB0 | 85358 |
| SLC6A1 | Amine Neuromodulator | Transferase | P30531 | 6529 |
| SLC6A13 | Amine Neuromodulator | Transferase | Q9NSD5 | 6540 |
| Slc6a4 | Serotonin | Transporter | P31645 | 6532 |
| SNX13 | Neurotransmitter | Signaling | Q9Y5W8 | 23161 |
| TAAR1 | Amine Neuromodulator | Receptor | Q96RJ0 | 134864 |
| TAAR2 | Amine Neuromodulator | Receptor | Q9P1P5 | 9287 |
| TAAR5 | Neurotransmitter | Receptor | O14804 | 9038 |
| TH | Neurotransmitter | Biosynthesis | P07101 | 7054 |
| TPH1 | Neurotransmitter | Biosynthesis | P17752 | 7166 |
| TPH2 | Neurotransmitter | Biosynthesis | Q8IWU9 | 121278 |
| TRHDE | Neurotransmitter | Biosynthesis | Q9UKU6 | 29953 |

TABLE 6

NEUROTRANSMITTERS

| Ligand | Pathway | Type |
|---|---|---|
| 2-Arachidonoylglycerol | Endocannabinoid | Ligand |
| 2-Arachidonyl glyceryl ether | Endocannabinoid | Ligand |
| 3-methoxytyramine | Amines | Ligand |
| Acetylcholine | Amino Acids | Ligand |
| Adenosine | Purine | Ligand |
| Adenosine triphosphate | Purine | Ligand |
| Agmatine | Amino Acids | Ligand |
| Anandamide | Endocannabinoid | Ligand |
| Aspartate | Amino Acids | Ligand |
| Carbon monoxide | Gas | Ligand |
| D-serine | Amino Acids | Ligand |
| Dopamine | Monoamines | Ligand |
| Dynorphin | Opioids | Ligand |
| Endorphin | Opioids | Ligand |
| Enkephalin | Opioids | Ligand |
| Epinephrine | Monoamines | Ligand |
| Gamma-aminobutyric acid | Amino Acids | Ligand |
| Glutamate | Amino Acids | Ligand |
| Glycine | Amino Acids | Ligand |
| Histamine | Monoamines | Ligand |
| N-Acetylaspartylglutamate | Neuropeptides | Ligand |
| N-Arachidonoyl dopamine | Endocannabinoid | Ligand |
| N-methylphenethylamine | Amines | Ligand |
| N-methyltryptamine | Amines | Ligand |
| Nitric oxide | Gas | Ligand |
| Norepinephrine | Monoamines | Ligand |
| Octopamine | Amines | Ligand |
| Phenethylamine | Amines | Ligand |
| Serotonin | Monoamines | Ligand |
| Synephrine | Amines | Ligand |
| Tryptamine | Amines | Ligand |
| Tyramine | Amines | Ligand |
| Virodhamine | Endocannabinoid | Ligand |

TABLE 7A

AGONISTS AND ANTAGONIST AGENTS

| Gene | Agonist | Antagonist |
|---|---|---|
| Adrb2 | NCX 950 | Alprenolol |
| Accession Number: | Bitolterol | Carvedilol |
| P07550 | Isoetarine | Desipramine |
| | Norepinephrine | Nadolol |
| | Phenylpropanolamine | Levobunolol |
| | Dipivefrin | Metipranolol |
| | Epinephrine | Bevantolol |
| | Orciprenaline | Oxprenolol |
| | Dobutamine | Nebivolol |
| | Ritodrine | Asenapine |
| | Terbutaline | Bupranolol |
| | Salmeterol | Penbutolol |
| | Formoterol | Celiprolol |
| | Salbutamol | Pindolol |
| | Isoprenaline | Acebutolol |
| | Arbutamine | Bopindolol |
| | Arformoterol | |
| | Fenoterol | |
| | Pirbuterol | |
| | Ephedra | |
| | Procaterol | |
| | Clenbuterol | |
| | Bambuterol | |
| | Indacaterol | |
| | Droxidopa | |
| | Olodaterol | |
| | Vilanterol | |
| | Pseudoephedrine | |
| | Cabergoline | |
| | Mirtazepine | |

TABLE 7A-continued

AGONISTS AND ANTAGONIST AGENTS

| Gene | Agonist | Antagonist |
|---|---|---|
| Adra1d<br>Accession Number:<br>P25100 | Midodrine<br>Norepinephrine<br>Clonidine<br>Oxymetazoline<br>Pergolide<br>Bromocriptine<br>Droxidopa<br>Xylometazoline<br>Ergotamine<br>Cirazoline<br>Cabergoline<br>Methoxamine<br>Epinephrine | Dapiprazole<br>Amitriptyline<br>Alfuzosin<br>Promazine<br>Prazosin<br>Imipramine<br>Nortriptyline<br>Doxazosin<br>Nicardipine<br>Dronedarone<br>Tamsulosin<br>Propiomazine<br>Phenoxybenzamine<br>Carvedilol<br>Doxepin<br>Terazosin<br>Quetiapine<br>Methotrimeprazine<br>Silodosin |
| Adrb1<br>Accession Number:<br>P08588 | Isoetarine<br>Norepinephrine<br>Phenylpropanolamine<br>Epinephrine<br>Dobutamine<br>Salbutamol<br>Isoprenaline<br>Arbutamine<br>Fenoterol<br>Pirbuterol<br>Ephedra<br>Clenbuterol<br>Droxidopa<br>Pseudoephedrine<br>Carteolol<br>Cabergoline<br>Mirtazapine<br>Loxapine<br>Vortioxetine<br>Desipramine | Esmolol<br>Betaxolol<br>Metoprolol<br>Atenolol<br>Timolol<br>Sotalol<br>Propranolol<br>Labetalol<br>Bisoprolol<br>Alprenolol<br>Amiodarone<br>Carvedilol<br>Nadolol<br>Levobunolol<br>Metipranolol<br>Bevantolol<br>Practolol<br>Oxprenolol<br>Celiprolol<br>Nebivolol<br>Asenapine<br>Bupranolol<br>Penbutolol<br>Pindolol<br>Acebutolol<br>Bopindolol<br>Cartelol |
| Adrb3<br>Accession Number:<br>P13945 | SR 58611<br>Norepinephrine<br>Epinephrine<br>Isoprenaline<br>Arbutamine<br>Fenoterol<br>Ephedra<br>Clenbuterol<br>Droxidopa<br>Mirabegron | Bopindolol<br>Propranolol<br>Bupranolol |
| Adrbk1<br>Accession Number:<br>P25098 | ATP<br>Carbachol<br>Dopamine<br>Isoproterenol<br>Morphine<br>DAMGO<br>histamine<br>Acetylcholine<br>Etorphine<br>NMDA<br>Dopamine | Alprenolol<br>Heparin |
| Adrbk2<br>Accession Number:<br>P26819 | Isoproterenol<br>DAMGO<br>ATP | Propranolol |
| Chrm3<br>Accession Number:<br>P20309 | cgmp<br>ATP<br>Cevimeline<br>arecoline<br>oxotremorine-M<br>NNC 11-1314 | MT3<br>Hexocyclium<br>Himbacine<br>Biperiden<br>lithocholylcholine<br>AFDX384 |

TABLE 7A-continued

AGONISTS AND ANTAGONIST AGENTS

| Gene | Agonist | Antagonist |
|---|---|---|
| | xanomeline | 4-DAMP |
| | oxotremorine | hexahydrodifenidol |
| | pentylthio-TZTP | VU0255035 |
| | arecaidine propargyl ester | N-methyl scopolamine |
| | NNC 11-1607 | Darifenacin |
| | furmethide | Thiethylperazine |
| | NNC 11-1585 | methoctramine |
| | Acetylcholine | silahexocyclium |
| | methylfurmethide | Strychnine |
| | Bethanechol | MT7 |
| | Carbachol | Heparin |
| | Succinylcholine | Olanzapine |
| | ALKS 27 | Pirenzepine |
| | itopride | Clidinium |
| | methacholine | Ipratropium |
| | Meperidine | Propantheline |
| | Cinnarizine | Dicyclomine |
| | Trimipramine | Darifenacin |
| | | Tiotropium |
| | | Atropine |
| | | Scopolamine |
| | | Amitriptyline |
| | | Doxepin |
| | | Lidocaine |
| | | Nortriptyline |
| | | Tropicamide |
| | | Metixene |
| | | Homatropine Methylbromide |
| | | Solifenacin |
| | | Glycopyrrolate |
| | | Propiomazine |
| | | Diphemanil Methylsulfate |
| | | Promethazine |
| | | Diphenidol |
| | | Pancuronium |
| | | Ziprasidone |
| | | Quetiapine |
| | | Imipramine |
| | | Clozapine |
| | | Cyproheptadine |
| | | Aripiprazole |
| | | Nicardipine |
| | | Amoxapine |
| | | Loxapine |
| | | Promazine |
| | | Oxyphencyclimine |
| | | Anisotropine Methylbromide |
| | | Tridihexethyl |
| | | Chlorpromazine |
| | | Ketamine |
| | | Cyclosporin A |
| | | Paroxetine |
| | | Benzquinamide |
| | | Tolterodine |
| | | Oxybutynin |
| | | Alcuronium |
| | | WIN 62, 577 |
| | | Tramadol |
| | | Chlorprothixene |
| | | Aclidinium |
| | | Methotrimeprazine |
| | | Umeclidinium |
| | | Cryptenamine |
| | | Mepenzolate |
| | | Maprotiline |
| | | Brompheniramine |
| | | Isopropamide |
| | | Trihexyphenidyl |
| | | Ipratropium bromide |
| | | Hyoscyamine |
| | | Procyclidine |
| | | Pipecuronium |
| | | Fesoterodine |
| | | Disopyramide |
| | | Desipramine |
| | | Mivacurium |

TABLE 7A-continued

AGONISTS AND ANTAGONIST AGENTS

| Gene | Agonist | Antagonist |
|---|---|---|
| Chrna3 Accession Number: P32297 | Nicotine Varenicline Acetylcholine Ethanol Cytisine Levamisole Galantamine | A-867744 NS1738 Hexamethonium Mecamylamine Dextromethorphan Pentolinium Levomethadyl Acetate Bupropion |
| Chrna6 Accession Number: Q15825 | Nicotine Cytisine Varenicline Galantamine | Hexamethonium Mecamylamine |
| Chrna9 Accession Number: Q9UGM1 | Nicotine Galantamine Ethanol ATG003 Lobeline RPI-78M | Hexamethonium Mecamylamine Tetraethylammonium Muscarine Strychnine |
| Chrnb1 Accession Number: P11230 | Galantamine | |
| Chrnb4 Accession Number: P30926 | Nicotine Varenicline PNU-120596 Ethanol Galantamine | Atropine Oxybutynin Pentolinium Dextromethorphan |
| Chrng Accession Number: P07510 | Galantamine | |
| Adcyap1 Accession Number: P18509 | Nicotine CGMP Apomorphine Suramin Nifedipine ATP Dihydrotestosterone Maxadilan Dexamethasone Acetylcholine Histamine Carbachol NMDA Dopamine Isoproterenol Salbutamol Morphine Clonidine Nimodipine 2,6-Diamino-Hexanoic Acid Amide | Atropine PPADS Onapristone Muscarine Haloperidol Astressin Melatonin Scopolamine Tetrodotoxin Apamin Hexamethonium Indomethacin Propranolol Bumetanide Progesterone Charybdotoxin Prazosin |
| CYSLTR1 Accession Number: Q9Y271 | Salbutamol Dexamethasone Arachidonic acid Histamine | Montelukast Zafirlukast Cinalukast Pranlukast Nedocromil Theophylline Indomethacin Zileuton Iralukast Pobilukast Sulukast Verlukast |
| LTB4R Accession Number: Q15722 | LTB ATP Dexamethasone cholesterol 20-hydroxy-LTB< 12R-HETE arachidonic acid | U75302 CP105696 CP-195543 Etalocib SC-41930 LY255283 Zafirlukast ONO-4057 RO5101576 BILL 260 |

TABLE 7A-continued

AGONISTS AND ANTAGONIST AGENTS

| Gene | Agonist | Antagonist |
|---|---|---|
| PENK<br>Accession Number:<br>P01210 | Dopamine<br>kainate<br>NMDA<br>DAMGO<br>Morphine | Naltrexone<br>Naloxone<br>Progesterone |
| Htr2c<br>Accession Number:<br>P28335 | Apomorphine<br>Bifeprunox<br>Tramadol<br>AL-37350A<br>5-MeO-DMT<br>BW723C86<br>CGS-12066<br>DOI<br>5-CT<br>YM348<br>LSD<br>xanomeline<br>WAY-163909<br>Dopamine<br>LY344864<br>VER-3323<br>TFMPP<br>8-OH-DPAT<br>MK-212<br>NMDA<br>org 12962<br>5-MeOT<br>RU 24969<br>Acetylcholine<br>QUINPIROLE<br>quipazine<br>tryptamine<br>Ro 60-0175<br>Oxymetazoline<br>Ergotamine<br>Cabergoline<br>Lorcaserin<br>Pergolide<br>Methylergonovine<br>Renzapride<br>Pramipexole<br>GR-127935<br>BRL-15572<br>ipsapirone<br>SB 216641<br>SL65.0155<br>S 16924<br>Bromocriptine<br>Lisuride<br>Tegaserod<br>Epicept NP-1<br>dapoxetine<br>Dexfenfluramine<br>3,4-Methylenedioxymethamphetamine<br>Ropinirole<br>Maprotiline<br>Desipramine | Melatonin<br>SB 224289<br>LY334362<br>FR260010<br>Sulpiride<br>Thiethylperazine<br>cyamemazine<br>Mesulergine<br>SB 221284<br>Zotepine<br>Metergoline<br>methiothepin<br>Spiperone<br>SB 215505<br>Tiospirone<br>SB 228357<br>Pizotifen<br>SB 206553<br>SB 204741<br>SDZ SER-082<br>Ritanserin<br>SB 242084<br>S33084<br>Roxindole<br>RS-127445<br>Terguride<br>EGIS-7625<br>SB 243213<br>RS-102221<br>Olanzapine<br>Aripiprazole<br>Agomelatine<br>Ziprasidone<br>Quetiapine<br>Sarpogrelate<br>Perphenazine<br>Thioridazine<br>Sertindole<br>Loxapine<br>Methysergide<br>Risperidone<br>Asenapine<br>Mianserin<br>Clozapine<br>Trifluoperazine<br>Trazodone<br>Doxepin<br>Nortriptyline<br>Chlorprothixene<br><br>Minaprine<br>Propiomazine<br>Mirtazapine<br>Amoxapine<br>Yohimbine<br>Cyproheptadine<br>Imipramine<br>Amitriptyline<br>Promazine<br>Chlorpromazine<br>Ketamine<br>Propranolol<br>Fluoxetine<br>Ketanserin<br>Mesulergine<br>AC-90179<br>Ergoloid mesylate 2<br>Methotrimeprazine<br>Paliperidone<br>Clomipramine<br>Trimipramine |

TABLE 7A-continued

AGONISTS AND ANTAGONIST AGENTS

| Gene | Agonist | Antagonist |
|---|---|---|
| GABA Receptor Accession Numbers (Q9UBS5, O95166, O75899, P28472, P18507, P47870, P47869, O14764) | Bamaluzole<br>GABA<br>Gabamide<br>GABOB<br>Gaboxadol<br>Ibotenic acid<br>Isoguvacine<br>Isonipecotic acid<br>Muscimol<br>Phenibut<br>Picamilon<br>Progabide<br>Quisqualamine<br>SL 75102<br>Thiomuscimol<br>Alcohols (e.g., ethanol, isopropanol)<br>Avermectins (e.g., ivermectin)<br>Barbiturates (e.g., phenobarbital)<br>Benzodiazepines<br>Bromides (e.g., potassium bromide)<br>Carbamates (e.g., meprobamate, carisoprodol)<br>Chloralose<br>Chlormezanone<br>Clomethiazole<br>Dihydroergolines (e.g., ergoloid (dihydroergotoxine))<br>Etazepine<br>Etifoxine<br>Imidazoles (e.g., etomidate)<br>Kavalactones (found in kava)<br>Loreclezole<br>Neuroactive steroids (e.g., allopregnanolone, ganaxolone)<br>Nonbenzodiazepines (e.g., zaleplon, zolpidem, zopiclone, eszopiclone)<br>Petrichloral<br>Phenols (e.g., propofol)<br>Piperidinediones (e.g., glutethimide, methyprylon)<br>Propanidid<br>Pyrazolopyridines (e.g., etazolate)<br>Quinazolinones (e.g., methaqualone)<br>Skullcap constituents<br>Stiripentol<br>Sulfonylalkanes (e.g., sulfonmethane, tetronal, trional)<br>Valerian constituents (e.g., valeric acid, valerenic acid)<br>Volatiles/gases (e.g., chloral hydrate, chloroform, diethyl ether, sevoflurane) | Captodiame<br>Nefazodone<br>bicuculline<br>Metrazol<br>Flumazenil<br>Thiothixine<br>Bupropion<br>Caffeine |
| Glutamate Receptor Accession Number: (P42261, P39086, P39086, Q13585, P42261, P42262, P42263, P48058, P39086, Q13002, Q13003, Q13003, Q16478, Q12879, Q14957, Q13224, Q14957, Q15399, Q8TCU5, O60391) | 3,5-dihydroxyphenylglycine<br>eglumegad<br>Biphenylindanone A<br>DCG-IV<br>L-AP4 | APICA<br>EGLU<br>LY-341, 495 |
| CNR1/CNR2 Accession Number: (P21554, P34972) | N-Arachidonoylethanolamine<br>2-Arachidonoyl-glycerol<br>2-Arachidonoyl-glycerylether<br>N-Arachidonoyl-dopamine<br>O-Arachidonoyl-ethanolamine<br>N-Arachidonoylethanolamine<br>2-Arachidonoyl-glycerol<br>2-Arachidonoyl-glycerylether<br>N-Arachidonoyl-dopamine | SR 141716A<br>LY-320135<br>AM251<br>AM281<br>SR 144528<br>AM630 |

TABLE 7A-continued

AGONISTS AND ANTAGONIST AGENTS

| Gene | Agonist | Antagonist |
|---|---|---|
| | O-Arachidonoyl-ethanolamine | |
| | Δ-9-THC | |
| | CP-55, 940 | |
| | R(+)-WIN 55, 212-2 | |
| | HU-210 | |
| | Levonantradol | |
| | Nabilone | |
| | Methanandamide | |
| | ACEA | |
| | O-1812 | |
| | Δ9-THC | |
| | CP-55, 940 | |
| | R(+)-WIN 55, 212-2 | |
| | HU-210 | |
| | Levonantradol | |
| | Nabilone | |
| | Methanandamide | |
| | JWH-015 | |
| | JWH-133 | |

TABLE 7B

ADRENERGIC AGONISTS AND ANTAGONISTS

| Receptor | Agonist | Antagonist |
|---|---|---|
| Non-selective | adrenaline (epinephrine), noradrenaline (norepinephrine), isoprenaline (isoproterenol), dopamine, caffeine, nicotine, tyramine, methylphenidate, ephedrine and pseudophedrine. | carvedilol, arotinolol, and labetalol |
| α1 selective (ADRA1A, ADRA1B, ADRA1D) | phenylephrine, methoxamine, midodrine, cirazoline, xylometazoline, metaraminol chloroehtylclonidine, oxymetazoline | acepromazine, alfuzosin, doxazosin, labetalol, phenoxybenzamine, KW3902, phentolamine, prazosin, tamsulosin, terazosin, tolazoline, trazodone, amitriptyline, silodosin, clomipramine, doxepin, trimipramine, typical and atypical antipsychotics, and antihistamines, such as hyroxyzine |
| α2 selective (ADRA2A, ADRA2B, ADRA2C) | α-methyl dopa, clonidine, brimonidine, agmatine, dexmedetomidine, medetomidine, romifidine chloroethylclonidine, detomidine, lofexidine, xylazine, tizanidine, guanfacine, and amitraz | phentolamine, phenoxybenzamine, yohimbine, idazoxan, atipamezole, mirtazapine, tolazoline, trazodone, and typical and atypical antipsychotics |
| β1 selective (ADRB1) | Dobutamine | metroprolol, atenolol, acebutolol, bisoprolol, betaxolol, levobetaxolol, esmolol, celiprolol, carteolol, landiolol, oxprenolol, propanolol, practolol, penbutolol, timolol, labetalol, nebivolol, levobunolol, nadolol, pindolol, sotalol, metipranolol, tertatolol, vortioxene |
| β2 selective (ADRB2) | salbutamol, albuterol, bitolterol mesylate, levabuterol, ritodrine, metaproterenol, terbutaline, salmeterol, formoterol, and pirbuterol | butaxamine, acebutolol, timolol, propanolol, levobunolol, carteolol, labetalol, pindolol, oxprenolol, nadolol, metipranolol, penbutolol, tertatolol, sotalol |
| β3 selective (ADRB3) | L-796568, amibegron, solabegron, mirabegron | SR 59230A, arotinolol |

TABLE 7C

DOPAMINE AGONISTS AND ANTAGONISTS

| Receptor | Agonist | Antagonist |
| --- | --- | --- |
| Non-selective | pramipexole, ropinirole, rotigotine, apomorphine, propylnorapomorphine, bromocriptine, cabergoline, ciladopa, dihydrexidine, dinapsoline, doxamthrine, epicriptine, lisuride, pergolide, piribedil, quinagolide, roxindole, dopamine | haloperidol, paliperidone, clozapine, risperidone, olanzapine, quetiapine, ziprasidone, metoclopramide, droperidol, domperidone, amoxapine, clomipramine, trimipramine, choline, melatonin, acepromazine, amisulpride, asenapine, azaperone, benperidol, bromopride, butaclamol, chlorpromazine, clebopride, chlorprothixene, clopenthixol, clocapramine, eticlopride, flupenthixol, fluphenazine, fluspirilene, hydroxyzine, itopride, iodobenzamide, levomepromazine, levosulpiride, loxapine, mesoridazine, metopimazine, mosapramine, nafadotride, nemonapride, penfluridol, perazine, perphenazine, pimozide, prochlorperazine, promazine, pipotiazine, raclopride, remoxipride, spiperone, spiroxatrine, stepholidine, sulpiride, sultopride, tetrahydropalmatine, thiethylperazine, thioridazine, thiothixene, tiapride, trifluoperazine, trifluperidol, triflupromazine, thioproperazine, taractan, zotepine, zuclopenthixol, ziprasidone, ANP-010, NGD-94-4 |
| D1 (DRD1) | Fenoldopam, A-86929, dihydrexidine, dinapsoline, dinoxyline, doxanthrine, SKF-81297, SKF-82958, SKF-38393, G-BR-APB, dopexamine | SCH-23,390, SKF-83,959, Ecopipam, Clebopride, Flupenthixol, Zuclopenthixol, Taractan, PSYRX-101, LuAF-35700, GLC-756, ADX10061, Zicronapine |
| D2 (DRD2) | Cabergoline, pergolide, quinelorane, sumanirole, talipexole, piribedil, quinpirole, quinelorane, dinoxyline, dopexamine | Chloroethylnorapomorphine, desmethoxyfallypride, domperidone, eticlopride, fallypride, hydroxyzine, itopride, L-741,626, SV 293, yohimbine, raclopride, sulpiride, paliperidone, penfluridol, quetiapine, lurasidone, risperidone, olanzapine, blonanserin, perphenazine, metoclopramide, trifluoperazine, clebopride, levosulpiride, flupenthixol, haloperidol, thioridazine, alizapride, amisulpride, asenapine, bromopride, bromperidol, clozapine, fluphenazine, perphanazine, loxapine, nemonapride, pericyazine, pipamperone, prochlorperazine, thioproperazine, thiethylperazine, tiapride, ziprasidone, zuclopenthixol, taractan, fluanisone, melperone, molindone, remoxipride, sultopride, ALKS 3831, APD-403, ONC201, pridopidine, DSP-1200, NG-101, TAK-906, ADN-1184, ADN-2013, AG-0098, DDD-016, IRL-626, KP303, ONC-206, PF-4363467, PGW-5, CG-209, ABT-925, AC90222, ACP-005, ADN-2157, CB030006, CLR-136, Egis-11150, Iloperidone, JNJ-37822681, DLP-115, AZ-001, S-33138, SLV-314, Y-931, YKP1358, YK-P1447, APD405, CP-903397, ocaperidone, zicronapine, TPN-902 |
| D3 (DRD3) | Piribedil, quinpirole, captodiame, compound R, R-16, FAUC 54, FAUC 73, PD-128,907, PF-219,061, PF-592,379, CJ-1037, FAUC 460, FAUC 346, cariprazine | Domperidone, FAUC 365, nafadotride, raclopride, PNU-99,194, SB-277011-A, sulpiride, risperidone, YQA14, U99194, SR 21502, levosulpiride, amisulpride, nemonapride, ziprasidone, taractan, sultopride, APD-403, F17464, ONC201, NG-101, TAK-906, ONC-206, PF-4363467, ABT-127, ABT-614, GSK-598809, GSK-618334, S-14297, S-33138, YKP1358, YK-P1447 |
| D4 (DRD4) | WAY-100635, A-412,997, ABT-724, ABT-670, FAUC 316, PD-168, 077, | A-381393, FAUC 213, L-745,870, L-570,667, ML-398, fananserin, clozapine, |

TABLE 7C-continued

DOPAMINE AGONISTS AND ANTAGONISTS

| Receptor | Agonist | Antagonist |
| --- | --- | --- |
| | CP-226,269 | PNB-05, SPI-376, SPI-392, Lu-35-138, NG D-94-1 |
| D5 (DRD5) | Dihydrexidine, rotigotine, SKF-83,959, fenoldopam, | SCH 23390 |
| Partial | aplindore, brexpiprazole, aripiprazole, CY-208,243, pardoprunox, phencyclidine, and salvinorin A | |

TABLE 7D

GABA AGONISTS AND ANTAGONISTS

| Receptor | Agonist | Antagonist |
| --- | --- | --- |
| GABA$_A$ | barbiturates (e.g., allobarbital, amobarbital, aprobarbital, alphenal, barbital, brallobarbital, phenobarbital, secobarbital, thiopental), bamaluzole, GABA, GABOB, gaboxadol, ibotenic acid, isoguvacine, isonipecotic acid, muscimol, phenibut, picamilon, progabide, quisqualamine, SL 75102, thiomuscimol, positive allosteric modulators (PAMs) (e.g., alcohols, such as ethanol and isopropanol; avermectins, such as ivermectin; benzodiazepines, such as diazepam, alprazolam, chlordiazepoxide, clonazepam, flunitrazepam, lorazepam, midazolam, oxazepam, prazepam, brotizolam, triazolam, estazolam, lormetazepam, nitrazepam, temazepam, flurazepam, clorazepate halazepam, prazepam, nimetazepem, adinazolam, and climazolam; bromides, such as potassium bromide; carbamates, such as meprobamate and carisoprodol; chloralose; chlormezanone; chlomethiazole; dihydroergolines, such as ergoloid; etazepine; etifoxine; imidazoles, such as etomidate; imidazopyridines, such as alpidem and necopdiem; kavalactones; loreclezole; neuroactive steroids, such as allopregnanolone, pregnanolone, dihydrodeoxycorticosterone, tetrahydrodeoxycortisosterone, androstenol, androsterone, etiocholanolone, 3α-androstanediol, 5α, 5β, or 3α-dihydroprogesterone, and ganaxolone; nonbenzodiazepines, such as zalepon, zolpidem, zopiclone, and eszopiclone; petrichloral; phenols, such as propofol; piperidinediones, such as glutethimide and methyprylon; propanidid; pyrazolopyridines, such as etazolate; pyrazolopyrimidines, such as divaplon and fasiplon; cyclopyrrolones, sush as pagoclone and suproclone; β-cabolines, such as abecarnil and geodecarnil; quinazolinones, such as methaqualone; *Scutellaria* constituents; stiripentol; sulfonylalkanes, such as | bicuculline, gabazine, hydrastine, pitrazepin, sinomenine, tutin, thiocolchicoside, metrazol, securinine, gabazine |

TABLE 7D-continued

GABA AGONISTS AND ANTAGONISTS

| Receptor | Agonist | Antagonist |
|---|---|---|
| | sulfonomethane, teronal, and trional; Valerian constituents, such as valeric acid and valerenic acid; and gases, such as chloral hydrate, chloroform, homotaurine, diethyl ether, and sevoflurane. | |
| $GABA_B$ | 1,4-butanediol, baclofen, GABA, Gabamide, GABOB, gamma-butyrolactone, gamma-hydroxybutyric acid, gamma-hyrdoxyvaleric acid, gamma-valerolactone, isovaline, lesogaberan, phenibut, picamilon, progabide, homotaurine, SL-75102, tolgabide | CGP-35348, homotaurine, phaclofen, saclofen, and SCH-50911 |
| $GABA_{A\text{-}\rho}$ | CACA, CAMP, GABA, GABOB, N4-chloroacetylcytosine arabinoside, picamilon, progabide, tolgabide, and neuroactive steroids, such as allopregnanolone, THDOC, and alphaxolone | gabazine, gaboxadol, isonipecotic acid, SKF-97,541, and (1,2,5,6-Tetrahydropyridin-4-yl)methylphosphinic acid |

TABLE 7E

MUSCARINC AGONISTS AND ANTAGONISTS

| Receptor | Agonist | Antagonist |
|---|---|---|
| Chrm1 | AF102B, AF150(S), AF267B, acetylcholine, carbachol, cevimeline, muscarine, oxotremorine, pilocarpine, vedaclidine, 77-LH-28-1, CDD-0097, McN-A-343, L689,660, and xanomeline | atropine, dicycloverine, hyoscyamine, ipratropium, mamba toxin muscarinic toxin 7 (MT7), olanzapine, oxybutynin, pirenzepine, telenzepine, and tolterodine |
| Chrm2 | acetylcholine, methacholine, iper-8-naph, berbine, and (2S,2'R,3'S,5'R)-1-methyl-2-(2-methyl-1,3-oxathiolan-5-yl)pyrrolidine 3-sulfoxide methyl iodide | atropine, dicycloverine, hyoscyamine, otenzepad, AQRA-741, AFDX-384, thorazine, diphenhydramine, dimenhydrinate, ipratropium, oxybutynin, pirenzepine, methoctramine, tripitramine, gallamine, and tolterodine |
| Chrm3 | acetylcholine, bethanechol, carbachol, L689, 660, oxotremorine, pilocarpine, aceclidine, arecoline, and cevimeline | atropine, dicycloverine, hyoscyamine, alcidium bromide, 4-DAMP, darifenacin, DAU-5884, HL-031,120, ipratropium, J-104,129, oxybutynin, tiotropium, zamifenacin, and tolterodine |
| Chrm4 | acetylcholine, carbachol, and oxotremorine), and Chrm5 agonists (e.g., acetylcholine, milameline, sabcomeline | AFDX-384, dicycloverine, himbacine, mamba toxin 3, PD-102,807, PD-0298029, and tropicamide |
| Chrm5 | acetylcholine, milameline, sabcomeline | VU-0488130, xanomeline |
| Non-selective | | scopolamine, hydroxyzine, doxylamine, dicyclomine, flavoxate, cyclopentolate, atropine methonitrate, trihexyphenidyl/benzhexol, solifenacin, benzatropine, mebeverine, and procyclidine |

TABLE 7F

NICOTINIC AGONISTS AND ANTAGONISTS

| Receptor | Agonist | Antagonist |
|---|---|---|
| Chrna receptors | choline, acetylcholine, carbachol, methacholine, nicotine, varenicline tartrate, galantamine hydrobromide, | turbocurarine, bupropion, mecamylamine, 18-methozycoronaridine, |

TABLE 7F-continued

NICOTINIC AGONISTS AND ANTAGONISTS

| Receptor | Agonist | Antagonist |
|---|---|---|
| | suxamethonium chloride (succinylcholine chloride), epibatidine, iobeline, decamethonium, isopronicline/TC-1734/AZD3480 (TC-1734), AZD1446 (TC-6683), TC-5619, TC-5214, MEM 3454 (RG3487), ABT-894, ABT-560, EVP-6124, EVP-4473, PNU-282987, AR-R17779, SSR 189711, JN403, ABBF, PHA-543613, SEN12333, GTS-21/DMXB-A, AZD0328, A-582941, ABT-418, 5-iodo-A-85380, SIB-1765F, ABT-089, and ABT-594 | hexamethonium, trimethaphan, atraciurium, doxacurium, mivacurium, pancuronium, vecuronium, succinylcholine, dextromethorphan, neramexane, dextrophan, and 3-methoxymorphinan |

TABLE 7G

SEROTONIN AGONISTS AND ANTAGONISTS

| Receptor | Agonist | Antagonist |
|---|---|---|
| $5\text{-HT}_{1A}$ | azapirones, such as alnespirone, binosperone, buspirone, enilospirone, etapirone, geprione, ipsaprione, revospirone, zalospirone, perospirone, tiosperone, umespirone, and tandospirone; 8-OH-DPAT, befiradol, F-15,599, lesopitron, MKC-242, LY-283,284, osemozotan, repinotan U-92,016-A, RU-24969, 2C-B, 2C-E, 2C-T-2, aripiprazole, asenapine, bacoside, befiradol, brexpiprazole, bufotenin, cannabidiol, and fibanserin | pindolol, tertatolol, alprenolol, AV-965, BMY-7,378, cyanopindolol, dotarizine, flopropione, GR-46,611, iodocyanopindolol, isamoltane, lecozotan, mefway, methiothepin, methysergide, MPPF, NAN-190, oxprenolol, pindobind, propanolol, risperidone, robalzotan, SB-649,915, SDZ-216,525, spiperone, spiramide, spiroxatrine, UH-301, WAY-100,135, WAY-100,635, and xylamidine |
| $5\text{-HT}_{1B}$ | triptans, such as sumatriptan, rizatriptan, eletriptan, donitriptan, almotriptan, frovatriptan, avitriptan, zolmitriptan, and naratriptan; ergotamine, 5-carboxamidotryptamine, CGS-12066A, CP-93,129, CP-94,253, CP-122,288, CP-135,807, RU-24969, vortioxetine, ziprasidone, and asenapine | methiothepin, yohimbine, metergoline, aripiprazole, isamoltane, AR-A000002, SB-216,641, SB-224,289, GR-127,935, SB-236,057 |
| $5\text{-HT}_{1D}$ | triptans, such as sumatriptan, rizatriptan, and naratriptan; ergotamine, 5-(nonyloxy)tryptaime, 5-(t-butyl)-N-methyltryptamine, CP-286,601, PNU-109,291, PNU-142,633, GR-46611, L-694,247, L-772,405, CP-122,288, and CP-135,807 | ziprasidone, methiothepin, yohimbine, metergoline, ergotamine, BRL-15572, vortioxetine, GR-127,935, LY-310,762, LY-367,642, LY-456,219, and LY-456,220 |
| $5\text{-HT}_{1E}$ | BRL-54443, eletriptan | |
| $5\text{-HT}_{1F}$ | LY-334,370, 5-n-butyryloxy-DMT, BRL-54443, eletriptan, LY-344,864, naratriptan, and lasmiditan | |
| $5\text{-HT}_{2A}$ | 25I-NBOH, 25I-NBOMe, (R)-DOI, TCB-2, mexamine, O-4310, PHA-57378, OSU-6162, 25CN-NBOH, juncosamine, efavirenz, mefloquine, lisuride, and 2C-B | cyproheptadine, methysergide, quetiapine, nefazodone, olanzapine, asenapine, pizotifen, LY-367,265, AMDA, hydroxyzine, 5-MeO-NBpBrT, and niaprazine |
| $5\text{-HT}_{2B}$ | fenfluramine, pergolide, cabergoline, mefloquine, BW-723086, Ro60-0175, VER-3323, 6-APB, guanfacine, norfenfluramine, 5-MeO-DMT, DMT, mCPP, aminorex, chlorphentermine, MEM, MDA, LSD, psilocin, MDMA | agomelatine, aripiprazole, sarpogrelate, lisuride, tegaserod, metadoxine, RS-127,445, SDZ SER-082, EGIS-7625, PRX-08066, SB-200,646, SB-204,741, SB-206,553, SB-215,505, SB-228,357, LY-266,097, and LY-272,015 |
| $5\text{-HT}_{2C}$ | lorcaserin, lisuride, A-372,159, AL-38022A, CP-809,101, fenfluramine, mesulergine, MK-212, naphthylisopropylamine, norfenfluramine, ORG-12,962, ORG-37,684, oxaflozane, PNU-22395, | agomelatine, CPC, eltoprazine, etoperidone, fluoxetine, FR-260,010, LU AA24530, methysergide, nefazodone, norfluoxetine, O-desmethyltramadol, RS-102,221, SB-200,646, SB-221,284, SB-242,084, |

TABLE 7G-continued

SEROTONIN AGONISTS AND ANTAGONISTS

| Receptor | Agonist | Antagonist |
|---|---|---|
| | PNU-181731, lysergamides, phenethylamines, piperazines, tryptamines, Ro60-0175, vabicaserin, WAY-629, WAY-161,503, WAY-163,909, and YM-348 | SDZ SER-082, tramadol, and trazodone |
| 5-HT$_{2A/2C}$ | | ketanserin, risperidone, trazodone, mirtazapine, clozapine |
| 5-HT$_3$ | 2-methyl-5-HT, alpha-methyltryptamine, bufotenin, chlorophenylbiguanide, ethanol, ibogaine, phenylbiguanide, quipazine, RS-56812, SR-57227, varenicline, and YM-31636 | dolasetron, granisetron, ondansetron, palonosetron, tropisetron, alosetron, cilanosetron, mirtazapine, AS-8112, bantopride, metroclopramide, renzapride, zacopride, mianserin, vortioxetine, clozapine, olanzapine, quetiapine, menthol, thujone, lamotigrine, and 3-tropanyl indole-3-carboxylate |
| 5-HT$_4$ | cisapride, tegaserod, prucalopride, BIMU-8, CJ-033,466, ML-10302, mosapride, renzapride, RS-67506, RS-67333, SL65.1055, zacopride, metoclopramide, and sulpride | piboserod, GR-113,808, GR-125,487, RS-39604, SB-203,186, SB-204,070, and chamomile |
| 5-HT$_{5A}$ | valeronic acid | ASP-5736, AS-2030680, AS-2674723, latrepiridine, risperidone, and SB-699,551 |
| 5-HT$_6$ | EMDT, WAY-181,187, WAY-208,466, N-(inden-5-yl)imidazothiazole-5-sulfonamide, E-6837, E-6801, and EMD-386,088 | ALX-1161, AVN-211, BVT-5182, BVT-74316, cerlapiridine, EGIS-12233, idalopiridine, interpridine, latrepiridine, MS-245, PRX-07034, SB-258,585, SB-271,046, SB-357,134, SB-339,885, Ro 04-6790, Ro-4368554, sertindole, olanzapine, asenapine, clozapine, rosa rugosa extract, and WAY-255315 |
| 5-HT$_7$ | AS-19, 5-CT, 5-MeOT, 8-OH-DAPT, aripiprazole, E-55888, E-57431, LP-12, LP-44, MSD-5a, RA-7, and N,N-Dimethyltryptamine | amisulpride, amitriptyline, amoxapine, clomipramine, clozapine, DR-4485, fluphenazine, fluperlapine, ICI 169,369, imipramine, ketanserine, JNJ-18038683, loxapine, lurasidone, LY-215,840, maprotiline, methysergide, mesulergine, mianserin, olanzepine, pimozide, ritanserin, SB-258,719, SB-258,741, SB-269,970, SB-656,104-A, SB-691,673, sertindole, spiperone, tenilapine, TFMPP, vortioxetine, trifluoperazine, ziprasidone, and zotepine |
| Non-selective 5-HT antagonists | | chlorpromazine, cyproheptadine, pizotifen, oxetorone, spiperone, ritanserin, parachlorophenylalanine, metergoline, propranolol, mianserin, carbinoxamine, methdilazine, promethazine, pizotifen, oxatomide, feverfew, fenclonin, and reserpine |

TABLE 7H

GLUATAMATE RECEPTOR AGONISTS AND ANTAGONISTS

| Receptor | Agonist | Antagonist |
|---|---|---|
| Ionotropic (GRIA-14, GRIK1-5, and GRIN1-3B) | AMPA, glutamic acid, ibotenic acid, kainic acid, NMDA, quisqualic acid | AP5, AP7, CPPene, selfotel, HU-211, Huperzine A, gabapentin, remacemide, amantadine, atomoxetine, AZD6765, agmatine, chloroform, dextrallorphan, dextromethorphan, dextrorphan, diphenidine, dizocilpine (MK-801), ethanol, eticyclidine, gacyclidine, ibogaine, ifenprodil, ketamine, kynurenic acid, memantine, magnesium, methoxetamine, nitromemantine, nitrous oxide, PD-137889, perampanel, phencyclidine, |

TABLE 7H-continued

GLUTAMATE RECEPTOR AGONISTS AND ANTAGONISTS

| Receptor | Agonist | Antagonist |
|---|---|---|
| | | rolicyclidine, tenocyclidine, methoxydine, tiletamine, neramexane, eliprodil, etoxadrol, dexoxadrol, WMS-2539, NEFA, delucemine, 8A-PDHQ, aptiganel, rhynchophylline |
| Metabotropic (GRM1-8) | L-AP4, ACPD, L-QA, CHPG, LY-379,268, | AIDA, fenobam, MPEP, LY-367,385, EGLU, |
| Glycine antagonists | LY-354,740, ACPT, VU0155041 | CPPG, MAP4, MSOP, LY-341,495 rapastinel, NRX-1074, 7-chlorokynurenic acid, 4-chlorokynurenine, 5,7-dichlorokynurenic acid, kynurenic acid, TK-40, 1-aminocyclopropanecarboxylic acid (ACPC), L-phenylalanine, and xenon |

TABLE 7I

HISTAMINE AGONISTS AND ANTAGONISTS

| Receptor | Agonist | Antagonist |
|---|---|---|
| Non-selective | histamine dihydrochloride, HTMT dimaleate, 2-pyridylethlyamine dihydrochloride | |
| $H_1$ | | acrivastine, azelastine, astemizole, bilastine, bromodiphenhydramine, brompheniramine, buclizine, carbinoxamine, cetirizine, cetirizine dihydrochloride, clemastine fumarate, clemizole hydrochloride, chlorodiphenhydramine, chlorphenamine, chlorpromazine, clemastine, cyclizine, cyproheptadine, dexbrompheniramine, dexchlorpheniramine, dimenhydrinate, dimethindene maleate, dimetindene, diphenhydramine, diphenhydramine hydrochloride, doxepin hydrochloride, doxylamine, ebastine, embramine, fexofenadine, fexofenadine hydrochloride, hydroxyzine, ketotifen fumarate, loratadine, meclizine, meclizine dihydrochloride, mepyramine maleate, mirtazapine, olopatadine, olopatadine hydrochloride, orphenadrine, phenindamine, pheniramine, phenyltoloxamine, promethazine, quetiapine, rupatadine, terfenadine, tripelennamine, zotepine, trans-triprolidine hydrochloride, and triprolidine |
| $H_1$ inverse agonists | | cetirizine, levocetirizine, desloratadine, and pyrilamine |
| $H_2$ | betazole, impromidine, dimaprit dihydrochloride, and amthamine dihyrdobromide | aminopotentidine, cimetidine, famotidine, ICI 162,846, lafutidine, nizatidine, ranitidine, ranitidine hyrdochloride, roxatidine, zolantadine dimaleate, and toitidine |
| $H_3$ | imetit dihydropbromide, immepip dihyrdrobromide, immethridine dihydrobromide, α-Methylhistamine dihydrobromide, N-methylhistamine dihydrochloride, proxyfan oxalate, and betahistine | clobenpropit, clobenpropit dihydrobromide, A 3314440 dihyrdochloride, BF 2649 hydrochloride, carcinine ditrifluoroacetate, ABT-239, ciprofaxin, conessine, GT 2016, A-349,821, impentamine dihydrobromide, iodophenpropit dihydrobromide, JNJ 10181457 dihydrochloride, JNJ 5207852 dihydrochloride, ROS 234 dioxalate, SEN 12333, VUF 5681 dihydrobromide, and thioperamide |
| $H_4$ | imetit dihydropbromide, immepip dihyrdrobromide, 4-methylhistamine dihydrochloride, clobenpropit dihydrobromide, VUF 10460, and VUF 8430 dihydrobromide | thioperamide, JNJ 7777120, A 943931 dihydrochloride, A 987306, JNJ 10191584 maleate, and VUF-6002 |

TABLE 7J

CANNABINOID AGONISTS AND ANTAGONISTS

| Receptor | Agonist | Antagonist |
|---|---|---|
| Cannabinoid receptor (non-selective) | Anandamide, N-Arachidonoyl dopamine, 2-Arachidonoylglycerol (2-AG), 2-Arachidonyl glyceryl ether, Δ-9-Tetrahydrocannabinol, EGCG, Yangonin, AM-1221, AM-1235, AM-2232, UR-144, JWH-007, JWH-015, JWH-018, ACEA, ACPA, arvanil, CP 47497, DEA, leelamine, methanandamide, NADA, noladin ether, oleamide, CB 65, GP-1a, GP-2a, GW 405833, HU 308, JWH-133, L-759,633, L-759,656, LEI 101, MDA 19, and SER 601 | |
| $CB_1$ receptor | ACEA, ACPA, RVD-Hpα, (R)-(+)-methanandamide | rimonabant, cannabidiol, $Δ^9$-tetrahydrocannabivarin (THCV), taranabant, otenabant, surinabant, rosonabant, SLV-319, AVE1625, V24343, AM 251, AM 281, AM 6545, hemopressin, LY 320135, MJ 15, CP 945598, NIDA 41020, PF 514273, SLV 319, SR 1141716A, and TC-C 14G |
| $CB_2$ receptor | CB 65, GP 1a, GP 2a, GW 405833, HU 308, JWH 133, L-759,656, L-759,633, SER 601, LEI 101 | cannabidiol, $Δ^9$-tetrahydrocannabivarin (THCV), AM 630, COR 170, JTE 907, and SR 144528 |

TABLE 7K

PURINERGIC RECEPTOR AGONISTS AND ANTAGONISTS

| Receptor | Agonist | Antagonist |
|---|---|---|
| ADORA1 (P1 adenosine receptor) | Adenosine, N6-Cyclopentyladenosine, N6-3-methoxy1-4-hydroxybenzyl adenine riboside (B2), CCPA, tecadenoson, selodenoson, Certain Benzodiazepines and Barbiturates, 2'-MeCCPA, GR 79236, and SDZ WAG 994 | Caffeine, theophylline, 8-Cyclopentyl-1,3-dimethylxanthine (CPX), 8-Cyclopenty1-1,3-dipropylxanthine (DPCPX), 8-Pheny1-1,3-dipropylxanthine, bamifylline, BG-9719, BG09928, FK-453, FK838, rolofylline, N-0861, and PSB 36 |
| ADORA2A (P1 adenosine receptor) | Adenosine, N6-3-methoxyl-4-hydroxybenzyl adenine riboside (B2), YT-146, DPMA, UK-423,097, limonene, NECA, CV-3146, binodenoson, ATL-146e, CGS-21680, and Regadenoson | Caffeine, theophylline, istradefylline, SCH-58261, SCH-442,416, ATL-444, MSX-3, preladenant, SCH-412,348, VER-6623, VER-6947, VER-7835, vipadenant, and ZM-241,385 |
| ADORA2B (P1 adenosine receptor) | Adenosine, 5'-N-ethylcarboxamidoadenosine, BAY 60-6583, LUF-5835, NECA, (S)-PHPNECA, and LUF-5845 | Caffeine, theophylline, CVT-6883, ATL-801, compound 38, MRS-1706, MRS-1754, OSIP-339,391, PSB-603, PSB-0788, and PSB-1115 |
| ADORA3 (P1 adenosine receptor) | Adenosine, 2-(1-Hexynyl)-N-methyladenosine, CF-101 (IB-MECA), CF-102, 2-Cl-IB-MECA, CP-532,903, inosine, LUF-6000, and MRS-3558 | Caffeine, theophylline, MRS-1191, MRS-1220, MRS-1334, MRS-1523, MRS-3777, MRE3008F20, MRE3005F20, OT-7999, SSR161421, KF-26777, PSB-10, PSB-11, and VUF-5574 |
| P2Y receptor | ATP, ADP, UTP, UDP, UDP-glucose, 2-methylthioladenosine 5' diphosphate (2-MeSADP), lysophosphatidic acid, PSB 1114, PSB 0474, NF 546, MRS 2365, MRS 2690, MRS 2693, MRS 2768, MRS 2905, MRS 2957, MRS 4062, and denufosol ($P2Y_2$ agonist) | clopidogrel, elinogrel, prasugrel, ticlopidine, ticagrelor, AR-C 118925XX, AR-C 66096, AR-C 69931, AZD 1283, MRS 2179, MRS 2211, MRS 2279, MRS 2500, MRS 2578, NF 157, NF 340, PPADS, PPTN hydrochloride, PSD 0739, SAR 216471, and suramin |
| P2X receptor | ATP | A 438079, A 740003, A 804598, A 839977, AZ 10606120, AZ 11645373, 5-BDBD, BX 430, Evans Blue, JNJ 47965567, KN-62, NF 023, NF 110, NF 157, NF 279, NF 449, PPADS, iso-PPADS, PPNDS, Ro 0437626, Ro 51, RO-3, TC-P 262, suramin, TNP-ATP, and $P2X_7$ antagonists NF279, calmidazolium, and KN-62 |

TABLE 8

NEUROTRANSMISSION MODULATORS

| Type | Modulators |
| --- | --- |
| Norepinephrine reuptake inhibitors (increase adrenergic neurotransmission) | amedalin, atomoxetine, CP-39,332, daledalin, edivoxetine, esreboxetine, lortalamine, nisoxetine, reboxetine, talopram, talsupram, tandamine, viloxazine, bupropion, ciclazindol, manifaxine, maprotiline, radafaxine, tapentadol, teniloxazine, protriptyline, nortriptyline, and desipramine |
| Norepineprhine-dopamine reuptake inhibitors (increase adrenergic and dopamine neurotransmission) | amineptine, bupropion, desoxypipradrol, dexmethylphenidate, difemetorex, diphenylprolinol, ethylphenidate, fencamfamine, fencamine, lefetamine, methylenedioxy-pyrovalerone, methylphenidate, nomifensine, O-2172, oxolinic acid, pipradrol, prolintane, pyrovalerone, tametraline, and WY-46824 |
| Serotonin-norepinephrine-dopamine reuptake inhibitors (SNDRIs) and serotonin-norepinephrine reuptake inhibitors (SNRIs) (increase adrengergic, dopamine, and serotonin neurotransmission) | mazindol, nefazodone, sibutramine, venlafaxine, esketamine, duloxetine, ketamine, phencyclidine, tripelennamine, mepirazole, amitifadine, AN788, ansofaxine, centanafadine, atomoxetine, desvenlafaxine, milnacipran, levomilnacipran, dasotraline, Lu AA34893, Lu AA37096, NS-2360, tedatioxetine, tesofensine, bicifadine, BMS-866,949, brasofensine, diclofensine, DOV-216,303, EXP-561, liafensine, NS-2359, RG-7166, SEP-227,162, SEP-228,425, SEP-228,432, naphyrone, 3,3-Diphenylcyclobutanamine, 3,4-Dichlorotametraline, D-161, desmethylsertraline, DMNPC, DOV-102,677, fezolamine, GSK1360707F, indatraline, JNJ-7925476, JZ-IV-10, JZAD-IV-22, LR-5182, methylnaphthidate, MI-4,PRC200-SS, PRC050, PRCO25, SKF-83,959, TP1, phenyltropanes (e.g., WF-23, dichloropane, and RTI-55), Ginkgo biloba extract, St John's Wort, hyperforin, adhyperforin, and uliginosin B |
| Dopamine reuptake inhibitors (increase dopamine neurotransmission) | Dopamine reuptake inhbiitors (e.g., altropane, amfonelic acid, amineptine, BTCP, 3C-PEP, DBL-583, difluoropine, GBR-12783, GBR-12935, GBR-13069, GBR-13098, GYKI-52895, lometopane, methylphenidate, ethylphenidate, modafinil, armodafinil, RTI-229, vanoxerine, adrafinil, benztropine, bupropion, fluorenol, medifoxamine, metaphit, rimcazole, venlafaxine, Chaenomeles speciosa, and oroxylin A), dopamine releasing agents (e.g., p-Tyramine), dextroamphetamine, lisdexamfetamine, dexmethylphenidate, and cathinone |
| Dopamine prodrugs (increase dopamine neurotransmission) | Levopoda, docarpamine |
| GABA reuptake inhibitors (increase GABA neurotransmission) | CL-996, deramciclane, gabaculine, guvacine, nipecotic acid, NNC-711, NNC 05-2090, SKF-89976A, SNAP-5114, tiagabine, and hyperforin |
| GABA analogs (increase GABA neurotransmission) | gabapentin, butyric acid, valproic acid, valpromide, valnoctamide, 3-hydroxybutanal, GHB, sodium, oxybate, aceburic acid, GBL, GHBAL, GHV, GVL, GHC, GCL, HOCPCA, UMB68, pregabalin, tolibut, phaclofen, sacolfen, arecaidine, gaboxadol, isonipecotic acid, 3-Methyl-GABA, AABA, BABA, DAVA, GAVA, Glutamic acid, hopantenic acid, piracetam, and vigabatrin |
| GABA prodrugs (increase GABA neurotransmission) | L-Glutamine, N-Isonicotinoyl-GABA, picamilon, progabide, tolgabide |
| Acetylcholinesterase inhibitors (increase nicotinic and muscarinic neurotransmission) | carbamates, physostigmine, neostigmine, pyridostigmine, ambenonium, demecarium, rivastigmine, phenanthrene derivatives, galantamine, caffeine, rosmarinic acid, alpha-pinene, piperidines, donepezil, tacrine, edrophonium, Huperzine A, ladostigil, ungeremine, lactucopicrin, dyflos, echothiophate, parathion, and quasi-irreversible acetylcholinesterase inhibitors |
| Serotonin reuptake inhibitors (increase serotonin neurotransmission) | alaproclate, cericlamine, citalopram, dapoxetine, escitalopram, femoxetine, fluoxetine, fluvoxamine, ifoxetine, indalpine, omiloxetine, panuramine, paroxetine, pirandamine, RTI-353, sertraline, zimelidine, desmethylcitalopram, didesmethylcitalopram, seproxetine ((S)-norfluoxetine), desvenlafaxine, cianopramine, litoxetine, lubazodone, SB-649,915, trazodone, vilazodone, vortioxetine, dextromethorphan, dextropropoxyphene, dimenhydrinate, diphenhydramine, mepyramine (pyrilamine), mifepristone, delucemine, mesembrenone, mesembrine, roxindole, duloxetine, levomilnacipran, milnacipran, dapoxetine, sibutramine, chlorpheniramine, dextropmethorphan, and methadone |
| Serotonin releasing agents (increase serotonin neurotransmission) | chlorphentermine, cloforex, dexfenfluramine, etolorex, fenfluramine, flucetorex, indeloxazine, levofenfluramine, tramadol, carbamazepine, amiflamine (FLA-336), viqualine (PK-5078), 2-Methyl-3,4-methylenedioxyamphetamine (2-Methyl-MDA), 3-Methoxy-4-methylamphetamine (MMA), 3-Methyl-4,5-methylenedioxyamphetamine (5-Methyl-MDA), 3,4-Ethylenedioxy-N-methylamphetamine (EDMA), 4-Methoxyamphetamine (PMA), 4-Methoxy-N-ethylamphetamine (PMEA), 4-Methoxy-N-methylamphetamine (PMMA), 4-Methylthioamphetamine (4-MTA), 5-(2-Aminopropyl)-2,3-dihydrobenzofuran (5-APDB), 5-Indanyl-2-aminopropane (IAP), 5-Methoxy-6-methylaminoindane (MMAI), 5-Trifluoromethyl-2-aminoindane (TAI), 5,6-Methylenedioxy-2-aminoindane (MDAI), 5,6-Methylenedioxy-N-methyl-2-aminoindane (MDMAI), 6-Chloro-2-aminoindane (6-CAT), 6-Tetralinyl-2-aminopropane (TAP), 6,7-Methylenedioxy-2-aminotetralin (MDAT), 6,7-Methylenedioxy-N-methyl-2-aminotetralin (MDMAT), N-Ethyl-5-trifluoromethyl-2-aminoindane (ETAI), N-Methyl-5-indanyl-2-aminopropane, aminorex, MDMA, MDEA, MDA, MBDB, and tryptamines, such as DMT, αMT, 5MeO-NMT, NMT, NETP, Dimethyl-Serotonin, 5MeO-NET, αET and αMT |
| Excitatory amino acid reuptake inhibitors (increase Glutamate receptor neurotransmission) | didydrokanic acid, WAY-213,613, L-trans-2,4-PDC, amphetamine, and L-Theanine |
| Glycine reuptake inhibitors (increase Glutamate receptor neurotransmission) | bitopertin, Org 24598, Org 25935, ALX-5407, sacrosine, Org 25543, and N-arachidonylglycerine |
| Histidine decarboxylase inhibitors (decrease histamine neurotransmission) | Tritoqualine, catechin |
| Endocannabinoid enhancers (increase cannabinoid neurotransmission) | AM404, fatty acid amide hydrolase inhibitors (e.g., AM374, ARN2508, BIA 10-2472, BMS-469908, CAY-10402, JNJ-245, JNJ-1661010, JNJ-28833155, JNJ-40413269, JNJ-42119779, JNJ-42165279, MK-3168, MK-4409, MM-433593, OL-92, OL-135, PF-622, PF-750, PF-3845, PF-04457845, PF-04862853, RN-450, SA-47, SA-73, SSR-411298, ST-4068, TK-25, URB524, URB597, URB694, URB937, VER-156084, and V-158866 |
| Monoacylglycerol lipase inhibitors (increase cannabinoid neurotransmission) | N-arachidonoyl maleimide, JZL184 |
| Endocannabinoid transporter inhibitors(increase cannabinoid neurotransmission) | SB-FI-26 |
| Endocannabinoid reuptake | AM404, AM1172, LY-2183240, O-2093, OMDM-2, UCM-707, VDM-11, guineensine, |

TABLE 8-continued

NEUROTRANSMISSION MODULATORS

| Type | Modulators |
|---|---|
| inhibitors (increase cannabinoid neurotransmission) | ETI-T-24_B_I, WOBE437, and RX-055 |
| Adenosine uptake inhibitors (increase purinergic neurotransmission) | cilostazol, dilazep, and dipyramidole |
| Nucleoside transporter inhibitors (increase purinergic neurotransmission) | 8MDP, Decynium 22, 5-iodotubercidin, NBMPR, and TC-T 6000 |

In some embodiments, the neurotransmission blocker is a neurotoxin listed in Table 9, or a functional fragment or variant thereof. Neurotoxins include, without limitation, convulsants, nerve agents, parasympathomimetics, and uranyl compounds. Neurotoxins may be bacterial in origin, or fungal in origin, or plant in origin, or derived from a venom or other natural product. Neurotoxins may be synthetic or engineered molecules, derived de novo or from a natural product. Suitable neurotoxins include but are not limited to botulinum toxin and conotoxin. Exemplary neurotoxins are listed in Table 9.

TABLE 9

NEUROTOXINS

| NEUROTOXINS | |
|---|---|
| 2,4,5-Trihydroxyamphetamine | Grayanotoxin |
| 2,4,5-Trihydroxymethamphetamine | Hainantoxin |
| 3,4-Dichloroamphetamine | Halcurin |
| 5,7-Dihydroxytryptamine | Hefutoxin |
| 5-Iodowillardiine | Helothermine |
| Ablomin | Heteroscodratoxin-1 |
| Aconitine | Histrionicotoxin |
| Aconitum | Homoquinolinic acid |
| Aconitum anthora | Hongotoxin |
| AETX | Huwentoxin |
| Agelenin | Ibotenic acid |
| Agitoxin | Ikitoxin |
| Aldrin | inhibitor cystine knot |
| Alpha-Methyldopamine | Jingzhaotoxin |
| Alpha-neurotoxin | Kainic acid |
| Altitoxin | Kaliseptine |
| Anatoxin-a | Kappa-bungarotoxin |
| Androctonus australis hector insect toxin | Kodaikanal mercury poisoning |
| Anisatin | Kurtoxin |
| Anthopleurin | Latrotoxin |
| Antillatoxin | Lq2 |
| Anuroctoxin | Maitotoxin |
| Apamin | Margatoxin |
| Arum italicum | Maurotoxin |
| Arum maculatum | Mercury (element) |
| Babycurus toxin 1 | Methanol |
| Batrachotoxin | Methiocarb |
| BDS-1 | MPP+ |
| Bestoxin | MPTP |
| Beta-Methylamino-L-alanine | Nemertelline |
| BgK | Neosaxitoxin |
| Birtoxin | Nicotine |
| BmKAEP | N-Methylconiine |
| BmTx3 | Oenanthotoxin |
| BotIT2 | Oxalyldiaminopropionic acid |
| BotIT6 | Oxidopamine |
| Botulinum toxin | Oxotoxin |
| Brevetoxin | Pahutoxin |
| Bukatoxin | Palytoxin |
| Butantoxin | Pandinotoxin |
| Calcicludine | Para-Bromoamphetamine |

TABLE 9-continued

NEUROTOXINS

| NEUROTOXINS | |
|---|---|
| Calciseptine | Para-Chloroamphetamine |
| Calitoxin | Para-Chloromethamphetamine |
| Caramboxin | Para-Iodoamphetamine |
| Carbon disulfide | Penitrem A |
| CgNa toxin | Phaiodotoxin |
| Charybdotoxin | Phenol |
| Cicutoxin | Phoneutria nigriventer toxin-3 |
| Ciguatoxin | Phrixotoxin |
| Cll1 | Polyacrylamide |
| Clostridium botulinum | Poneratoxin |
| Conantokins | Psalmotoxin |
| Conhydrine | Pumiliotoxin |
| Coniine | Quinolinic acid |
| Conotoxin | Raventoxin |
| Contryphan | Resiniferatoxin |
| CssII | Samandarin |
| CSTX | Saxitoxin |
| Curare | Scyllatoxin |
| Cyanide poisoning | Sea anemone neurotoxin |
| Cylindrospermopsin | Slotoxin |
| Cypermethrin | SNX-482 |
| Delta atracotoxin | Stichodactyla toxin |
| Dendrotoxin | Taicatoxin |
| Dieldrin | Taipoxin |
| Diisopropyl fluorophosphates | Tamapin |
| Dimethylmercury | Tertiapin |
| Discrepin | Tetanospasmin |
| Domoic acid | Tetraethylammonium |
| Dortoxin | Tetramethylenedisulfotetramine |
| DSP-4 | Tetrodotoxin |
| Ergtoxin | Tityustoxin |
| Falcarinol | Tricresyl phosphate |
| Fenpropathrin | TsIV |
| Gabaculine | Vanillotoxin |
| Ginkgotoxin | Veratridine |
| Grammotoxin | |

Antibodies

Neurotransmission modulators also include antibodies that bind to neurotransmitters or neurotransmitter receptors listed in Tables 5 and 6 and decrease neurotransmission. These antibodies include blocking and neutralizing antibodies. Antibodies to neurotransmitters or neurotransmitter receptors listed in Tables 5 and 6 can be generated by those of skill in the art using well established and routine methods.

Neuronal Growth Factor Blocker

In some embodiments, the P2RX2 inhibitor is administered with a neuronal growth factor blocker (e.g., an agent that decreases neurogenic/axonogenic signals, e.g., an antagonist of a neurotrophic factor, neuronal growth factor, or neuronal growth factor receptor). For example, the neuronal growth factor blocker is an antagonist of a neuronal growth factor or neuronal growth factor receptor listed in Table 10. A neuronal growth factor blocker may decrease neurogenesis, neuronal growth, neuronal differentiation, neurite outgrowth, synapse formation, synaptic maturation, synaptic refinement, or synaptic stabilization. Neuronal growth factor blockers decrease tissue innervation (e.g., innervation of a tumor) and the formation of synaptic connections between two or more neurons and between neurons and non-neural cells. A neuronal growth factor blocker may block one or more of these processes (e.g., through the use of antibodies that block neuronal growth factors or their receptors or inhibitory RNAs directed to neuronal growth factors or their receptors). Neuronal growth factor blockers can decrease one of the above-mentioned processes by 10%, 20%, 30%, 40%, 50%, 60%, 70%, 80%, 90%, 95%, 98%, 200%, 500% or more.

In some embodiments, the neuronal growth factor blocker decreases neurogenic/axonogenic signals, e.g., the method includes administering to the subject or contacting a cell with a neuronal growth factor blocker in an amount and for a time sufficient to decrease neurogenesis, axonogenesis, or innervation. For example, the neuronal growth factor blocker that leads to a decrease in neurogenesis or axonogenesis is a blocking or neutralizing antibody against a neurotrophic factor. Relevant neurotrophic factors include NGF, BDNF, ProNGF, Sortilin, TGFβ and TGFβ family ligands and receptors (e.g., TGFβR1, TGFβR2, TGFβ1, TGFβ2 TGFβ4), GFRα family ligands and receptors (e.g., GFRα1, GFRα2, GFRα3, GFRα4, GDNF), CNTF, LIF, neurturin, artemin, persephin, neurotrophin, chemokines, cytokines, and others listed in Table 10. Receptors for these factors can also be targeted, as well as downstream signaling pathways including Jak-Stat inducers, and cell cycle and MAPK signaling pathways. In some embodiments, the neuronal growth factor blocker decreases neurogenesis, axonogenesis or any of the processes mentioned above by sequestering, blocking, antagonizing, degrading, or downregulating a neuronal growth factor or a neuronal growth factor receptor listed in Table 10. In some embodiments, the neuronal growth factor blocker decreases neurogenesis, axonogenesis or any of the processes mentioned above by blocking or antagonizing a signaling protein that is downstream of a neuronal growth factor. In some embodiments, the neuronal growth factor blocker decreases neurogenesis, axonogenesis or any of the processes mentioned above by blocking, disrupting, or antagonizing a synaptic or structural protein. Neurogenesis, axonogenesis, neuronal growth, neuronal differentiation, neurite outgrowth, synapse formation, synaptic maturation, synaptic refinement, synaptic stabilization, or tissue innervation can be decreased in the subject at least 1%, 2%, 5%, 10%, 15%, 20%, 25%, 30%, 35%, 40%, 50%, 60%, 70%, 80% or more, compared to before the administration. Neurogenesis, axonogenesis, neuronal growth, neuronal differentiation, neurite outgrowth, synapse formation, synaptic maturation, synaptic refinement, synaptic stabilization, or tissue innervation can be decreased in the subject between 5-20%, between 5-50%, between 10-50%, between 20-80%, between 20-70%. Neuronal growth factor blockers can be administered in any of the modalities described herein (e.g., antibody, small molecule, nucleic acid, polypeptide, or viral vector).

In some embodiments, the neuronal growth factor blocker decreases the number of nerves in an affected tissue. For example, the subject has cancer (e.g., the subject has a highly innervated tumor). For example, the neuronal growth factor blocker is administered in an amount and for a time sufficient to decrease neurogenesis/axonogenesis.

Neuronal growth factor blockers include antibodies that bind to neuronal growth factors or neuronal growth factor receptors and decrease their signaling (e.g., blocking antibodies). Exemplary neuronal growth factor blocking antibodies are listed below in Table 11. Antibodies to neuronal growth factors listed in Table 10 can also be generated by those of skill in the art using well established and routine methods.

TABLE 10

NEURONAL GROWTH FACTORS

| Gene | Type | Accession Number | Entrez Gene ID |
|---|---|---|---|
| ARTN | Ligand | Q5T4W7 | 9048 |
| BDNF | Ligand | P23560 | 627 |
| BDNF-AS | Ligand |  | 497258 |
| BEX1 | Signaling | Q9HBH7 | 55859 |
| BEX3 | Signaling | Q00994 | 27018 |
| CD34 | Receptor | P28906 | 947 |
| CDNF | Ligand | Q49AH0 | 441549 |
| CNTF | Ligand | P26441 | 1270 |
| CNTFR | Receptor | P26992 | 1271 |
| CRLF1 | Receptor | O75462 | 9244 |
| CSPG5 | Ligand | O95196 | 10675 |
| DCLK1 | Signaling | O15075 | 9201 |
| DISC1 | Signaling | Q9NRI5 | 27185 |
| DNAJC5 | Signaling | Q9H3Z4 | 80331 |
| DPYSL2 | Signaling | Q16555 | 1808 |
| DVL1 | Signaling | O14640 | 1855 |
| EFNA5 | Ligand | P52803 | 1946 |
| EGR3 | Signaling | Q06889 | 1960 |
| ENO2 | Signaling | P09104 | 2026 |
| EphA1 | Receptor | P21709 | 2041 |
| EphA10 | Receptor | Q5JZY3 | 284656 |
| EphA2 | Receptor | P29317 | 1969 |
| EphA3 | Receptor | P29320 | 2042 |
| EphA4 | Receptor | P29317 | 2043 |
| EphA5 | Receptor | P54756 | 2044 |
| EphA6 | Receptor | Q9UF33 | 285220 |
| EphA7 | Receptor | Q15375 | 2045 |
| EphA8 | Receptor | P29322 | 2046 |
| EphB1 | Receptor | P54762 | 2047 |
| EphB2 | Receptor | P29323 | 2048 |
| EphB3 | Receptor | P54753 | 2049 |
| EphB4 | Receptor | P54760 | 2050 |
| EphB6 | Receptor | O15197 | 2051 |
| ETBR2 | Receptor | O60883 | 9283 |
| FSTL4 | Receptor | Q6MZW2 | 23105 |
| GDNF | Ligand | P39905 | 2668 |
| GFRA1 | Receptor | P56159 | 2674 |
| GFRA2 | Receptor | O00451 | 2675 |
| GFRA3 | Receptor | O60609 | 2676 |
| GFRA4 | Receptor | Q9GZZ7 | 64096 |
| GPR37 | Receptor | O15354 | 2861 |
| GPRIN1 | Signaling | Q7Z2K8 | 114787 |
| GPRIN2 | Signaling | O60269 | 9721 |
| GPRIN3 | Signaling | Q6ZVF9 | 285513 |
| GRB2 | Signaling | P62993 | 2885 |
| GZF1 | Signaling | Q9H116 | 64412 |
| IFNA1 | Ligand | P01562 | 3439 |
| IGF1 | Ligand | P05019 | 3479 |
| IGF2 | Ligand | P01344 | 3481 |
| IL11RA | Receptor | Q14626 | 3590 |
| IL1B | Ligand | P01584 | 3553 |
| IL3 | Ligand | P08700 | 3562 |
| IL4 | Ligand | P05112 | 3565 |
| IL6 | Ligand | P05231 | 3569 |
| IL6R | Receptor | P08887 | 3570 |
| IL6ST | Signaling | P40189 | 3572 |
| INS | Ligand | P01308 | 3630 |
| L1CAM | Signaling | P32004 | 3897 |
| LIF | Ligand | P15018 | 3976 |
| LIFR | Receptor | P42702 | 3977 |
| MAGED1 | Signaling | Q9Y5V3 | 9500 |
| MANF | Ligand | P55145 | 7873 |
| NDNF | Ligand | Q8TB73 | 79625 |
| NENF | Ligand | Q9UMX5 | 29937 |
| NENFP1 | Ligand |  | 106480294 |
| NENFP2 | Ligand |  | 100129880 |
| NENFP3 | Ligand |  | 106481703 |
| NGF | Ligand | P01138 | 4803 |
| NGFR | Receptor | P08138 | 4804 |
| NRG1 | Ligand | Q02297 | 3084 |
| NRP1 | Receptor | O14786 | 8829 |
| NRTN | Ligand | Q99748 | 902 |
| NTF3 | Ligand | P20783 | 4908 |
| NTF4 | Ligand | P34130 | 4909 |
| NTRK1 | Receptor | P04629 | 4914 |

TABLE 10-continued

NEURONAL GROWTH FACTORS

| Gene | Type | Accession Number | Entrez Gene ID |
|---|---|---|---|
| NTRK2 | Receptor | Q16620 | 4915 |
| NTRK3 | Receptor | Q16288 | 4916 |
| PDPK1 | Signaling | Q15530 | 5170 |
| PEDF | Ligand | P36955 | 5176 |
| PLEKHH3 | Signaling | Q7Z736 | 79990 |
| PSAP | Ligand | P07602 | 5660 |
| PSEN1 | Signaling | P49768 | 5663 |
| PSPN | Ligand | O70300 | 5623 |
| PTN | Ligand | P21246 | 5764 |
| RELN | Ligand | P78509 | 5649 |
| RET | Signaling | P07949 | 5979 |
| ROR1 | Receptor | Q01973 | 4919 |
| ROR2 | Receptor | Q01974 | 4920 |
| RPS6KA3 | Signaling | P51812 | 6197 |
| SDC3 | Receptor | O75056 | 9672 |
| SEMA3E | Ligand | O15041 | 9723 |
| SERPINE2 | Ligand | P07093 | 5270 |
| SERPINF1 | Ligand | P36955 | 5176 |
| SHC1 | Signaling | P51812 | 6464 |
| SNTG1 | Biosynthesis | P07602 | 54212 |
| S0RCS1 | Receptor | O75056 | 114815 |
| SORCS2 | Receptor | O15041 | 57537 |
| SORCS3 | Receptor | P07093 | 22986 |
| SORT1 | Receptor | Q99523 | 6272 |
| SULF1 | Signaling | Q8IWU6 | 23213 |
| SULF2 | Signaling | Q8IWU5 | 55959 |
| TGFB1 | Ligand | P01137 | 7040 |
| TGFB2 | Ligand | P61812 | 7042 |
| TGFB3 | Ligand | P10600 | 7043 |
| TMEM158 | Receptor | Q8WZ71 | 25907 |
| TNF | Ligand | P01375 | 7124 |
| TPM3 | Receptor | P06753 | 7170 |
| VEGFA | Ligand | P15692 | 7422 |
| VEGFB | Ligand | P49765 | 7423 |
| VGF | Ligand | O15240 | 7425 |
| XCR1 | Receptor | P46094 | 2829 |
| ZN274 | Signaling | Q96GC6 | 10782 |

TABLE 11

NEURONAL GROWTH FACTOR ANTIBODIES

| Neuronal Growth Factor | Antibody | Company |
|---|---|---|
| BDNF | 3868 (agonist antibody) | Pfizer |
| BDNF | 29D7 (agonist antibody) | Pfizer |
| EphA3 | KB004 | KaloBios Pharmaceuticals, Inc. |
| IFNA1 | Faralimomab | Creative Biolabs |
| IFNA1 | Sifalimumab (MEDI-545) | MedImmune |
| IFNA1 | Rontalizumab | Genentech |
| IGF | Figitumumab (CP-751,871) - an IGR-1R MAb | Pfizer |
| IGF | SCH717454 (Robatumamab, inhibits IGF initiated phosphorylation) | Merck |
| IGF | Cixutumumab (IGF-1R antibody) | Eli Lilly |
| IGF | Teprotumumab (IGF-1R blocking antibody) | Genmab/Roche |
| IGF-2 | Dusigitumab | MedImmune/AstraZeneca |
| IGF-2 | DX-2647 | Dyax/Shire |
| IGF | Xentuzumab | Boehringer Ingelheim/Eli Lilly |
| IGF | Dalotuzumab (IGFR1 blocking antibody) | Merck & Co. |
| IGF | Figitumumab (IGFR1 blocking antibody) | Pfizer |
| IGF | Ganitumab (IGFR1 blocking antibody) | Amgen |
| IGF | Robatumumab (IGFR1 blocking antibody) | Roche/Schering-Plough |
| IL1B | Canakinumab | Novartis |
| IL1B | APX002 | Apexigen |
| IL1B | Gevokizumab | XOMA |
| IL4 | Pascolizumab | GlaxoSmithKline |
| IL4 | Dupilumab | Regeneraon/Sanofi |
| IL6 | Siltuximab | Janssen Biotech, Inc. |
| IL6 | Olokizumab | UCB/R-Pharm |
| IL6 | Elsilimomab | Orphan Pharma International |
| IL6 | Sirukumab | Centocor |
| IL6 | Clazakizumab | Bristol Myers Squib/Alder Biopharmaceuticals |
| IL6 | Gerilimzumab (ARGX-109) | arGEN-X/RuiYi |
| IL6 | FE301 | Ferring Pharmaceuticals |
| IL6 | FM101 | Femta Pharmaceuticals |
| IL-6R | Sarilumab (directed against IL6R) | Regeneron/Sanofi |
| IL-6R | Tocilizumab | Hoffmann-La Roche/Chugai |
| IL-6R | Sapelizumab | Chugai |
| IL-6R | Vobarilizumab | Ablynx |
| L1CAM | AB417 | Creative biolabs |
| L1CAM | L1-9.3 | Creative biolabs |
| L1CAM | L1-14.10 | Biolegend |
| NGF | Tanezumab | Pfizer |
| NGF | Fulranumab (JNJ-42160443), | Amgen |
| NGF | MNAC13 (anti-TrkA, the NGF receptor) | Creative Biolabs |
| NGF | mAb 911 | Rinat/Pfizer |
| NGF | Fasinumab | Regeneron/Teva |
| NRG1 | 538.24 | Hoffman-La Roche |
| NRP1 | Vesencumab | Genentech/Roche |
| ROR1 | Cirmtuzumab | Oncternal Therapeutics |
| SAP | GSK2398852 | GlaxoSmithKline |
| TGFβ | Fresolimumab (pan-TGFβ antibody) | Genzyme/Aventis |
| TGFβ | IMC-TR1 (LY3022859) (MAb against TGFβRII) | Eli Lilly |
| TGFβ | TβM1 (anti-TGFβ1 MAb) | Eli Lilly |
| TGFβ2 | Lerdelimumab (CAT-152) | Genzyme |
| TGFβ1 | Metelimumab | Genzyme |
| TGFβ1 | LY2382770 | Eli Lilly |
| TGFβ | PF-03446962 (MAb against TGFβRI) | Pfizer |
| TNF | Infliximab | Janssen Biotech, Inc. |
| TNF | Adalimumab | AbbVie Inc. |
| TNF | Certolizumab pegol | UCB |
| TNF | Golimumab | Janssen Biotech, Inc. |
| TNF | Afelimomab | |
| TNF | Placulumab | Teva Pharmaceutical Industries, Inc. |
| TNF | Nerelimomab | Chiron/Celltech |
| TNF | Ozoralizumab | Pfizer/Ablynx |
| VEGFA | Bevacizumab | Genentech |
| VEGFA | Ranibizumab | Genentech |
| VEGF | Alacizumab pegol (anti-VEGFR2) | UCB |
| VEGFA | Brolucizumab | Novartis |
| VEGF | Icrucumab (anti-VEGFR1) | Eli Lilly |
| VEGF | Ramucirumab (anti-VEGFR2) | Eli Lilly |

Neuronal growth factor blockers also include agents that antagonize neuronal growth factors and neuronal growth factor receptors. For example, neuronal growth factor blockers include TNF inhibitors (e.g., etanercept, thalidomide, lenalidomide, pomalidomide, pentoxifylline, bupropion, and DOI), TGFβ1 inhibitors, (e.g., disitertide (P144)), and TGFβ2 inhibitors (e.g., trabedersen (AP12009)). Exemplary neuronal growth factor antagonists are listed in Table 12.

TABLE 12

NEURONAL GROWTH FACTOR AGONISTS AND ANTAGONISTS

| | Agonist | Antagonist |
|---|---|---|
| TrkA | NGF, amitriptyline, and gambogic amide, gambogic acid | ALE-0540 |
| TrkB | BDNF, NT3, NT4, 3,7-Dihydroxyflavone, 3,7,8,2-Tetrahydroxyflavone, 4'-Dimethylamino-7,8-dihydroxyflavone, 7,3'-Dihydroxyflavone, 7,8-Dihydroxyflavone, 7,8,2'-Trihydroxyflavone, 7,8,3'-Trihydroxyflavone, Amitriptyline, Deoxygedunin, Diosmetin, HIOC, LM22A-4, N-Acetylserotonin, Norwogonin (5,7,8-THF), R7, LM22A4, and TDP6 | ANA-12, cyclotraxin B, and gossypetin |
| Pan-Trk receptor | | entrectinib (RXDX-101), AG 879, GNF 5837, GW 441756, and PF 06273340 |
| GFRα1R | GDNF and XIB4035 | |
| VEGF receptor | | AEE 788, AG 879, AP 24534, axitinib, DMH4, GSK 1363089, Ki 8751, RAF 265, SU 4312, SU 5402, SU 5416, SU 6668, sunitinib, toceranib, vatalanib, XL 184, ZM 306416, and ZM 323881 |
| TGFβRI | | galunisertib (LY2157299), TEW-7197, SB-431542, A 83-01, D 4476, GW 788388, LY 364947, R 268712, RepSox, SB 505124, SB 525334, and SD 208 |

In any of the combination therapy approaches described herein, the first and second therapeutic agent (e.g., a P2RX2 inhibitor described herein and the additional therapeutic agent) are administered simultaneously or sequentially, in either order. The first therapeutic agent may be administered immediately, up to 1 hour, up to 2 hours, up to 3 hours, up to 4 hours, up to 5 hours, up to 6 hours, up to 7 hours, up to, 8 hours, up to 9 hours, up to 10 hours, up to 11 hours, up to 12 hours, up to 13 hours, 14 hours, up to hours 16, up to 17 hours, up 18 hours, up to 19 hours up to 20 hours, up to 21 hours, up to 22 hours, up to 23 hours up to 24 hours or up to 1-7, 1-14, 1-21 or 1-30 days before or after the second therapeutic agent.

Diagnosis and Prognosis of P2RX2-Associated Cancer

The methods described herein include methods of diagnosing or identifying patients with P2RX2-associated cancer. Subjects who can be diagnosed or identified as having P2RX2-associated cancer are subjects who have cancer (e.g., subjects identified as having cancer), or subjects suspected of having cancer. Subjects can be diagnosed or identified as having P2RX2-associated cancer based on screening of patient cancer samples (e.g., tumor biopsies). P2RX2 expression can be assessed in a cancer sample isolated from a subject using standard techniques known in the art, such as immunohistochemistry, western blot analysis, quantitative RT-PCR, RNA sequencing, fluorescent in situ hybridization, cDNA microarray, and droplet digital PCR. P2RX2 expression can be assessed by comparing measurements obtained from subject cancer samples to measurements of P2RX2 expression obtained from a reference sample (e.g., a non-cancerous cell of the same type or a cell that does not express P2RX2). Reference samples can be obtained from healthy subjects (e.g., subjects without cancer), or they can be obtained from databases in which average measurements of P2RX2 expression are cataloged for a variety of types of healthy (e.g., non-cancerous) cells from many subjects.

Subjects are diagnosed or identified as having P2RX2-associated cancer if P2RX2 expression is elevated in the cancer sample compared to the reference sample. An increase of P2RX2 expression of 1.1-fold or more (e.g., 1.1, 1.2, 1.3, 1.4, 1.5, 2.0, 2.5, 3.0, 3.5, 4.0, 4.5, 5.0, 6.0, 7.0, 8.0, 9.0, 10.0-fold or more) in the cancer sample compared to the reference indicates that the subject has P2RX2-associated cancer. Subjects can also be diagnosed or identified as having P2RX2-associated cancer (e.g., a cancer in which P2RX2 is functional) by contacting a cancer cell or tumor sample (e.g., biopsy) isolated from the subject with a P2RX2 agonist (e.g., ATP) and evaluating intracellular calcium using a calcium sensitive dye. An increase in intracellular calcium by 10% or more (e.g., 10%, 15%, 20%, 25%, 30%, 40%, 50%, 60%, 70%, 80%, 90%, 99%, or more) indicates that the tumor or cancer cell expresses functional P2RX2 (e.g., is a P2RX2-associated cancer). The tumor sample or cancer cell can then optionally be contacted with a P2RX2 inhibitor or P2RX2-specific inhibitor to determine whether the increase in intracellular calcium by a P2RX2 agonist (e.g., ATP) is reduced or blocked. Subjects diagnosed or identified as having P2RX2-associated cancer can be treated with the methods and compositions described herein (e.g., P2RX2 inhibitors). Subjects can also be selected for treatment with the methods and compositions described herein if the cancer sample from the subject is found to express P2RX2.

The methods described herein also include methods of predicting patient response (e.g., the response of cancer in a subject) to P2RX2 inhibitors in order to determine whether P2RX2 inhibitors can be used for cancer treatment. In some embodiments, a cancer sample (e.g., a tumor biopsy or cancer cell) is isolated from a subject and contacted with one or more P2RX2 inhibitors or P2RX2-specific inhibitors (e.g., cancer samples are cultured and contacted with one or more inhibitors in vitro). The response of the cancer sample to the one or more P2RX2 inhibitors or P2RX2-specific inhibitors is evaluated to predict response to treatment. Responses that are evaluated include cancer cell or tumor growth, cancer cell or tumor proliferation, cancer cell or tumor migration, cancer cell or tumor metastasis, cancer cell or tumor invasion, cancer cell or tumor death, cancer cell or tumor autophagy, or cancer cell or tumor P2RX2 expression. A decrease of at least 5% or more (e.g., 5%, 10%, 15%, 20%, 25%, 30%, 40%, 50%, 60%, 70%, 80%, 90%, 99%, or more) in cancer cell or tumor growth, cancer cell or tumor proliferation, cancer cell or tumor migration, cancer cell or tumor metastasis, cancer cell or tumor invasion, or cancer cell or tumor P2RX2 expression in treated cells compared to untreated or control-treated cells, or an increase of at least 5% or more (e.g., 5%, 10%, 15%, 20%, 25%, 30%, 40%, 50%, 60%, 70%, 80%, 90%, 99%, or more) in cancer cell or tumor death or cancer cell or tumor autophagy in treated cells compared to untreated or control-treated cells indicates that the cancer would respond to treatment with a P2RX2 inhibitor.

The methods used above to diagnose or identify a subject with P2RX2-associated cancer can also be used to predict patient response (e.g., the response of cancer in a subject) to treatment with a P2RX2 inhibitor. If the expression of P2RX2 is elevated in a cancer sample compared to a reference (e.g., 1.1, 1.2, 1.3, 1.4, 1.5, 2.0, 2.5, 3.0, 3.5, 4.0, 4.5, 5.0, 6.0, 7.0, 8.0, 9.0, 10.0-fold or more higher in the cancer sample compared to the reference), the subject can be predicted to respond to treatment with a P2RX2 inhibitor. Subjects predicted to respond to treatment with a P2RX2 inhibitor or P2RX2-specific inhibitor can be treated using the methods and compositions described herein (e.g., P2RX2 inhibitors).

Methods of Treatment

Administration

An effective amount of a P2RX2 inhibitor described herein for treatment of cancer can be administered to a subject by standard methods. For example, the agent can be administered by any of a number of different routes including, e.g., intravenous, intradermal, subcutaneous, percutaneous injection, oral, transdermal (topical), or transmucosal. The P2RX2 inhibitor can be administered orally or administered by injection, e.g., intramuscularly, or intravenously. The most suitable route for administration in any given case will depend on the particular agent administered, the patient, the particular disease or condition being treated, pharmaceutical formulation methods, administration methods (e.g., administration time and administration route), the patients age, body weight, sex, severity of the diseases being treated, the patient's diet, and the patient's excretion rate. The agent can be encapsulated or injected, e.g., in a viscous form, for delivery to a chosen site, e.g., a tumor site. The agent can be provided in a matrix capable of delivering the agent to the chosen site. Matrices can provide slow release of the agent and provide proper presentation and appropriate environment for cellular infiltration. Matrices can be formed of materials presently in use for other implanted medical applications. The choice of matrix material is based on any one or more of: biocompatibility, biodegradability, mechanical properties, and cosmetic appearance and interface properties. One example is a collagen matrix.

The agent (e.g., P2RX2 inhibitor, e.g., polypeptide, small molecule, nucleic acid, or antibody) can be incorporated into pharmaceutical compositions suitable for administration to a subject, e.g., a human. Such compositions typically include the agent and a pharmaceutically acceptable carrier. As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances are known. Except insofar as any conventional media or agent is incompatible with the active compound, such media can be used in the compositions of the invention. Supplementary active compounds can also be incorporated into the compositions.

A pharmaceutical composition can be formulated to be compatible with its intended route of administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a P2RX2 inhibitor described herein) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated are used in the formulation. Such penetrants are generally known, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions (including liposomes targeted to infected cells with monoclonal antibodies to viral antigens) can also be used as pharmaceutically acceptable carriers. These can be prepared according to methods known to those skilled in the art.

Nucleic acid molecule agents described herein can be administered directly (e.g., therapeutic mRNAs) or inserted into vectors used as gene therapy vectors. Gene therapy vectors can be delivered to a subject by, for example, intravenous injection, local administration (see U.S. Pat. No. 5,328,470) or by stereotactic injection (see, e.g., Chen et al., PNAS 91:3054 1994). The pharmaceutical preparation of the gene therapy vector can include the gene therapy vector in an acceptable diluent, or can include a slow release matrix in which the gene delivery vehicle is embedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Methods of formulating pharmaceutical agents are known in the art, e.g., Niazi, Handbook of Pharmaceutical Manufacturing Formulations (Second Edition), CRC Press 2009, describes formulation development for liquid, sterile, compressed, semi-compressed and OTC forms. Transdermal and mucosal delivery, lymphatic system delivery, nanoparticles, controlled drug release systems, theranostics, protein and peptide drugs, and biologics delivery are described in Wang et al., Drug Delivery: Principles and Applications (Second Edition), Wiley 2016; formulation and delivery of peptide and protein agent is described, e.g., in Banga, Therapeutic Peptides and Proteins: Formulation, Processing, and Delivery Systems (Third Edition), CRC Press 2015.

Local Administration

The P2RX2 inhibitors described herein can be administered locally, e.g., to the site of cancer in the subject. Examples of local administration include epicutaneous, inhalational, intra-articular, intrathecal, intravaginal, intravitreal, intrauterine, intra-lesional administration, lymph node administration, intratumoral administration and administration to a mucous membrane of the subject, wherein the administration is intended to have a local and not a systemic effect. As an example, for the treatment of a cancer described herein, the P2RX2 inhibitor may be administered locally (e.g., intratumorally) in a compound-impregnated substrate such as a wafer, microcassette, or resorbable sponge placed in direct contact with the affected tissue. Alternatively, the P2RX2 inhibitor is infused into the brain or cerebrospinal fluid using standard methods. As yet another example, a pulmonary cancer described herein may be treated, for example, by administering the P2RX2 inhibitor locally by inhalation, e.g., in the form of an aerosol spray from a pressured container or dispenser which contains a suitable propellant, e.g., a gas such as carbon dioxide or a nebulizer. A P2RX2 inhibitor for use in the methods described herein can be administered at the site of a tumor, e.g., intratumorally. In certain embodiments, the agent is administered to a mucous membrane of the subject.

Combination Therapy

The P2RX2 inhibitors described herein may be administered in combination with one or more additional therapies (e.g., 1, 2, 3 or more additional therapeutic agents). The two or more agents can be administered at the same time (e.g., administration of all agents occurs within 15 minutes, 10 minutes, 5 minutes, 2 minutes or less). The agents can also be administered simultaneously via co-formulation. The two or more agents can also be administered sequentially, such that the action of the two or more agents overlaps and their combined effect is such that the reduction in a symptom, or other parameter related to the disorder is greater than what would be observed with one agent or treatment delivered alone or in the absence of the other. The effect of the two or more treatments can be partially additive, wholly additive, or greater than additive (e.g., synergistic). Sequential or substantially simultaneous administration of each therapeutic agent can be effected by any appropriate route including, but not limited to, oral routes, intravenous routes, intramuscular routes, local routes, and direct absorption through mucous membrane tissues. The therapeutic agents can be administered by the same route or by different routes. For example, a first therapeutic agent of the combination may be administered by intravenous injection while a second therapeutic agent of the combination can be administered locally in a compound-impregnated microcassette. The first therapeutic agent may be administered immediately, up to 1 hour, up to 2 hours, up to 3 hours, up to 4 hours, up to 5 hours, up to 6 hours, up to 7 hours, up to, 8 hours, up to 9 hours, up to 10 hours, up to 11 hours, up to 12 hours, up to 13 hours, 14 hours, up to hours 16, up to 17 hours, up 18 hours, up to 19 hours up to 20 hours, up to 21 hours, up to 22 hours, up to 23 hours up to 24 hours or up to 1-7, 1-14, 1-21 or 1-30 days before or after the second therapeutic agent.

For use in treating cancer, the second agent may be a checkpoint inhibitor, a chemotherapeutic drug, a biologic drug, a non-drug therapy, a neurotransmission blocker, or a neuronal growth factor blocker. In one embodiment, the inhibitor of checkpoint is an inhibitory antibody (e.g., a monospecific antibody such as a monoclonal antibody). The antibody may be, e.g., humanized or fully human. In other embodiments, the inhibitor of checkpoint is a fusion protein, e.g., an Fc-receptor fusion protein. In some embodiments, the inhibitor of checkpoint is an agent, such as an antibody, that interacts with a checkpoint protein. In other embodiments, the inhibitor of checkpoint is an agent, such as an antibody, that interacts with the ligand of a checkpoint protein. In one embodiment, the inhibitor of checkpoint is an inhibitor (e.g., an inhibitory antibody or small molecule inhibitor) of CTLA-4 (e.g., an anti-CTLA4 antibody such as ipilimumab or tremelimumab). In one embodiment, the inhibitor of checkpoint is an inhibitor (e.g., an inhibitory antibody or small molecule inhibitor) of PD-1 (e.g., nivolumab; pembrolizumab; pidilizumab/CT-011). In one embodiment, the inhibitor of checkpoint is an inhibitor (e.g., an inhibitory antibody or small molecule inhibitor) of PDL1 (e.g., MPDL3280A/RG7446; MEDI4736; MSB0010718C; BMS 936559). In one embodiment, the inhibitor of checkpoint is an inhibitor (e.g., an inhibitory antibody or Fc fusion or small molecule inhibitor) of PDL2 (e.g., a PDL2/Ig fusion protein such as AMP 224). In one embodiment, the inhibitor of checkpoint is an inhibitor (e.g., an inhibitory antibody or small molecule inhibitor) of B7-H3 (e.g., MGA271), B7-H4, BTLA, HVEM, TIM3, GAL9, LAGS, VISTA, KIR, 2B4, CD160, CGEN-15049, CHK 1, CHK2, A2aR, B-7 family ligands, or a combination thereof. The second agent may also be an anti-angiogenic drug, e.g., an anti-VEGF antibody, or the second agent may be an oncolytic agent e.g., a chemotherapy, a drug that targets cancer metabolism, an antibody that marks a cancer cell surface for destruction, e.g., rituximab or trastuzumab, an antibody-drug conjugate, e.g., trastuzumab emtansine, a cell therapy, or other commonly-used anti-neoplastic agent.

Dosing

Subjects that can be treated as described herein are subjects with cancer or at risk of developing cancer. The cancer may be a primary tumor or a metastasized tumor. In some embodiments, the cancer is a P2RX2-associated cancer. Subjects who can be treated with the methods disclosed herein include subjects who have had one or more tumors resected, received chemotherapy or other pharmacological treatment for the cancer, received radiation therapy, and/or received other therapy for the cancer. Subjects who have never previously been treated for cancer can also be treated using the methods described herein.

In some embodiments, the agent is administered in an amount and for a time effective to result in one of (or more, e.g., 2 or more, 3 or more, 4 or more of): (a) reduced tumor size, (b) reduced rate of tumor growth, (c) increased tumor cell death (d) reduced tumor progression, (e) reduced number of metastases, (f) reduced rate of metastasis, (g) reduced tumor migration, (h) reduced tumor invasion, (i) reduced tumor volume, (j) decreased tumor recurrence, (k) increased survival of subject, (l) increased progression free survival of subject.

The methods described herein may include a step of selecting a treatment for a patient. The method includes (a) identifying (e.g., diagnosing) a patient who has cancer or is at risk of developing cancer, and (b) selecting a P2RX2 inhibitor, e.g., a P2RX2 inhibitor described herein, to treat the condition in the patient. In some embodiments, the method includes administering the selected treatment to the subject. In some embodiments, a patient is identified as having cancer based on imaging (e.g., MRI, CT, or PET scan), biopsy, or blood sample (e.g., detection of blood antigen markers, circulating tumor DNA (e.g., by PCR). In some embodiments, a patient is identified as having cancer after presenting with one or more symptoms of a paraneoplastic syndrome (e.g., fever, auto-antibodies directed against nervous system proteins, ataxia, dizziness, nystagmus, difficulty swallowing, loss of muscle tone, loss of fine motor coordination, slurred speech memory loss, vision loss, sleep disturbances, dementia, seizures, dysgeusia, cachexia, anemia, itching, or sensory loss in the limbs). In some embodiments, a patient presents with symptoms of paraneoplastic syndrome and is then identified as having cancer based on imaging (e.g., CT, MRI, or PET scans).

The method may also include (a) identifying (e.g., diagnosing) a patient who has a neoplasm, (b) optionally evaluating the neoplasm for innervation, and (c) selecting a P2RX2 inhibitor (e.g., a P2RX2 inhibitor described herein) to treat the patient if the neoplasm is highly innervated (e.g., if the level of innervation is at least 10% higher (e.g., at least 20%, 30%, 40%, 50%, 60%, 70%, 80% higher) than the level of innervation in control tissue, e.g., non-cancerous tissue of the same subject). Innervation may be measured by staining tissue sections for neural markers e.g., immunohistochemical staining for tyrosine hydroxylase, vesicular acetylcholine transporter; NGF-Inducible Large External glycoprotein, choline acetyltransferase, parvalbumin, neurofilament protein, Synapsin, synaptophysin, NeuN, NSE, MAP2, Beta III tubulin, 160 kD Neurofilament medium/200 kD Neurofilament Heavy, NSE, PSD93/PSD95, Doublecortin (DCX), c-fos, PSA-NCAM, NeuroD or Beta2, Tau, Calbindin-D28k, Calretinin, Neurofilament Protein (NFP), Glial fibrillary acidic protein (GFAP), S100β, Vimentin and CNPase; or by staining tissue sections with cell-identifying stains, e.g., H&E stain, Nissl Stain, Cresyl violet, Neutral red, Thionine and Toluidine blue, Luxol Fast blue stain, Weigert's Chromium hematoxylin method, Page's iron-eriochrome cyanine R, Dextran Conjugates (Fluorescein, Tetramethylrhodamine, Texas Red, Rhodamine Green), Hydrazides & Biocytins, Isolectin GS-IB4 conjugates, Golgi silver stain, or myelin stain; or by imaging the nervous system, e.g., by MRI, CT, PET, EEG, EMG, Myelogram, or magnetoencephalography. In some embodiments, the neoplasm is selected from: head and neck squamous cell carcinoma, adenoid cystic carcinoma, lymphoma, rhabdomyosarcoma, biliary tract cancer, gastric cancer, pancreatic cancer, prostate cancer, lung cancer, breast cancer, skin cancer (e.g., melanoma), renal cell carcinoma, or colorectal cancer. In some embodiments, the cancer is a cancer listed in Table 4. In some embodiments, the neoplasm is derived from a secretory tissue, glandular tissue, or endocrine or hormonal tissue.

In one embodiment, the method includes (a) identifying (e.g., diagnosing) a patient who has a neoplasm, (b) optionally evaluating the neoplasm for perineural invasion, and (c) selecting a P2RX2 inhibitor to treat the patient if the neoplasm exhibits perineural invasion. In some embodiments, the neoplasm is selected from: head and neck squamous cell carcinoma, adenoid cystic carcinoma, lymphoma, rhabdomyosarcoma, biliary tract cancer, gastric cancer, pancreatic cancer, and prostate cancer.

In one embodiment, the method includes (a) identifying (e.g., diagnosing) a patient who has a neoplasm, (b) optionally evaluating the subject for metastasis to brain or spinal cord, and (c) selecting a P2RX2 inhibitor to treat the patient if the neoplasm exhibits metastasis to brain or spinal cord. In some embodiments, the neoplasm is a lung cancer, breast cancer, skin cancer (e.g., melanoma), lymphoma, renal cell carcinoma, GI tract cancer, prostate cancer, or colorectal cancer.

In one embodiment, the method includes (a) identifying (e.g., diagnosing) a patient who has cancer, (b) optionally evaluating the subject for P2RX2 expression (e.g., overexpression), and (c) selecting a P2RX2 inhibitor to treat the patient if the cancer exhibits P2RX2 expression (e.g., overexpression, e.g., if the patient has P2RX2-associated cancer). In some embodiments, the neoplasm is a melanoma, small cell lung cancer, non-small cell lung cancer, gastric cancer, colorectal cancer, head and neck cancer, ovarian cancer, testicular cancer, thymoma, uterine cancer, kidney cancer, acute myeloid leukemia, diffuse large B-cell lymphoma, prostate cancer, breast cancer, or hepatocellular carcinoma. P2RX2 amplification and/or expression can be measured in a cancer sample collected from a subject using standard techniques known in the art, such as immunohistochemistry, western blot analysis, quantitative RT-PCR, RNA sequencing, fluorescent in situ hybridization, cDNA microarray, and droplet digital PCR. A cancer sample can be evaluated for increased expression and/or amplification of P2RX2 by comparison to a reference sample (e.g., a non-cancerous cell of the same type).

In some embodiments, the method includes administering the selected treatment to the subject.

The method may also include a step of assessing the subject for a parameter of cancer progression or remission, e.g., assessing the subject for one or more (e.g., 2 or more, 3 or more, 4 or more) of: primary tumor size (e.g., by imaging), number of metastases (e.g., by imaging or biopsy), cell death in situ (e.g., by biopsy), blood antigen markers (e.g., by ELISA), circulating tumor DNA (e.g., by PCR), or function of the affected organ (e.g., by a test of circulating enzymes for liver, albuminuria for kidney, lung capacity for lung, etc.).

In some embodiments, the tumor is treated with a P2RX2 inhibitor and a second therapeutic agent. The second therapeutic agent can be selected based on tumor type, tumor tissue of origin, tumor stage, tumor innervation, or mutations in genes expressed by the tumor.

In certain embodiments, a P2RX2 inhibitor administered according to the methods described herein does not have a direct effect on the central nervous system (CNS) or gut. Any effect on the CNS or gut is reduced compared to the effect observed if the P2RX2 inhibitor is administered directly to the CNS or gut. In some embodiments, direct effects on the CNS or gut are avoided by modifying the P2RX2 inhibitor not to cross the BBB, as described herein above, or administering the agent locally to a subject.

Subjects with cancer or at risk of developing cancer are treated with an effective amount of a P2RX2 inhibitor. The methods described herein also include contacting a tumor or cancer cell with an effective amount of a P2RX2 inhibitor. In some embodiments, an effective amount of a P2RX2 inhibitor is an amount sufficient to decrease tumor innervation or nerve activity in a tumor. In some embodiments, an effective amount of a P2RX2 inhibitor is an amount sufficient to treat the cancer or tumor, cause remission, reduce tumor growth, reduce tumor volume, reduce tumor metastasis, reduce tumor invasion, reduce tumor proliferation, reduce tumor migration, or reduce tumor number, reduce P2RX2 expression, reduce P2RX2 copy number, increase cancer cell death, increase time to recurrence, or improve survival.

The P2RX2 inhibitors described herein are administered in an amount (e.g., an effective amount) and for a time sufficient to effect one of the outcomes described above. The P2RX2 inhibitor may be administered once or more than once. The P2RX2 inhibitor may be administered once daily, twice daily, three times daily, once every two days, once weekly, twice weekly, three times weekly, once biweekly, once monthly, once bimonthly, twice a year, or once yearly. Treatment may be discrete (e.g., an injection) or continuous (e.g., treatment via an implant or infusion pump). Subjects may be evaluated for treatment efficacy 1 week, 2 weeks, 1 month, 2 months, 3 months, 4 months, 5 months, 6 months or more following administration of a P2RX2 inhibitor depending on the P2RX2 inhibitor and route of administration used for treatment. Depending on the outcome of the evaluation, treatment may be continued or ceased, treatment frequency or dosage may change, or the patient may be treated with a different P2RX2 inhibitor. Subjects may be treated for a discrete period of time (e.g., 1, 2, 3, 4, 5, 6, 7, 8, 9, 10, 11, or 12 months) or until the disease or condition is alleviated, or treatment may be chronic depending on the severity and nature of the disease or condition being treated.

Kits

The invention also features a kit including (a) a pharmaceutical composition including a P2RX2 inhibitor described herein, and (b) instructions for administering the pharmaceutical composition to treat cancer.

EXAMPLES

The following examples are provided to further illustrate some embodiments of the present invention, but are not intended to limit the scope of the invention; it will be understood by their exemplary nature that other procedures, methodologies, or techniques known to those skilled in the art may alternatively be used.

Example 1—Identification of P2RX2 as Essential for Pancreatic Cancer Growth and Proliferation A library of lentiviral-encoded guide RNAs (gRNA) that individually target neuronal genes was synthesized (Cellecta, Inc.) to obtain a library coverage of six unique gRNAs per gene. Pancreatic cancer cell lines, PANC1, MIAPACA2, and BXPC3, were transduced with a lentiviral-encoded Cas9 nuclease at a high multiplicity of infection (MOI), then transduced with the gRNA lentivirus library at a low MOI of 0.5 to ensure that individual cells received approximately one gRNA. The gRNA library vector also encodes puromycin resistance. One day post-transduction, cells were incubated with puromycin for four days to select for successfully-transduced cells.

Following transduction and selection, $10 \times 10^6$ cells were harvested to serve as the "baseline" population from which the growth effects of individual genes would be compared. For the in vitro arm, $10 \times 10^6$ cells were plated in manufacturer's recommended medium and split twice weekly for four weeks, by re-plating $10 \times 10^6$ cells at each split. For the in vivo subcutaneous arm, $5 \times 10^6$ cells were implanted subcutaneously into NOD-SCID mice, with three mice per replicate, and allowed to grow for four weeks. For the in vivo orthotopic arm, $5 \times 10^5$ cells were implanted orthotopically into the pancreas of NOD-SCID mice, with 10 mice per replicate, and allowed to grow for four weeks.

Following the four weeks of cell/tumor growth, DNA from in vitro and in vivo samples was isolated by tissue homogenization and lysis using a DNA extraction kit (Qiagen DNeasy Blood and Tissue Kit), and concentrated by ethanol precipitation. The DNA samples were amplified by two rounds of PCR using manufacturer's recommended primers and analyzed by next-generation sequencing (BGIAmerica). Sequencing results were analyzed to call hits using a Model-based Analysis of Genome-wide CRISPR-Cas9 Knockout (MAGeCK) algorithm as described by Li W et al., Genome Biology 2014 and Li W et al., Genome Biology 2015. In brief, sequencing reads were normalized to their medians, the variance of read counts for individual gRNAs were estimated and normalized, and individual gRNA read count differences were ranked against each other. Target genes were called based on whether multiple gRNAs targeting a single gene ranked near the top of the gRNA ranking list.

Target genes were quantified along three parameters: the Beta score, essentially the magnitude of the effect (log-fold change in gRNA count); the p-value; and the false discovery rate (FDR). Beta scores <0 indicated that the six gRNAs targeting a single gene were absent from the late stage sample compared to the baseline sample, and were a good indication that the gene was "dropping out" in the course of tumor growth. P-value and FDR both reflected the confidence that the result was not artifactual, with a lower value indicating higher confidence. Thresholds for calling hits were P-value <0.1 and FDR <0.5.

P2RX2 showed up as a significant hit in multiple model systems, as shown in Table 13 below. The data indicate that P2RX2 is essential to the growth and proliferation of pancreatic cancer.

TABLE 13

P2RX2 CRISPR RESULTS

| Gene | B-Score | P-Value | FDR | Condition |
|---|---|---|---|---|
| P2RX2 | −0.62 | 0.00025 | 0.0057 | in vitro_Miapaca2 |
| P2RX2 | −0.46 | 0.0052 | 0.22 | subQ_Miapaca2 |
| P2RX2 | −0.52 | 0.012 | 0.34 | subQ_Panc1 |

Example 2—Generation of a P2RX2-Specific Inhibitory Antibody

The protein P2RX2 is recombinantly expressed in a mammalian cell culture system, e.g., HEK or CHO cells. Membrane vesicle preparation of the transgene-expressing cells is performed using hypertonic vesiculation buffer, a technique described in Del Piccolo et al., Analytical Chemistry, 84:8650, 2012. Using routine methods such as phage display, yeast display, or animal immunization, an antibody is raised that is specific to P2RX2 vesicles compared to vesicles prepared from non-transgene-modified cells as measured by ELISA. To confirm that the antibody prevents cation flux, transgene-expressing cells are labeled with a calcium reporter dye, e.g., Fluo-8 dye (Abcam ab112129), which fluoresces upon binding with calcium. The cells are incubated with extracellular ATP to trigger calcium flux through the P2RX2 channel in the presence or absence of the antibody to evaluate inhibitory antibody function.

Example 3—Treatment of a Patient with Cancer with a P2RX2 Inhibitor

According to the methods disclosed herein, a physician of skill in the art can treat a patient, such as a human patient with cancer (e.g., pancreatic cancer), so as to inhibit cancer growth, reduce tumor burden, increase cancer cell death, or slow disease progression. The method of treatment can include diagnosing or identifying a patient as a candidate for treatment with a P2RX2 inhibitor based on P2RX2 expression in a biopsy. For example, a tissue sample can be collected from a patient's cancer and analyzed for RNA expression by qPCR or RNAseq analysis, and the cancer can be found to express high levels of P2RX2. To treat the patient, a physician of skill in the art can administer a P2RX2 inhibitor that decreases P2RX2 expression or function (e.g., an inhibitory RNA directed to P2RX2, a P2RX2 inhibitory antibody, or a P2RX2 small molecule inhibitor, e.g., CHEMBL494161). The P2RX2 inhibitor can be administered locally (e.g., injected into the tumor or tumor microenvironment) to decrease tumor growth or volume. The P2RX2 inhibitor is administered in a therapeutically effective amount, such as from 10 μg/kg to 500 mg/kg (e.g., 10 μg/kg, 100 μg/kg, 500 μg/kg, 1 mg/kg, 10 mg/kg, 50 mg/kg, 100 mg/kg, 250 mg/kg, or 500 mg/kg). In some embodiments, the P2RX2 inhibitor is administered bimonthly, once a month, once every two weeks, or at least once a week or more (e.g., 1, 2, 3, 4, 5, 6, or 7 times a week or more).

The P2RX2 inhibitor is administered to the patient in an amount sufficient to decrease tumor growth decrease tumor burden, increase cancer cell death, or increase progression free survival by 10% or more (e.g., 10%, 20%, 30%, 40%, 50%, 60%, 70%, 80%, 90%, 95% or more). Tumor growth and tumor burden can be assessed using standard imaging methods (e.g., digital radiography, positron emission tomography (PET) scan, computed tomography (CT) scan, or magnetic resonance imaging (MRI) scan). Images from before and after administration of the P2RX2 inhibitor can be compared to evaluate the efficacy of the treatment, and the rate of disease progression can be assessed by comparison to the patient's medical history prior to administration of the P2RX2 inhibitor. A finding of a reduction in the total number of tumors, number of primary tumors, volume of tumors, growth of tumors, or rate of disease progression indicates that the P2RX2 inhibitor has successfully treated the cancer.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and may be applied to the essential features hereinbefore set forth, and follows in the scope of the claims. Other embodiments are within the claims.

What is claimed is:

1. A method of treating a human subject identified as having pancreatic cancer, the method comprising administering to the subject an amount of a small molecule P2RX2 antagonist effective to reduce growth of the pancreatic cancer, thereby treating the subject, wherein the small molecule P2RX2 antagonist is selected from the group consisting of CHEMBL494161, CHEMBL119416, CHEMBL604158, CHEMBL1672098, CHEMBL495204, CHEMBL 499580, CHEMBL598857, CHEMBL1671997, CHEMBL523173, CHEMBL1672107, CHEMBL597820, CHEMBL1671996, CHEMBL492300, CHEMBL523043, CHEMBL597591, CHEMBL1671993, CHEMBL494159, CHEMBL521983, CHEMBL597203, CHEMBL1671992, CHEMBL494353, CHEMBL500550, CHEMBL596982, CHEMBL134193, CHEMBL494160, CHEMBL492299, CHEMBL524284, CHEMBL133576, CHEMBL494158, CHEMBL504607, CHEMBL524064, CHEMBL131271, CHEMBL526307, CHEMBL494176, CHEMBL522725, CHEMBL118007, CHEMBL492934, CHEMBL493547, CHEMBL522053, CHEMBL116926, CHEMBL492933, CHEMBL493546, CHEMBL521709, CHEMBL492729, CHEMBL494582, CHEMBL446310, CHEMBL499428, CHEMBL521820, CHEMBL492907, CHEMBL69727, CHEMBL498038, CHEMBL494940, CHEMBL492703, CHEMBL331358, CHEMBL496229, CHEMBL492789, CHEMBL1672104, CHEMBL494833, CHEMBL496022, CHEMBL69234, CHEMBL495203, CHEMBL509572, CHEMBL495834, CHEMBL401735, CHEMBL1672105, CHEMBL496030, CHEMBL495796, CHEMBL494834, CHEMBL448525, CHEMBL1671995, CHEMBL450832, CHEMBL494832, CHEMBL271672, CHEMBL523000, CHEMBL404659, CHEMBL494772, CHEMBL496401, CHEMBL492968, CHEMBL404450, CHEMBL494181, CHEMBL413145, CHEMBL271688, CHEMBL403051, CHEMBL257495, CHEMBL119180, CHEMBL494581, CHEMBL402239, CHEMBL117766, CHEMBL502618, CHEMBL45413, CHEMBL256864, CHEMBL495195, CHEMBL444469, CHEMBL331250, CHEMBL256688, CHEMBL493740, CHEMBL1672106, CHEMBL492967, CHEMBL256057, CHEMBL492562, CHEMBL493741, CHEMBL492744, CHEMBL1672103, CHEMBL477339, CHEMBL443930, CHEMBL606414, CHEMBL1672102, CHEMBL492935, CHEMBL604300, CHEMBL1672099, CHEMBL522184, and CHEMBL492745.

* * * * *